US009622483B2

(12) United States Patent
Bookbinder et al.

(10) Patent No.: US 9,622,483 B2
(45) Date of Patent: Apr. 18, 2017

(54) ANTIMICROBIAL GLASS COMPOSITIONS, GLASSES AND POLYMERIC ARTICLES INCORPORATING THE SAME

(71) Applicant: CORNING INCORPORATED, Corning, NY (US)

(72) Inventors: Dana Craig Bookbinder, Corning, NY (US); Gary Stephen Calabrese, Corning, NY (US); Timothy Michael Gross, Corning, NY (US); Dayue Jiang, Painted Post, NY (US); Jianguo Wang, Horseheads, NY (US)

(73) Assignee: CORNING INCORPORATED, Corning, NY (US)

( * ) Notice: Subject to any disclaimer, the term of this patent is extended or adjusted under 35 U.S.C. 154(b) by 0 days.

(21) Appl. No.: 14/623,077

(22) Filed: Feb. 16, 2015

(65) Prior Publication Data

US 2015/0230476 A1    Aug. 20, 2015

Related U.S. Application Data

(60) Provisional application No. 62/034,842, filed on Aug. 8, 2014, provisional application No. 62/034,834, filed on Aug. 8, 2014, provisional application No. 62/026,186, filed on Jul. 18, 2014, provisional application No. 62/026,177, filed on Jul. 18, 2014, provisional application No. 61/992,987, filed on May 14, 2014, provisional application No. 61/992,980, filed on May 14, 2014, provisional application No. 61/941,690, filed on Feb. 19, 2014, provisional application No. 61/941,677, filed on Feb. 19, 2014.

(51) Int. Cl.
| | |
|---|---|
| *A01N 59/20* | (2006.01) |
| *C03C 4/00* | (2006.01) |
| *C03C 3/085* | (2006.01) |
| *C03C 3/089* | (2006.01) |
| *C03C 3/097* | (2006.01) |
| *C03C 3/093* | (2006.01) |
| *A01N 59/06* | (2006.01) |
| *A01N 59/00* | (2006.01) |
| *A01N 59/14* | (2006.01) |
| *A01N 59/26* | (2006.01) |
| *A01N 59/16* | (2006.01) |
| *A01N 25/00* | (2006.01) |

(52) U.S. Cl.
CPC ............. *A01N 59/20* (2013.01); *A01N 25/00* (2013.01); *A01N 59/00* (2013.01); *A01N 59/06* (2013.01); *A01N 59/14* (2013.01); *A01N 59/16* (2013.01); *A01N 59/26* (2013.01); *C03C 3/085* (2013.01); *C03C 3/089* (2013.01); *C03C 3/093* (2013.01); *C03C 3/097* (2013.01); *C03C 4/00* (2013.01); *C03C 2204/02* (2013.01)

(58) Field of Classification Search
CPC ........ A01N 59/20; A01N 59/06; A01N 59/00; A01N 59/14; A01N 59/26; A01N 59/16; A01N 25/00; C03C 4/00; C03C 3/085; C03C 3/089; C03C 3/097; C03C 3/093
See application file for complete search history.

(56) References Cited

U.S. PATENT DOCUMENTS

| | | | |
|---|---|---|---|
| 3,414,465 A | 12/1968 | Baak et al. | |
| 3,564,587 A | 2/1971 | Ellis | |
| 4,098,610 A | 7/1978 | Wexell | ......................... 106/47 R |
| 4,328,022 A | 5/1982 | Bonk et al. | ....................... 65/43 |
| 5,290,544 A | 3/1994 | Shimono et al. | |
| 5,766,611 A | 6/1998 | Shimono et al. | |

(Continued)

FOREIGN PATENT DOCUMENTS

| | | |
|---|---|---|
| CA | 2503446 C | 5/2004 |
| CN | 2515956 A1 | 10/2002 |

(Continued)

OTHER PUBLICATIONS

Matusita K.' 'Sakka S.' 'Shouji T.', Thermal Expansion of Substituted Copper Aluminosilicate Glasses, J.Am.Ceram.Soc., 1983, vol. 66, No. 1, p. 33.
Patent Cooperation Treaty International Notification of Transmittal of the International Search Report and The Written Opinion of the International Searching Authority, international application No. PCT/US2015/016104: mailing date Jun. 25, 2015, 15 pages.
Hamzawy et al. "Crystallisation of Cu-containing K-fluor-richterite (KNaCa(Mg, Cu)5 Si8O22F2) glasses." Glass Technology, 2005, 46 (3), 281-286.
Ahmed et al., "Effect of Heat Treatment on the Crystallisation of Cuprous Oxide in Glass," Glass Research Laboratory, National Research Center, Dokki, Cairo, Egypt, Glass Technology, vol. 22, No. 1, Feb. 1981.

(Continued)

*Primary Examiner* — Ali Soroush
*Assistant Examiner* — Genevieve S Alley
(74) *Attorney, Agent, or Firm* — Payal A. Patel

(57) ABSTRACT

Embodiments of the present invention pertain to antimicrobial glass compositions, glasses and articles. The articles include a glass, which may include a glass phase and a cuprite phase. In other embodiments, the glasses include as plurality of $Cu^{1+}$ ions, a degradable phase including $B_2O_3$, $P_2O_5$ and $K_2O$ and a durable phase including $SiO_2$. Other embodiments include glasses having a plurality of $Cu^{1+}$ ions disposed on the surface of the glass and in the glass network and/or the glass matrix. The article may also include a polymer. The glasses and articles disclosed herein exhibit a 2 log reduction or greater in a concentration of at least one of *Staphylococcus aureus*, *Enterobacter aerogenes*, *Pseudomonas aeruginosa* bacteria, Methicillin Resistant *Staphylococcus aureus*, and *E. coli*, under the EPA Test Method for Efficacy of Copper Alloy as a Sanitizer testing conditions and under Modified JIS Z 2801 for Bacteria testing conditions. In some embodiments, the glass and articles exhibit a 2 log reduction or greater in a concentration of *Murine Norovirus* under Modified JIS Z 2801 Test for Viruses testing conditions.

9 Claims, 15 Drawing Sheets

(56) References Cited

U.S. PATENT DOCUMENTS

| | | | |
|---|---|---|---|
| 6,143,318 A | 11/2000 | Gilchrist et al. | |
| 6,238,686 B1 | 5/2001 | Burrell et al. | |
| 6,303,183 B1 | 10/2001 | Wilczynski et al. | |
| 6,342,460 B1 | 1/2002 | Akimoto et al. | 501/55 |
| 6,417,423 B1 | 7/2002 | Koper et al. | |
| 6,485,735 B1 | 11/2002 | Steen et al. | |
| 6,485,950 B1 | 11/2002 | Kumar et al. | |
| 6,582,715 B1 | 6/2003 | Barry et al. | 424/422 |
| 6,652,875 B1 | 11/2003 | Bannister | |
| 6,749,759 B2 | 6/2004 | Denes et al. | |
| 6,939,820 B2 | 9/2005 | Numaguchi et al. | 501/45 |
| 7,098,256 B2 | 8/2006 | Ong et al. | 522/97 |
| 7,192,602 B2 | 3/2007 | Fechner et al. | |
| 7,282,194 B2 | 10/2007 | Sung et al. | |
| 7,311,944 B2 | 12/2007 | Sambasivan et al. | |
| 7,329,301 B2 | 2/2008 | Chang et al. | |
| 7,357,949 B2 | 4/2008 | Trogolo et al. | 424/617 |
| 7,374,693 B1 | 5/2008 | Routberg et al. | |
| 7,381,751 B2 | 6/2008 | Sarangapani | |
| 7,390,343 B2 | 6/2008 | Tepper et al. | |
| 7,491,554 B2 | 2/2009 | Fujimura et al. | |
| 7,521,056 B2 | 4/2009 | Chang et al. | |
| 7,521,394 B2 | 4/2009 | Xie et al. | |
| 7,556,789 B2 | 7/2009 | Fahlman | |
| 7,595,355 B2 | 9/2009 | Trogolo | 523/122 |
| 7,597,900 B2 | 10/2009 | Zimmer et al. | |
| 7,704,903 B2 | 4/2010 | Seneschal et al. | |
| 7,709,027 B2 | 5/2010 | Fechner et al. | |
| 7,781,498 B2 | 8/2010 | Krishnan | |
| 7,816,292 B2 | 10/2010 | Zimmer et al. | |
| 7,833,340 B2 | 11/2010 | Wakizaka | |
| 7,963,646 B2 | 6/2011 | Magdassi et al. | |
| 8,034,732 B2 | 10/2011 | Kobayashi et al. | |
| 8,056,733 B2 | 11/2011 | Koslow | |
| 8,080,490 B2 | 12/2011 | Fechner et al. | |
| 8,083,851 B2 | 12/2011 | Crudden et al. | |
| 8,092,912 B2 | 1/2012 | Veerasamy et al. | |
| 8,187,473 B2 | 5/2012 | Prasad | |
| 8,221,833 B2 | 7/2012 | Veerasamy et al. | |
| 8,256,233 B2 | 9/2012 | Boyden et al. | |
| 8,257,714 B2 | 9/2012 | Aylsworth et al. | |
| 8,257,732 B2 | 9/2012 | Huey et al. | |
| 8,258,202 B2 | 9/2012 | Chasser et al. | |
| 8,258,296 B2 | 9/2012 | Paredes et al. | |
| 8,262,568 B2 | 9/2012 | Albrecht et al. | |
| 8,262,868 B2 | 9/2012 | Brooks et al. | |
| 8,263,114 B2 | 9/2012 | Berlat | |
| 8,263,153 B2 | 9/2012 | Forchhammer et al. | |
| 8,263,503 B2 | 9/2012 | Cawse et al. | |
| 8,263,656 B2 | 9/2012 | Firooznia et al. | |
| 8,268,343 B2 | 9/2012 | Saxena et al. | |
| 8,273,303 B2 | 9/2012 | Ferlic et al. | |
| 8,273,404 B2 | 9/2012 | Dave et al. | |
| 8,273,452 B2 | 9/2012 | Guo et al. | |
| 8,277,807 B2 | 10/2012 | Gallagher et al. | |
| 8,277,827 B2 | 10/2012 | Toreki et al. | |
| 8,277,899 B2 | 10/2012 | Krogman et al. | |
| 8,282,776 B2 | 10/2012 | Smith et al. | |
| 8,317,516 B2 | 11/2012 | Rusin et al. | |
| 8,568,849 B2 | 10/2013 | Shi et al. | |
| 8,809,820 B2 | 8/2014 | Dahm | |
| 8,900,624 B2 | 12/2014 | Karandikar et al. | |
| 9,028,962 B2 | 5/2015 | Borrelli et al. | |
| 9,115,470 B2 | 8/2015 | Musick et al. | |
| 9,144,242 B2 | 9/2015 | Averett et al. | |
| 9,193,820 B2 | 11/2015 | Karandikar et al. | |
| 9,228,090 B2 | 1/2016 | Musick | |
| 9,307,759 B2 | 4/2016 | Musick | |
| 2002/0045010 A1 | 4/2002 | Rohrbaugh et al. | |
| 2002/0128249 A1 | 9/2002 | Cook | |
| 2003/0167878 A1 | 9/2003 | Al-Salim et al. | |
| 2003/0213503 A1 | 11/2003 | Price et al. | |
| 2004/0206267 A1 | 10/2004 | Sambasivan et al. | |
| 2004/0234604 A1 | 11/2004 | Mecking et al. | |
| 2004/0253435 A1 | 12/2004 | Nomura | 428/327 |
| 2005/0031703 A1 | 2/2005 | Beier et al. | |
| 2005/0095303 A1 | 5/2005 | Krenitski et al. | |
| 2005/0152955 A1 | 7/2005 | Akhave et al. | |
| 2005/0175552 A1 | 8/2005 | Hoic et al. | |
| 2005/0175649 A1 | 8/2005 | Disalvo et al. | |
| 2005/0182152 A1 | 8/2005 | Nonninger et al. | |
| 2005/0207993 A1 | 9/2005 | Bazemore et al. | |
| 2005/0224417 A1 | 10/2005 | Wien et al. | |
| 2005/0224419 A1 | 10/2005 | Wien et al. | |
| 2005/0258288 A1 | 11/2005 | Dalziel et al. | |
| 2006/0115536 A1 | 6/2006 | Yacaman et al. | |
| 2006/0127310 A1 | 6/2006 | Russell-Jones et al. | |
| 2006/0142413 A1 | 6/2006 | Zimmer et al. | |
| 2006/0166806 A1 | 7/2006 | Fechner et al. | |
| 2006/0172013 A1 | 8/2006 | Hirai | |
| 2006/0188580 A1 | 8/2006 | Sacks | |
| 2006/0193902 A1 | 8/2006 | Tardi et al. | |
| 2006/0198903 A1 | 9/2006 | Storey et al. | |
| 2006/0272542 A1 | 12/2006 | Horner et al. | |
| 2006/0280785 A1 | 12/2006 | Easterly et al. | |
| 2006/0281961 A1 | 12/2006 | Prasad | |
| 2006/0286051 A1 | 12/2006 | Tanaka et al. | |
| 2007/0062870 A1 | 3/2007 | Chen et al. | |
| 2007/0081958 A1 | 4/2007 | Bechert et al. | |
| 2007/0116734 A1 | 5/2007 | Akash | |
| 2007/0122356 A1 | 5/2007 | Kessler et al. | |
| 2007/0122359 A1 | 5/2007 | Wang et al. | |
| 2007/0158611 A1 | 7/2007 | Oldenburg | |
| 2007/0195259 A1 | 8/2007 | Olsson | 351/43 |
| 2007/0196605 A1 | 8/2007 | Ong | 428/35.7 |
| 2007/0199890 A1 | 8/2007 | Trogolo | |
| 2007/0208102 A1 | 9/2007 | Reynaud et al. | |
| 2007/0225409 A1 | 9/2007 | Matsumoto | |
| 2007/0243237 A1 | 10/2007 | Khaled et al. | |
| 2007/0243263 A1 | 10/2007 | Trogolo | |
| 2007/0254163 A1 | 11/2007 | Veerasamy et al. | |
| 2007/0292355 A1 | 12/2007 | Tamarkin et al. | |
| 2008/0031938 A1 | 2/2008 | Easterly et al. | |
| 2008/0032060 A1 | 2/2008 | Nesbitt | |
| 2008/0047894 A1 | 2/2008 | Trogolo et al. | |
| 2008/0051493 A1 | 2/2008 | Trogolo et al. | |
| 2008/0053922 A1 | 3/2008 | Honsinger et al. | |
| 2008/0066741 A1 | 3/2008 | LeMahieu et al. | |
| 2008/0085326 A1 | 4/2008 | Ruan | |
| 2008/0156232 A1 | 7/2008 | Crudden et al. | |
| 2008/0171068 A1 | 7/2008 | Wyner et al. | |
| 2008/0220037 A1 | 9/2008 | Denizot et al. | |
| 2008/0269186 A1 | 10/2008 | Bignozzi et al. | |
| 2008/0292671 A1 | 11/2008 | Ho et al. | |
| 2008/0292675 A1 | 11/2008 | Edermatt et al. | |
| 2008/0299160 A1 | 12/2008 | Agboh et al. | |
| 2009/0001012 A1 | 1/2009 | Kepner | |
| 2009/0023867 A1 | 1/2009 | Nishijima et al. | |
| 2009/0048368 A1 | 2/2009 | Bash et al. | |
| 2009/0068241 A1 | 3/2009 | Britz et al. | |
| 2009/0098366 A1 | 4/2009 | Smoukov et al. | |
| 2009/0104369 A1 | 4/2009 | Rajala et al. | |
| 2009/0130161 A1 | 5/2009 | Sarangapani | |
| 2009/0131517 A1 | 5/2009 | Height et al. | |
| 2009/0133583 A1 | 5/2009 | Lee et al. | |
| 2009/0133810 A1 | 5/2009 | Penalva | |
| 2009/0142584 A1 | 6/2009 | Bedel et al. | |
| 2009/0147370 A1 | 6/2009 | Parkin et al. | |
| 2009/0151571 A1 | 6/2009 | Lee et al. | |
| 2009/0162695 A1 | 6/2009 | Hevesi et al. | |
| 2009/0186013 A1 | 7/2009 | Stucky et al. | |
| 2009/0186756 A1 | 7/2009 | Cheng et al. | |
| 2009/0209629 A1 | 8/2009 | Mirkin et al. | |
| 2009/0263496 A1 | 10/2009 | Kijlstra et al. | |
| 2009/0314628 A1 | 12/2009 | Lee et al. | |
| 2009/0317435 A1 | 12/2009 | Vandesteeg et al. | |
| 2009/0324990 A1 | 12/2009 | Pilloy et al. | |
| 2010/0003203 A1 | 1/2010 | Karpov et al. | |
| 2010/0004350 A1 | 1/2010 | Zalich et al. | |
| 2010/0021559 A1 | 1/2010 | Kuznicki | |
| 2010/0034873 A1 | 2/2010 | Delprete | |
| 2010/0035047 A1 | 2/2010 | Ajayan et al. | |
| 2010/0040655 A1 | 2/2010 | Ren et al. | |
| 2010/0086605 A1 | 4/2010 | Bignozzi et al. | |

(56) References Cited

U.S. PATENT DOCUMENTS

| | | |
|---|---|---|
| 2010/0111844 A1 | 5/2010 | Boyden et al. |
| 2010/0111845 A1 | 5/2010 | Boyden et al. |
| 2010/0119829 A1 | 5/2010 | Karpov et al. |
| 2010/0120942 A1 | 5/2010 | Ajayan et al. |
| 2010/0158851 A1 | 6/2010 | Yeung et al. |
| 2010/0178270 A1 | 7/2010 | Helling |
| 2010/0189901 A1 | 7/2010 | Chung et al. |
| 2010/0190004 A1 | 7/2010 | Gibbins et al. |
| 2010/0193744 A1 | 8/2010 | Avakian |
| 2010/0205709 A1 | 8/2010 | Grune et al. |
| 2010/0227052 A1 | 9/2010 | Carter et al. |
| 2010/0230344 A1 | 9/2010 | Srinivas et al. |
| 2010/0233146 A1 | 9/2010 | McDaniel |
| 2010/0234209 A1 | 9/2010 | Furukawa et al. |
| 2010/0247590 A1 | 9/2010 | Anton et al. |
| 2010/0255080 A1 | 10/2010 | Sanmiguel et al. |
| 2010/0264401 A1 | 10/2010 | Adivarahan et al. |
| 2010/0266646 A1 | 10/2010 | Dvorak et al. |
| 2010/0278771 A1 | 11/2010 | Lobe et al. |
| 2010/0297376 A1 | 11/2010 | Shi et al. |
| 2010/0304182 A1 | 12/2010 | Facchini et al. |
| 2010/0330380 A1 | 12/2010 | Colreavy et al. |
| 2011/0005997 A1 | 1/2011 | Kurth et al. |
| 2011/0014258 A1 | 1/2011 | Gan et al. |
| 2011/0014300 A1 | 1/2011 | Muthusamy et al. |
| 2011/0027385 A1 | 2/2011 | Cairns et al. |
| 2011/0027599 A1 | 2/2011 | Hoek et al. |
| 2011/0028311 A1 | 2/2011 | Etacheri et al. |
| 2011/0111204 A1 | 5/2011 | Veerasamy et al. |
| 2011/0127464 A1 | 6/2011 | Zinn et al. |
| 2011/0132144 A1 | 6/2011 | Mezger et al. |
| 2011/0143417 A1 | 6/2011 | Chang et al. |
| 2011/0144765 A1 | 6/2011 | Jones et al. |
| 2011/0155968 A1 | 6/2011 | Iha et al. |
| 2011/0182951 A1 | 7/2011 | Burger et al. |
| 2011/0189250 A1 | 8/2011 | John et al. |
| 2011/0193007 A1 | 8/2011 | Avakian |
| 2011/0193034 A1 | 8/2011 | Nakamoto et al. |
| 2011/0200656 A1 | 8/2011 | Olsson ............ 424/405 |
| 2011/0212832 A1 | 9/2011 | Nakano et al. |
| 2011/0217544 A1 | 9/2011 | Young et al. |
| 2011/0223057 A1 | 9/2011 | Della Valle et al. |
| 2011/0223258 A1 | 9/2011 | Nikolaev |
| 2011/0226786 A1 | 9/2011 | Remington et al. |
| 2011/0236343 A1 | 9/2011 | Chisholm et al. |
| 2011/0236430 A1 | 9/2011 | Lin et al. |
| 2011/0236441 A1 | 9/2011 | Ohrlander et al. |
| 2011/0252580 A1 | 10/2011 | Miller et al. |
| 2011/0268802 A1 | 11/2011 | Dihora et al. |
| 2011/0281070 A1 | 11/2011 | Mittal et al. |
| 2011/0295190 A1 | 12/2011 | David et al. |
| 2011/0311604 A1 | 12/2011 | Xu et al. |
| 2012/0066956 A1 | 3/2012 | Lyngstadaas et al. |
| 2012/0115981 A1 | 5/2012 | Verne' et al. |
| 2012/0145651 A1 | 6/2012 | Chen et al. |
| 2012/0223022 A1 | 9/2012 | Hassler et al. |
| 2012/0225027 A1 | 9/2012 | Exner et al. |
| 2012/0225905 A1 | 9/2012 | Padilla et al. |
| 2012/0230870 A1 | 9/2012 | Franciskovich et al. |
| 2012/0231704 A1 | 9/2012 | Mase et al. |
| 2012/0232225 A1 | 9/2012 | Baker et al. |
| 2012/0232298 A1 | 9/2012 | Fang et al. |
| 2012/0234176 A1 | 9/2012 | Lee |
| 2012/0237406 A1 | 9/2012 | Lee |
| 2012/0237789 A1 | 9/2012 | Wang et al. |
| 2012/0240452 A1 | 9/2012 | Erdoes, Jr. et al. |
| 2012/0241498 A1 | 9/2012 | Gonzalez et al. |
| 2012/0241502 A1 | 9/2012 | Aldridge et al. |
| 2012/0244139 A1 | 9/2012 | Madison et al. |
| 2012/0244369 A1 | 9/2012 | Ober et al. |
| 2012/0251381 A1 | 10/2012 | Bedworth et al. |
| 2012/0251517 A1 | 10/2012 | Frost et al. |
| 2012/0251756 A1 | 10/2012 | Buckley et al. |
| 2012/0252774 A1 | 10/2012 | White et al. |
| 2012/0255623 A1 | 10/2012 | Bell et al. |
| 2012/0258176 A1 | 10/2012 | Sung et al. |
| 2012/0258244 A1 | 10/2012 | Veerasamy et al. |
| 2012/0258313 A1 | 10/2012 | Wen et al. |
| 2012/0259052 A1 | 10/2012 | Nelson et al. |
| 2012/0259073 A1 | 10/2012 | Ait-Haddou et al. |
| 2012/0259376 A1 | 10/2012 | Godden |
| 2012/0259391 A1 | 10/2012 | Godden |
| 2012/0261344 A1 | 10/2012 | Kurth et al. |
| 2012/0263807 A1 | 10/2012 | Horinek et al. |
| 2012/0263863 A1 | 10/2012 | Nesbitt |
| 2012/0264078 A1 | 10/2012 | Patel et al. |
| 2012/0264884 A1 | 10/2012 | Liu et al. |
| 2012/0269870 A1 | 10/2012 | Jiang et al. |
| 2012/0271248 A1 | 10/2012 | Nesbitt et al. |
| 2012/0271396 A1 | 10/2012 | Zheng et al. |
| 2012/0275960 A1 | 11/2012 | Seck |
| 2012/0276219 A1 | 11/2012 | Taylor et al. |
| 2012/0279953 A1 | 11/2012 | Augustine et al. |
| 2012/0282434 A1 | 11/2012 | Cawse et al. |
| 2012/0283171 A1 | 11/2012 | Putman |
| 2012/0283172 A1 | 11/2012 | Wallen, III |
| 2012/0283410 A1 | 11/2012 | Mirosevich et al. |
| 2012/0283538 A1 | 11/2012 | Rose et al. |
| 2012/0284946 A1 | 11/2012 | Green |
| 2012/0285574 A1 | 11/2012 | Mason |
| 2012/0288678 A1 | 11/2012 | Grube et al. |
| 2012/0288697 A1 | 11/2012 | Wu et al. |
| 2012/0288813 A1 | 11/2012 | Reid et al. |
| 2012/0289107 A1 | 11/2012 | Beissinger et al. |
| 2012/0289686 A1 | 11/2012 | Baker et al. |
| 2012/0289887 A1 | 11/2012 | Visco et al. |
| 2012/0296029 A1 | 11/2012 | Liu et al. |
| 2012/0296284 A1 | 11/2012 | Anderson et al. |
| 2012/0301533 A1 | 11/2012 | Uhlmann et al. |
| 2012/0304402 A1 | 12/2012 | Miracle et al. |
| 2012/0305132 A1 | 12/2012 | Maness |
| 2012/0305804 A1 | 12/2012 | Goldman |
| 2012/0308623 A1 | 12/2012 | Taxt-Lamolle et al. |
| 2012/0308630 A1 | 12/2012 | Averett et al. |
| 2012/0312797 A1 | 12/2012 | Augustine et al. |
| 2012/0315201 A1 | 12/2012 | Ferlic et al. |
| 2012/0315240 A1 | 12/2012 | Alper |
| 2012/0315336 A1 | 12/2012 | Ruddy et al. |
| 2012/0321553 A1 | 12/2012 | Zeng et al. |
| 2012/0321691 A1 | 12/2012 | Huey et al. |
| 2012/0321698 A1 | 12/2012 | Narain et al. |
| 2012/0321870 A1 | 12/2012 | Allen et al. |
| 2012/0322903 A1 | 12/2012 | Karandikar et al. |
| 2012/0328564 A1 | 12/2012 | Govindan et al. |
| 2012/0328615 A1 | 12/2012 | Romagne et al. |
| 2012/0328683 A1 | 12/2012 | Song et al. |
| 2012/0328713 A1 | 12/2012 | Olson et al. |
| 2012/0328804 A1 | 12/2012 | Allen et al. |
| 2012/0329675 A1 | 12/2012 | Olson et al. |
| 2013/0001066 A1 | 1/2013 | Brooks et al. |
| 2013/0001204 A1 | 1/2013 | Mistry et al. |
| 2013/0002776 A1 | 1/2013 | Nagashima et al. |
| 2013/0004778 A1 | 1/2013 | Tucker, III |
| 2013/0005811 A1 | 1/2013 | Walcott |
| 2013/0006184 A1 | 1/2013 | Albrecht et al. |
| 2013/0006194 A1 | 1/2013 | Anderson et al. |
| 2014/0017462 A1 | 1/2014 | Borrelli et al. |
| 2014/0120322 A1 | 5/2014 | Fu et al. |
| 2014/0170204 A1 | 6/2014 | Desai et al. |
| 2014/0194733 A1 | 7/2014 | Goforth et al. |
| 2014/0202943 A1 | 7/2014 | Pradeep et al. |
| 2014/0205546 A1 | 7/2014 | Macoviak |
| 2014/0220091 A1 | 8/2014 | Tofail et al. |
| 2014/0308867 A1 | 10/2014 | Van Emmerick et al. |

FOREIGN PATENT DOCUMENTS

| | | |
|---|---|---|
| CN | 1420146 A | 5/2003 |
| CN | 101189971 A | 6/2008 |
| CN | 101638537 A1 | 2/2010 |
| CN | 101805546 | 8/2010 |
| CN | 101884807 | 11/2010 |
| CN | 101889582 A | 11/2010 |
| CN | 102348844 A | 2/2012 |

(56) References Cited

FOREIGN PATENT DOCUMENTS

| | | | |
|---|---|---|---|
| CN | 102380127 A | 3/2012 | |
| EP | 0665004 B1 | 8/1995 | |
| EP | 0677989 B1 | 10/1995 | |
| EP | 1603600 B1 | 12/2005 | |
| EP | 1715915 B1 | 11/2006 | |
| EP | 1748353 B1 | 1/2007 | |
| EP | 1780318 B1 | 5/2007 | |
| EP | 1809306 B1 | 7/2007 | |
| EP | 1886981 B1 | 2/2008 | |
| EP | 2004246 B1 | 12/2008 | |
| EP | 2016115 B1 | 1/2009 | |
| EP | 2016200 B1 | 1/2009 | |
| EP | 2113282 B1 | 4/2009 | |
| EP | 2123400 B1 | 11/2009 | |
| EP | 2506792 | 12/2009 | |
| EP | 2509622 | 12/2009 | |
| EP | 2509710 | 12/2009 | |
| EP | 2157211 A1 | 2/2010 | |
| EP | 2303352 B1 | 4/2011 | |
| EP | 2502941 A1 | 9/2012 | |
| EP | 2507248 B1 | 10/2012 | |
| EP | 2508341 A1 | 10/2012 | |
| EP | 2513238 | 10/2012 | |
| EP | 2514359 A2 | 10/2012 | |
| EP | 2515855 | 10/2012 | |
| EP | 2516002 | 10/2012 | |
| EP | 2517720 A1 | 10/2012 | |
| EP | 2522377 A1 | 11/2012 | |
| EP | 2537529 A1 | 12/2012 | |
| EP | 2540309 A2 | 1/2013 | |
| EP | 2540491 A2 | 1/2013 | |
| EP | 2540755 A1 | 1/2013 | |
| EP | 2562624 A1 | 2/2013 | |
| FR | 2953213 A1 | 6/2011 | |
| GB | 2473813 A | 3/2011 | |
| GB | 2490644 A | 7/2012 | |
| GB | 2490239 A | 10/2012 | |
| GB | 2490241 A | 10/2012 | |
| GB | 2490242 A | 10/2012 | |
| GB | 2490243 A | 10/2012 | |
| JP | 60036349 A | 2/1985 | ............ C03C 3/064 |
| JP | 1993041636 B2 | 6/1993 | |
| JP | 1993042574 B2 | 6/1993 | |
| JP | 1993042624 B2 | 6/1993 | |
| JP | 1993045015 82 | 7/1993 | |
| JP | 1993046389 B2 | 7/1993 | |
| JP | 05060670 B2 | 9/1993 | |
| JP | 1993064311 82 | 9/1993 | |
| JP | 1993068530 B2 | 9/1993 | |
| JP | 1993074652 B2 | 10/1993 | |
| JP | 1996027404 A | 1/1996 | |
| JP | 11209143 A | 8/1999 | ............ C03C 3/091 |
| JP | 2000191339 A | 7/2000 | ............ C03C 3/17 |
| JP | 04163778 B2 | 10/2008 | ............ C03C 3/091 |
| JP | 5089165 B2 | 12/2012 | |
| JP | 5099520 B2 | 12/2012 | |
| JP | 2013233492 A | 11/2013 | ............ C02F 1/50 |
| KR | 2011127748 A | 11/2011 | |
| RU | 2414902 C1 | 3/2011 | |
| WO | WO0027768 A1 | 5/2000 | ............ C03C 8/24 |
| WO | 03018494 A3 | 4/2003 | |
| WO | 03050052 A1 | 6/2003 | |
| WO | 2005079738 A1 | 9/2005 | |
| WO | 2007071991 A1 | 6/2007 | |
| WO | WO2007076413 A2 | 7/2007 | ......... A61K 31/4178 |
| WO | WO2007101062 A1 | 9/2007 | ............ A61L 2/16 |
| WO | WO2007134176 A2 | 11/2007 | ............ B65D 81/26 |
| WO | WO2009100164 A2 | 8/2009 | ............ C08K 5/00 |
| WO | 2010041760 A1 | 4/2010 | |
| WO | 2010068985 A1 | 6/2010 | |
| WO | 2011047312 A1 | 4/2011 | |
| WO | 2011053562 A2 | 5/2011 | |
| WO | 2011053719 A1 | 5/2011 | |
| WO | 2011056934 A1 | 5/2011 | |
| WO | 2011057111 A2 | 5/2011 | |
| WO | 2011062938 A2 | 5/2011 | |
| WO | 2011063259 A2 | 5/2011 | |
| WO | 2011063990 A2 | 6/2011 | |
| WO | 2011065997 A1 | 6/2011 | |
| WO | 2011068545 A1 | 6/2011 | |
| WO | 2011068892 A2 | 6/2011 | |
| WO | 2011070364 A1 | 6/2011 | |
| WO | 2011071130 A1 | 6/2011 | |
| WO | 2011072392 A1 | 6/2011 | |
| WO | 2011073969 A1 | 6/2011 | |
| WO | 2011075798 A1 | 6/2011 | |
| WO | 2011078804 A1 | 6/2011 | |
| WO | 2011084811 A1 | 7/2011 | |
| WO | 2011090760 A1 | 7/2011 | |
| WO | 2011092522 A2 | 8/2011 | |
| WO | 2011094293 A1 | 8/2011 | |
| WO | 2011097347 A2 | 8/2011 | |
| WO | 2011100425 A2 | 8/2011 | |
| WO | 2011101642 A2 | 8/2011 | |
| WO | 2011103183 A1 | 8/2011 | |
| WO | 2011103578 A1 | 8/2011 | |
| WO | 2011107592 A1 | 9/2011 | |
| WO | 2011109136 A2 | 9/2011 | |
| WO | 2011109400 A2 | 9/2011 | |
| WO | 2011145592 A1 | 11/2011 | |
| WO | 2012015362 A1 | 2/2012 | |
| WO | 2012129305 A1 | 9/2012 | |
| WO | 2012135194 | 10/2012 | |
| WO | WO2012135193 A2 | 10/2012 | ............ C08J 7/18 |
| WO | 2012159632 | 11/2012 | |
| WO | WO2014025949 A3 | 2/2014 | ............ A01N 59/20 |
| WO | 2014085379 | 6/2014 | |

OTHER PUBLICATIONS

Esteban-Tejeda et al. "Antibacterial and Antifungal Activity of a Soda-Lime Glass Containing Copper Nanoparticles," Nanotechnology 20 (2009) 505701 (6pp).

Esteban-Tejeda et al., "Glass-(nAg, nCu) Biocide Coatings on Ceramic Oxide Substrates." Plos One, Mar. 2012, vol. 7, Issue 3, p. 1-6.

Sherwin Williams Copper Bottom Anti-Fouling Paint #45—Protective and marine.

Bolshii Ya.Ya.' 'Mezhinskii G.Kh.' 'Sedmalis U.Ya.' 'Igaune S.A.', Izv.Akad.Nauk Latv.SSR,Ser.Khim., 1983, No. 2, p. 194.

Tretjakova N.I.' 'Mazurin 0.V.' , Vliyanie Okislov Dvukhvalentnykh Metallov na Vyazkost Prostykh Silikatnykh Stekol. Deposited in VINITI, Moscow, No. 995-69 Dep., 1969.

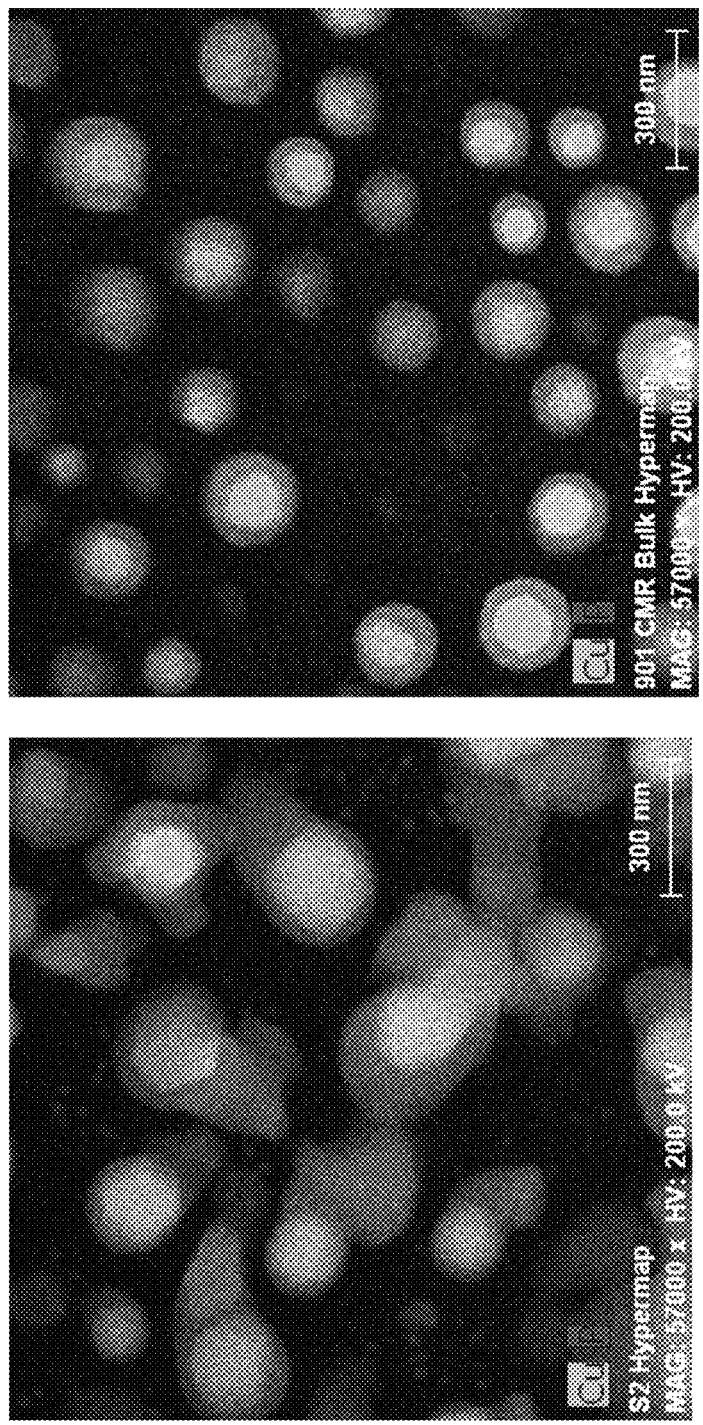

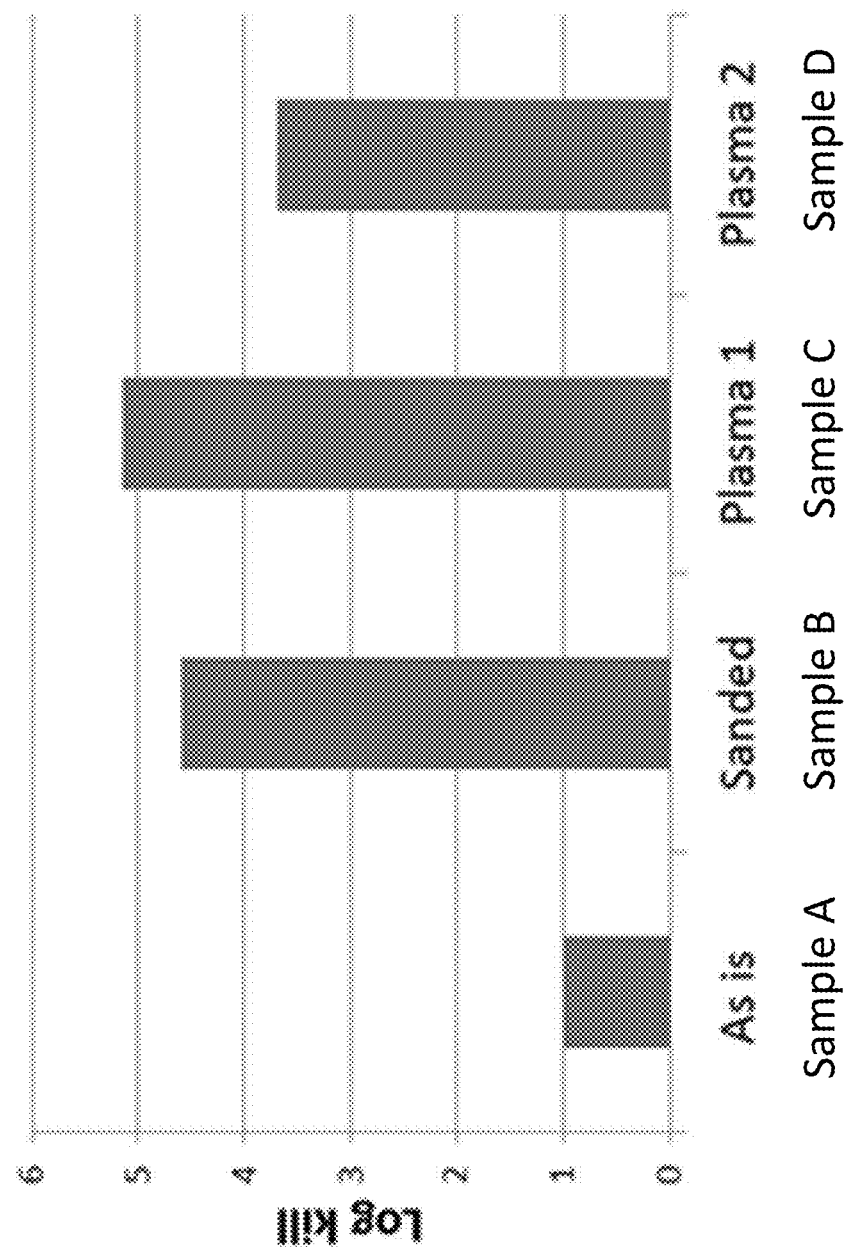

ANTIMICROBIAL GLASS COMPOSITIONS, GLASSES AND POLYMERIC ARTICLES INCORPORATING THE SAME

CROSS-REFERENCE TO RELATED APPLICATIONS

This application claims the benefit of priority under 35 U.S.C. §119 of U.S. Provisional Application Ser. No. 62/034,842 filed on Aug. 8, 2014, U.S. Provisional Application Ser. No. 62/034,834, filed Aug. 8, 2014, U.S. Provisional Application Ser. No. 62/026,186 filed on Jul. 18, 2014, U.S. Provisional Application Ser. No. 62/026,177, filed Jul. 18, 2014, U.S. Provisional Application Ser. No. 61/992,987 filed on May 14, 2014, U.S. Provisional Application Ser. No. 61/992,980, filed May 14, 2014, U.S. Provisional Application Ser. No. 61/941,690 filed on Feb. 19, 2014, and U.S. Provisional Application Ser. No. 61/941,677, filed Feb. 19, 2014, the content of which are relied upon and incorporated herein by reference in their entirety.

BACKGROUND

The present disclosure relates generally to antimicrobial glass compositions and articles incorporating such compositions. More particularly, the various embodiments described herein relate to glasses having antimicrobial attributes and articles that incorporate such glasses.

Consumer electronics articles, including touch-activated or touch-interactive devices, such as screen surfaces (e.g., surfaces of electronic devices having user-interactive capabilities that are activated by touching specific portions of the surfaces), have become increasingly more prevalent. As the extent to which the touch screen-based interactions between a user and a device increases, so too does the likelihood of the surface harboring microorganisms (e.g., bacteria, fungi, viruses, and the like) that can be transferred from user to user. Moreover, the housings which incorporate the touch-activated or touch-interactive devices also include surfaces that harbor such microorganisms that can be transferred from user to user. The concern of microorganism transfer is also a concern with equipment, furniture and architectural articles used in medical or office settings and many other articles in which users come into contact with surfaces.

To minimize the presence of microbes on various materials, so-called "antimicrobial" properties have been imparted to a variety of glasses; however, there is a need to provide entire articles (including the housing and any glasses used as cover glass) that also exhibit antimicrobial properties. Accordingly, antimicrobial articles useful for certain applications should be durable enough for the purpose for which they are used, while also providing continuous antimicrobial properties that are passive or do not require additional activation by a user or outside source (e.g., UV light). In addition, antimicrobial glasses and articles should provide controlled antimicrobial activity.

SUMMARY

A first aspect of the present disclosure pertains to an article that includes a carrier and a glass. Examples of suitable carriers include polymers, monomers, binders, solvents, and other materials used to form molded articles, formed articles, coatings on substrates or other such articles. Exemplary coatings may include anti-frictive coatings, coatings exhibiting a low coefficient of friction, or coatings that form a surface exhibiting a low coefficient of friction.

The glass of one or more embodiments may also include a composition that includes, in mole percent: $SiO_2$ in the range from about 40 to about 70, $Al_2O_3$ in the range from about 0 to about 20, a copper-containing oxide in the range from about 10 to about 50, CaO in the range from about 0 to about 15, MgO in the range from about 0 to about 15, $P_2O_5$ in the range from about 0 to about 25, $B_2O_3$ in the range from about 0 to about 25, $K_2O$ in the range from about 0 to about 20, ZnO in the range from about 0 to about 5, $Na_2O$ in the range from about 0 to about 20, and $Fe_2O_3$ in the range from about 0 to about 5. In some embodiments, the amount of copper-containing oxide is greater than the amount of $Al_2O_3$ (which may be about 5 mole percent or less, in some cases). In some instances, the composition may be free of $Al_2O_3$. Examples of suitable copper-containing oxides can include CuO, $Cu_2O$, or a combination thereof.

The article of one or more embodiments may include a plurality of $Cu^{1+}$ ions, Cu metal or a combination thereof. In some instances, the glass may be substantially free of tenorite.

The glass of one or more embodiments may include a cuprite phase and a glass phase. In some embodiments, the cuprite phase may include crystals that have an average major dimension of about 5 micrometers (μm) or less, or even about 1 micrometer (μm) or less.

A second aspect of the present disclosure pertains to an article that includes a carrier and a glass with a plurality of $Cu^{1+}$ ions, a degradable phase comprising at least one of $B_2O_3$, $P_2O_5$ and $R_2O$, and a durable phase comprising $SiO_2$. The glass may be formed from the compositions described herein. In some instances, the durable phase is present in an amount by weight that is greater than the degradable phase. The degradable phase of one or more embodiments leaches or is leachable in the presence of water.

The article may optionally include a cuprite phase, which may be dispersed in one or both of the degradable phase and the durable phase. The cuprite phase may have crystals having an average major dimension of about 5 micrometers (μm) or less, about 1 micrometer (μm) or less, or about 500 nanometers (nm) or less. The cuprite phase may comprise at least about 10 weight percent or at least about 20 weight percent of the glass.

In one or more embodiments, the glass includes a surface portion (having a depth of less than about 5 nanometers (nm)) that includes a plurality of copper ions. In some embodiments, at least 75% of the plurality of copper ions is $Cu^{1+}$. In other embodiments, less than about 25% of the plurality of copper ions is $Cu^{2+}$.

A third aspect of the present disclosure pertains to an article including a carrier; and an inorganic material, wherein the inorganic material comprises a surface and a plurality of $Cu^{1+}$ ions disposed on the surface. The inorganic material may include a glass and may be formed form the compositions described herein. The inorganic material may be substantially free of tenorite.

In one or more embodiments, the plurality of $Cu^{1+}$ ions may be dispersed in a glass network and/or a glass matrix. In some instances, the glass network includes atoms to which the plurality of $Cu^{1+}$ ions is atomically bonded. The plurality of ions may include cuprite crystals that are dispersed in the glass matrix.

The carrier may include a polymer, a monomer, a binder, a solvent, or combinations thereof. Carriers may include anti-frictive materials such as for example, fluorocarbons, fluorinated silanes, and alkyl perfluorocarbon silanes. The polymer used in the embodiments described herein can include organic or inorganic polymers. Exemplary polymers may include a thermoplastic polymer, a polyolefin, a cured polymer, an ultraviolet- or UV-cured polymer, a polymer emulsion, a solvent-based polymer, and combinations thereof. Specific examples of monomers include catalyst curable monomers, thermally-curable monomers, radiation-curable monomers and combinations thereof. The articles described herein may include a glass to carrier ratio in the range from about 10:90 to about 90:10, based on weight percent.

The glasses and articles described herein may exhibit a 2 log reduction or greater in a concentration of at least one of *Staphylococcus aureus, Enterobacter aerogenes, Pseudomonas aeruginosa* bacteria, Methicillin Resistant *Staphylococcus aureus*, and *E. coli*, under the EPA Test Method for Efficacy of Copper Alloy as a Sanitizer testing conditions (herein, after the "EPA Test").

The glasses and articles described herein according to one or more embodiments may exhibit a 4 log reduction or greater (e.g., 5 log reduction or greater) in a concentration of at least one of *Staphylococcus aureus, Enterobacter aerogenes, Pseudomonas aeruginosa* bacteria, Methicillin Resistant *Staphylococcus aureus*, and *E. coli*, under JIS Z 2801 (2000) testing conditions. One or more embodiments of the glasses and articles described herein also exhibit a 4 log reduction or greater (e.g., 5 log reduction or greater) in a concentration of at least one of *Staphylococcus aureus, Enterobacter aerogenes, Pseudomonas aeruginosa* Methicillin Resistant *Staphylococcus aureus*, and *E. coli*, under modified JIS Z 2801 (2000) testing conditions (hereinafter, "Modified JIS Z 2801 Test for Bacteria". The Modified JIS Z 2801 (2000) Test for Bacteria is described in greater detail herein.

In one or more embodiments, the glasses and articles described herein according to one or more embodiments may exhibit a 2 log reduction or greater (e.g., 4 log reduction or greater, or a 5 log reduction or greater) in a concentration of *Murine Norovirus*, under modified JIS Z 2801 (2000) testing conditions for evaluating viruses (hereinafter, "Modified JIS Z 2801 for Viruses"). The Modified JIS Z 2801 (2000) Test for Viruses is described in greater detail herein.

In some embodiments, the glasses and articles may exhibit the log reductions described herein (i.e., under the EPA Test, the JIS Z 2801 testing conditions, the Modified JIS Z 2801 Test for Bacteria and/or the Modified JIS Z 2801 Test for Viruses), for a period of one month or greater or for a period of three months or greater. The one month period or three month period may commence at or after the formation of the glass, or at or after combination of the glass with a carrier.

In one or more embodiments, the articles leach the copper ions when exposed or in contact with a leachate. In one or more embodiments, the articles leach only copper ions when exposed to leachates including water.

The articles described herein may form the housing for an electronic device.

A fourth aspect of the present disclosure pertains to a method of making an antimicrobial article. In one or more embodiments, the method includes melting a glass composition to form a glass comprising a plurality of $Cu^{1+}$ ions; and a glass phase, forming the glass into at least one of particulates and fibers, dispersing the at least one of particulates and fibers in a carrier, such as a polymer (as described herein), a monomer, or a binder, to provide a filled carrier and forming the filled carrier into the antimicrobial article. The glass composition may include the compositions described herein.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate one or more embodiment(s), and together with the description serve to explain principles and operation of the various embodiments.

BRIEF DESCRIPTION OF THE DRAWINGS

FIG. 7A is a SEM-energy-dispersive X-ray spectroscopy (EDX) hypermap of a cross-section of Example 30, after being annealed overnight at 650° C. after melting at 1650° C.;

FIG. 7B is a SEM-EDX hypermap of a cross-section of Example 30 after being quenched in water after melting at 1650° C.;

FIG. 15 shows the antimicrobial activity of injection molded articles, according to one or more embodiments, with and without different surface treatments.

DETAILED DESCRIPTION

Figure 1:
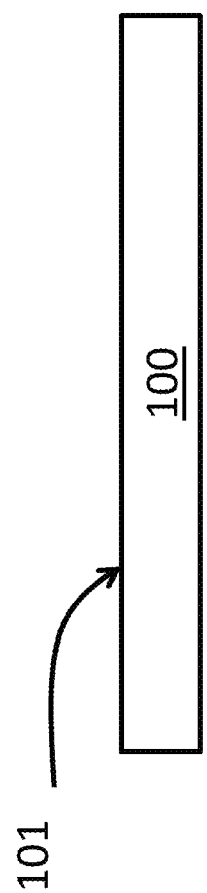
FIG. 1 is a side view of an antimicrobial glass in the form of a sheet according to one or more embodiments.

Reference will now be made in detail to various embodiment(s), examples of which are illustrated in the accompanying drawings.

A first aspect of the present disclosure pertains to antimicrobial glass compositions and glasses made from or including such compositions. The antimicrobial properties of the glasses disclosed herein include antiviral and/or antibacterial properties. As used herein the term "antimicrobial," means a material, or a surface of a material that will kill or inhibit the growth of bacteria, viruses and/or fungi. The term as used herein does not mean the material or the surface of the material will kill or inhibit the growth of all species microbes within such families, but that it will kill or inhibit the growth or one or more species of microbes from such families.

As used herein the term "log reduction" means–log $(C_d/C_0)$, where Ca=the colony form unit (CFU) number of the antimicrobial surface and $C_0$=the colony form unit (CFU) of the control surface that is not an antimicrobial surface. As an example, a 3 log reduction equals about 99.9% of the bacteria, viruses and/or fungi killed and a Log Reduction of 5=99.999% of bacteria, viruses and/or fungi killed.

In one or more embodiments, the antimicrobial glasses include a Cu species. In one or more alternative embodiments, the Cu species may include $Cu^{1+}$, $Cu^0$, and/or $Cu^{2+}$. The combined total of the Cu species may be about 10 wt % or more. However, as will be discussed in more detail below, the amount of $Cu^{2+}$ is minimized or is reduced such that the antimicrobial glass is substantially free of $Cu^{2+}$. The $Cu^{1+}$ ions may be present on or in the surface and/or the bulk of the antimicrobial glass. In some embodiments, the $Cu^{1+}$ ions are present in the glass network and/or the glass matrix of the antimicrobial glass. Where the $Cu^{1+}$ ions are present in the glass network, the $Cu^{1+}$ ions are atomically bonded to the atoms in the glass network. Where the $Cu^{1+}$ ions are present in the glass matrix, the $Cu^{1+}$ ions may be present in the form of $Cu^{1+}$ crystals that are dispersed in the glass matrix. In some embodiments the $Cu^{1+}$ crystals include cuprite $(Cu_2O)$. In such embodiments, where $Cu^{1+}$ crystals are present, the material may be referred to as an antimicrobial glass ceramic, which is intended to refer to a specific type of glass with crystals that may or may not be subjected to a traditional ceramming process by which one or more crystalline phases are introduced and/or generated in the glass. Where the $Cu^{1+}$ ions are present in a non-crystalline form, the material may be referred to as an antimicrobial glass. In some embodiments, both $Cu^{1+}$ crystals and $Cu^{1+}$ ions not associated with a crystal are present in the antimicrobial glasses described herein.

In one or more embodiments, the antimicrobial glass may be formed from a composition that can include, in mole percent, $SiO_2$ in the range from about 40 to about 70, $Al_2O_3$ in the range from about 0 to about 20, a copper-containing oxide in the range from about 10 to about 30, CaO in the range from about 0 to about 15, MgO in the range from about 0 to about 15, $P_2O_5$ in the range from about 0 to about 25, $B_2O_3$ in the range from about 0 to about 25, $K_2O$ in the range from about 0 to about 20, ZnO in the range from about 0 to about 5, $Na_2O$ in the range from about 0 to about 20, and/or $Fe_2O_3$ in the range from about 0 to about 5. In such embodiments, the amount of the copper-containing oxide is greater than the amount of $Al_2O_3$. In some embodiments, the composition may include a content of $R_2O$, where R may include K, Na, Li, Rb, Cs and combinations thereof.

In the embodiments of the compositions described herein, $SiO_2$ serves as the primary glass-forming oxide. The amount of $SiO_2$ present in a composition should be enough to provide glasses that exhibit the requisite chemical durability suitable for its use or application (e.g., touch applications, article housing etc.). The upper limit of $SiO_2$ may be selected to control the melting temperature of the compositions described herein. For example, excess $SiO_2$ could drive the melting temperature at 200 poise to high temperatures at which defects such as fining bubbles may appear or be generated during processing and in the resulting glass. Furthermore, compared to most oxides, $SiO_2$ decreases the compressive stress created by an ion exchange process of the resulting glass. In other words, glass formed from compositions with excess $SiO_2$ may not be ion-exchangeable to the same degree as glass formed from compositions without excess $SiO_2$. Additionally or alternatively, $SiO_2$ present in the compositions according to one or more embodiments could increase the plastic deformation prior break properties of the resulting glass. An increased $SiO_2$ content in the glass formed from the compositions described herein may also increase the indentation fracture threshold of the glass.

In one or more embodiments, the composition includes $SiO_2$ in an amount, in mole percent, in the range from about 40 to about 70, from about 40 to about 69, from about 40 to about 68, from about 40 to about 67, from about 40 to about 66, from about 40 to about 65, from about 40 to about 64, from about 40 to about 63, from about 40 to about 62, from about 40 to about 61, from about 40 to about 60, from about 41 to about 70, from about 42 to about 70, from about 43 to about 70, from about 44 to about 70, from about 45 to about 70, from about 46 to about 70, from about 47 to about 70, from about 48 to about 70, from about 49 to about 70, from about 50 to about 70, from about 41 to about 69, from about 42 to about 68, from about 43 to about 67 from about 44 to about 66 from about 45 to about 65, from about 46 to about 64, from about 47 to about 63, from about 48 to about 62, from about 49 to about 61, from about 50 to about 60 and all ranges and sub-ranges therebetween.

In one or more embodiments, the composition includes $Al_2O_3$ an amount, in mole percent, in the range from about 0 to about 20, from about 0 to about 19, from about 0 to about 18, from about 0 to about 17, from about 0 to about 16, from about 0 to about 15, from about 0 to about 14, from about 0 to about 13, from about 0 to about 12, from about 0 to about 11 from about 0 to about 10, from about 0 to about 9, from about 0 to about 8, from about 0 to about 7, from about 0 to about 6, from about 0 to about 5, from about 0 to about 4, from about 0 to about 3, from about 0 to about 2, from about 0 to about 1, from about 0.1 to about 1, from about 0.2 to about 1, from about 0.3 to about 1 from about 0.4 to about 1 from about 0.5 to about 1, from about 0 to about 0.5, from about 0 to about 0.4, from about 0 to about 0.3 from about 0 to about 0.2, from about 0 to about 0.1 and all ranges and sub-ranges therebetween. In some embodiments, the composition is substantially free of $Al_2O_3$. As used herein, the phrase "substantially free" with respect to the components of the composition and/or resulting glass means that the component is not actively or intentionally added to the compositions during initial batching or subsequent post processing (e.g., ion exchange process), but may be present as an impurity. For example, a composition, a glass may be describe as being substantially free of a component, when the component is present in an amount of less than about 0.01 mol %.

The amount of $Al_2O_3$ may be adjusted to serve as a glass-forming oxide and/or to control the viscosity of molten compositions. Without being bound by theory, it is believed that when the concentration of alkali oxide $(R_2O)$ in a composition is equal to or greater than the concentration of $Al_2O_3$, the aluminum ions are found in tetrahedral coordination with the alkali ions acting as charge-balancers. This tetrahedral coordination greatly enhances various post-processing (e.g., ion exchange process) of glasses formed from such compositions. Divalent cation oxides (RO) can also charge balance tetrahedral aluminum to various extents. While elements such as calcium, zinc, strontium, and barium behave equivalently to two alkali ions, the high field strength of magnesium ions causes them to not fully charge balance aluminum in tetrahedral coordination, resulting in the formation of five- and six-fold coordinated aluminum. Generally, $Al_2O_3$ can play an important role in ion-exchangeable compositions and strengthened glasses since it enables a strong network backbone (i.e., high strain point) while allowing for the relatively fast diffusivity of alkali ions. However, when the concentration of $Al_2O_3$ is too high, the composition may exhibit lower liquidus viscosity and, thus, $Al_2O_3$ concentration may be controlled within a reasonable range. Moreover, as will be discussed in more detail below, excess $Al_2O_3$ has been found to promote the formation of $Cu^{2+}$ ions, instead of the desired $Cu^{1+}$ ions.

In one or more embodiments, the composition includes a copper-containing oxide in an amount, in mole percent, in the range from about 10 to about 50, from about 10 to about 49, from about 10 to about 48, from about 10 to about 47, from about 10 to about 46, from about 10 to about 45, from about 10 to about 44, from about 10 to about 43, from about 10 to about 42, from about 10 to about 41, from about 10 to about 40, from about 10 to about 39, from about 10 to about 38, from about 10 to about 37, from about 10 to about 36, from about 10 to about 35, from about 10 to about 34, from about 10 to about 33, from about 10 to about 32, from about 10 to about 31, from about 10 to about 30, from about 10 to about 29, from about 10 to about 28, from about 10 to about 27, from about 10 to about 26, from about 10 to about 25, from about 10 to about 24, from about 10 to about 23, from about 10 to about 22, from about 10 to about 21, from about 10 to about 20, from about 11 to about 50, from about 12 to about 50, from about 13 to about 50, from about 14 to about 50, from about 15 to about 50, from about 16 to about 50, from about 17 to about 50, from about 18 to about 50, from about 19 to about 50, from about 20 to about 50, from about 10 to about 30, from about 11 to about 29, from about 12 to about 28, from about 13 to about 27, from about 14 to about 26, from about 15 to about 25, from about 16 to about 24, from about 17 to about 23, from about 18 to about 22, from about 19 to about 21 and all ranges and sub-ranges therebetween. In one or more specific embodiments, the copper-containing oxide may be present in the composition in an amount of about 20 mole percent, about 25 mole percent, about 30 mole percent or about 35 mole percent. The copper-containing oxide may include CuO, $Cu_2O$ and/or combinations thereof.

The copper-containing oxides in the composition form the $Cu^{1+}$ ions present in the resulting glass. Copper may be present in the composition and/or the glasses including the composition in various forms including $Cu^0$, $Cu^{1+}$ and $Cu^{2+}$. Copper in the $Cu^0$ or $Cu^{1+}$ forms provide antimicrobial activity. However forming and maintaining these states of antimicrobial copper are difficult and often, in known compositions, $Cu^{2+}$ ions are formed instead of the desired Cu0 or $Cu^{1+}$ ions.

In one or more embodiments, the amount of copper-containing oxide is greater than the amount of Al2O3 in the composition. Without being bound by theory it is believed that an about equal amount of copper-containing oxides and $Al_2O_3$ in the composition results in the formation of tenorite (CuO) instead of cuprite ($Cu_2O$). The presence of tenorite decreases the amount of $Cu^{1+}$ in favor of $Cu^{2+}$ and thus leads to reduced antimicrobial activity. Moreover, when the amount of copper-containing oxides is about equal to the amount of $Al_2O_3$, aluminum prefers to be in a four-fold coordination and the copper in the composition and resulting glass remains in the $Cu^{2+}$ form so that the charge remains balanced. Where the amount of copper-containing oxide exceeds the amount of $Al_2O_3$, then it is believed that at least a portion of the copper is free to remain in the $Cu^{1+}$ state, instead of the $Cu^{2+}$ state, and thus the presence of $Cu^{1+}$ ions increases.

The composition of one or more embodiments includes $P_2O_5$ in an amount, in mole percent, in the range from about 0 to about 25, from about 0 to about 22, from about 0 to about 20, from about 0 to about 18, from about 0 to about 16, from about 0 to about 15, from about 0 to about 14, from about 0 to about 13, from about 0 to about 12, from about 0 to about 11, from about 0 to about 10, from about 0 to about 9, from about 0 to about 8, from about 0 to about 7, from about 0 to about 6, from about 0 to about 5, from about 0 to about 4, from about 0 to about 3, from about 0 to about 2, from about 0 to about 1, from about 0.1 to about 1, from about 0.2 to about 1, from about 0.3 to about 1 from about 0.4 to about 1 from about 0.5 to about 1, from about 0 to about 0.5, from about 0 to about 0.4, from about 0 to about 0.3 from about 0 to about 0.2, from about 0 to about 0.1 and all ranges and sub-ranges therebetween. In some embodiments, the composition includes about 10 mole percent or about 5 mole percent $P_2O_5$ or, alternatively, may be substantially free of $P_2O_5$.

In one or more embodiments, $P_2O_5$ forms at least part of a less durable phase or a degradable phase in the glass. The relationship between the degradable phase(s) of the glass and antimicrobial activity is discussed in greater detail herein. In one or more embodiments, the amount of $P_2O_5$ may be adjusted to control crystallization of the composition and/or glass during forming. For example, when the amount of $P_2O_5$ is limited to about 5 mol % or less or even 10 mol % or less, crystallization may be minimized or controlled to be uniform. However, in some embodiments, the amount or uniformity of crystallization of the composition and/or glass may not be of concern and thus, the amount of $P_2O_5$ utilized in the composition may be greater than 10 mol %.

In one or more embodiments, the amount of $P_2O_5$ in the composition may be adjusted based on the desired damage resistance of the glass, despite the tendency for $P_2O_5$ to form a less durable phase or a degradable phase in the glass. Without being bound by theory, $P_2O_5$ can decrease the melting viscosity relative to $SiO_2$. In some instances, $P_2O_5$ is believed to help to suppress zircon breakdown viscosity (i.e., the viscosity at which zircon breaks down to form $ZrO_2$) and may be more effective in this regard than $SiO_2$. When glass is to be chemically strengthened via an ion exchange process, $P_2O_5$ can improve the diffusivity and decrease ion exchange times, when compared to other components that are sometimes characterized as network formers (e.g., $SiO_2$ and/or $B_2O_3$).

The composition of one or more embodiments includes $B_2O_3$ in an amount, in mole percent, in the range from about 0 to about 25, from about 0 to about 22, from about 0 to about 20, from about 0 to about 18, from about 0 to about 16, from about 0 to about 15, from about 0 to about 14, from about 0 to about 13, from about 0 to about 12, from about 0 to about 11, from about 0 to about 10, from about 0 to about 9, from about 0 to about 8, from about 0 to about 7, from about 0 to about 6, from about 0 to about 5, from about 0 to about 4, from about 0 to about 3, from about 0 to about 2, from about 0 to about 1, from about 0.1 to about 1, from about 0.2 to about 1, from about 0.3 to about 1 from about 0.4 to about 1 from about 0.5 to about 1, from about 0 to about 0.5, from about 0 to about 0.4, from about 0 to about 0.3 from about 0 to about 0.2, from about 0 to about 0.1 and all ranges and sub-ranges therebetween. In some embodiments, the composition includes a non-zero amount of $B_2O_3$, which may be, for example, about 10 mole percent or about 5 mole percent. The composition of some embodiments may be substantially free of $B_2O_3$.

In one or more embodiments, $B_2O_3$ forms a less durable phase or a degradable phase in the glass formed form the composition. The relationship between the degradable phase(s) of the glass and antimicrobial activity is discussed in greater detail herein. Without being bound by theory, it is believed the inclusion of $B_2O_3$ in compositions imparts damage resistance in glasses incorporating such compositions, despite the tendency for $B_2O_3$ to form a less durable phase or a degradable phase in the glass. The composition of one or more embodiments includes one or more alkali oxides ($R_2O$) (e.g., $Li_2O$, $Na_2O$, $K_2O$, $Rb_2O$ and/or $Cs_2O$). In some embodiments, the alkali oxides modify the melting temperature and/or liquidus temperatures of such compositions. In one or more embodiments, the amount of alkali oxides may be adjusted to provide a composition exhibiting a low melting temperature and/or a low liquidus temperature. Without being bound by theory, the addition of alkali oxide(s) may increase the coefficient of thermal expansion (CTE) and/or lower the chemical durability of the antimicrobial glasses that include such compositions. In some cases these attributes may be altered dramatically by the addition of alkali oxide(s).

In some embodiments, the antimicrobial glasses disclosed herein may be chemically strengthened via an ion exchange process in which the presence of a small amount of alkali oxide (such as $Li_2O$ and $Na_2O$) is required to facilitate ion exchange with larger alkali ions (e.g., $K^+$), for example exchanging smaller alkali ions from an antimicrobial glass with larger alkali ions from a molten salt bath containing such larger alkali ions. Three types of ion exchange can generally be carried out. One such ion exchange includes a $Na^+$-for-$Li^+$ exchange, which results in a deep depth of layer but low compressive stress. Another such ion exchange includes a $K^+$-for-$Li^+$ exchange, which results in a small depth of layer but a relatively large compressive stress. A third such ion exchange includes a $K^+$-for-$Na^+$ exchange, which results in intermediate depth of layer and compressive stress. A sufficiently high concentration of the small alkali oxide in compositions may be necessary to produce a large compressive stress in the antimicrobial glass including such compositions, since compressive stress is proportional to the number of alkali ions that are exchanged out of the antimicrobial glass.

In one or more embodiments, the composition includes $K_2O$ in an amount in the range from about 0 to about 20, from about 0 to about 18, from about 0 to about 16, from about 0 to about 15, from about 0 to about 14, from about 0 to about 13, from about 0 to about 12, from about 0 to about 11, from about 0 to about 10, from about 0 to about 9, from about 0 to about 8, from about 0 to about 7, from about 0 to about 6, from about 0 to about 5, from about 0 to about 4, from about 0 to about 3, from about 0 to about 2, from about 0 to about 1, from about 0.1 to about 1, from about 0.2 to about 1, from about 0.3 to about 1 from about 0.4 to about 1 from about 0.5 to about 1, from about 0 to about 0.5, from about 0 to about 0.4, from about 0 to about 0.3 from about 0 to about 0.2, from about 0 to about 0.1 and all ranges and sub-ranges therebetween. In some embodiments, the composition includes a non-zero amount of $K_2O$ or, alternatively, the composition may be substantially free, as defined herein, of $K_2O$. In addition to facilitating ion exchange, where applicable, in one or more embodiments, $K_2O$ can also form a less durable phase or a degradable phase in the glass formed form the composition. The relationship between the degradable phase(s) of the glass and antimicrobial activity is discussed in greater detail herein.

In one or more embodiments, the composition includes $Na_2O$ in an amount in the range from about 0 to about 20, from about 0 to about 18, from about 0 to about 16, from about 0 to about 15, from about 0 to about 14, from about 0 to about 13, from about 0 to about 12, from about 0 to about 11, from about 0 to about 10, from about 0 to about 9, from about 0 to about 8, from about 0 to about 7, from about 0 to about 6, from about 0 to about 5, from about 0 to about 4, from about 0 to about 3, from about 0 to about 2, from about 0 to about 1, from about 0.1 to about 1, from about 0.2 to about 1, from about 0.3 to about 1 from about 0.4 to about 1 from about 0.5 to about 1, from about 0 to about 0.5, from about 0 to about 0.4, from about 0 to about 0.3 from about 0 to about 0.2, from about 0 to about 0.1 and all ranges and sub-ranges therebetween. In some embodiments, the composition includes a non-zero amount of $Na_2O$ or, alternatively, the composition may be substantially free, as defined herein, of $Na_2O$.

In one or more embodiments, the composition may include one or more divalent cation oxides, such as alkaline earth oxides and/or ZnO. Such divalent cation oxides may be included to improve the melting behavior of the compositions. With respect to ion exchange performance, the presence of divalent cations can act to decrease alkali mobility and thus, when larger divalent cation oxides are utilized, there may be a negative effect on ion exchange performance. Furthermore, smaller divalent cation oxides generally help the compressive stress developed in an ion-exchanged glass more than the larger divalent cation oxides. Hence, divalent cation oxides such as MgO and ZnO can offer advantages with respect to improved stress relaxation, while minimizing the adverse effects on alkali diffusivity.

In one or more embodiments, the composition includes CaO in an amount, in mole percent, in the range from about 0 to about 15, from about 0 to about 14, from about 0 to about 13, from about 0 to about 12, from about 0 to about 11, from about 0 to about 10, from about 0 to about 9, from about 0 to about 8, from about 0 to about 7, from about 0 to about 6, from about 0 to about 5, from about 0 to about 4, from about 0 to about 3, from about 0 to about 2, from about 0 to about 1, from about 0.1 to about 1, from about 0.2 to about 1, from about 0.3 to about 1 from about 0.4 to about 1 from about 0.5 to about 1, from about 0 to about 0.5, from about 0 to about 0.4, from about 0 to about 0.3 from about 0 to about 0.2, from about 0 to about 0.1 and all ranges and sub-ranges therebetween. In some embodiments, the composition is substantially free of CaO.

In one or more embodiments, the composition includes MgO in an amount, in mole percent, in the range from about 0 to about 15, from about 0 to about 14, from about 0 to about 13, from about 0 to about 12, from about 0 to about 11, from about 0 to about 10, from about 0 to about 9, from about 0 to about 8, from about 0 to about 7, from about 0 to about 6, from about 0 to about 5, from about 0 to about 4, from about 0 to about 3, from about 0 to about 2, from about 0 to about 1, from about 0.1 to about 1, from about 0.2 to about 1, from about 0.3 to about 1 from about 0.4 to about 1 from about 0.5 to about 1, from about 0 to about 0.5, from about 0 to about 0.4, from about 0 to about 0.3 from about 0 to about 0.2, from about 0 to about 0.1 and all ranges and sub-ranges therebetween. In some embodiments, the composition is substantially free of MgO.

The composition of one or more embodiments may include ZnO in an amount, in mole percent, in the range from about 0 to about 5, from about 0 to about 4, from about 0 to about 3, from about 0 to about 2, from about 0 to about 1, from about 0.1 to about 1, from about 0.2 to about 1, from about 0.3 to about 1 from about 0.4 to about 1 from about 0.5 to about 1, from about 0 to about 0.5, from about 0 to about 0.4, from about 0 to about 0.3 from about 0 to about 0.2, from about 0 to about 0.1 and all ranges and sub-ranges therebetween. In some embodiments, the composition is substantially free of ZnO.

The composition of one or more embodiments may include $Fe_2O_3$, in mole percent, in the range from about 0 to about 5, from about 0 to about 4, from about 0 to about 3, from about 0 to about 2, from about 0 to about 1, from about 0.1 to about 1, from about 0.2 to about 1, from about 0.3 to about 1 from about 0.4 to about 1 from about 0.5 to about 1, from about 0 to about 0.5, from about 0 to about 0.4, from about 0 to about 0.3 from about 0 to about 0.2, from about 0 to about 0.1 and all ranges and sub-ranges therebetween. In some embodiments, the composition is substantially free of $Fe_2O_3$.

In one or more embodiments, the composition may include one or more colorants. Examples of such colorants include NiO, $TiO_2$, $Fe_2O_3$, $Cr_2O_3$, $Co_3O_4$ and other known colorants. In some embodiments, the one or more colorants may be present in an amount in the range up to about 10 mol %. In some instances, the one or more colorants may be present in an amount in the range from about 0.01 mol % to about 10 mol %, from about 1 mol % to about 10 mol %, from about 2 mol % to about 10 mol %, from about 5 mol % to about 10 mol %, from about 0.01 mol % to about 8 mol %, or from about 0.01 mol % to about 5 mol %.

In one or more embodiments, the composition may include one or more nucleating agents. Exemplary nucleating agents include $TiO_2$, $ZrO_2$ and other known nucleating agents in the art. The composition can include one or more different nucleating agents. The nucleating agent content of the composition may be in the range from about 0.01 mol % to about 1 mol %. In some instances, the nucleating agent content may be in the range from about 0.01 mol % to about 0.9 mol %, from about 0.01 mol % to about 0.8 mol %, from about 0.01 mol % to about 0.7 mol %, from about 0.01 mol % to about 0.6 mol %, from about 0.01 mol % to about 0.5 mol %, from about 0.05 mol % to about 1 mol %, from about 0.1 mol % to about 1 mol %, from about 0.2 mol % to about 1 mol %, from about 0.3 mol % to about 1 mol %, or from about 0.4 mol % to about 1 mol %, and all ranges and sub-ranges therebetween.

The glasses formed from the compositions may include a plurality of $Cu^{1+}$ ions. In some embodiments, such $Cu^{1+}$ ions form part of the glass network and may be characterized as a glass modifier. Without being bound by theory, where $Cu^{1+}$ ions are part of the glass network, it is believed that during typical glass formation processes, the cooling step of the molten glass occurs too rapidly to allow crystallization of the copper-containing oxide (e.g., CuO and/or $Cu_2O$). Thus the $Cu^{1+}$ remains in an amorphous state and becomes part of the glass network. In some cases, the total amount of $Cu^{1+}$ ions, whether they are in a crystalline phase or in the glass matrix, may be even higher, such as up to 40 mol %, up to 50 mol %, or up to 60 mol %.

In one or more embodiments, the glasses formed form the compositions disclosed herein include $Cu^{1+}$ ions that are dispersed in the glass matrix as $Cu^{1+}$ crystals. In one or more embodiments, the $Cu^{1+}$ crystals may be present in the form of cuprite. The cuprite present in the glass may form a phase that is distinct from the glass matrix or glass phase. In other embodiments, the cuprite may form part of or may be associated with one or more glasses phases (e.g., the durable phase described herein). The $Cu^{1+}$ crystals may have an average major dimension of about 5 micrometers (μm) or less, 4 micrometers (μm) or less, 3 micrometers (μm) or less, 2 micrometers (μm) or less, about 1.9 micrometers (μm) or less, about 1.8 micrometers (μm) or less, about 1.7 micrometers (μm) or less, about 1.6 micrometers (μm) or less, about 1.5 micrometers (am) or less, about 1.4 micrometers (μm) or less, about 1.3 micrometers (μm) or less, about 1.2 micrometers (μm) or less, about 1.1 micrometers or less, 1 micrometers or less, about 0.9 micrometers (μm) or less, about 0.8 micrometers (μm) or less, about 0.7 micrometers (μm) or less, about 0.6 micrometers (μm) or less, about 0.5 micrometers (μm) or less, about 0.4 micrometers (μm) or less, about 0.3 micrometers (μm) or less, about 0.2 micrometers (μm) or less, about 0.1 micrometers (μm) or less, about 0.05 micrometers (μm) or less, and all ranges and sub-ranges therebetween. As used herein and with respect to the phrase "average major dimension", the word "average" refers to a mean value and the word "major dimension" is the greatest dimension of the particle as measured by SEM. In some embodiments, the cuprite phase may be present in the antimicrobial glass in an amount of at least about 10 wt %, at least about 15 wt %, at least about 20 wt %, at least about 25 wt % and all ranges and subranges therebetween of the antimicrobial glass.

In some embodiments, the glasses may include about 70 wt % $Cu^{1+}$ or more and about 30 wt % of $Cu^{2+}$ or less. The $Cu^{2+}$ ions may be present in tenorite form and/or even in the glass (i.e., not as a crystalline phase).

In some embodiments, the total amount of Cu by wt % in the glasses may be in the range from about 10 to about 30, from about 15 to about 25, from about 11 to about 30, from about 12 to about 30, from about 13 to about 30, from about 14 to about 30, from about 15 to about 30, from about 16 to about 30, from about 17 to about 30, from about 18 to about 30, from about 19 to about 30, from about 20 to about 30, from about 10 to about 29, from about 10 to about 28, from about 10 to about 27, from about 10 to about 26, from about 10 to about 25, from about 10 to about 24, from about 10 to about 23, from about 10 to about 22, from about 10 to about 21, from about 10 to about 20, from about 16 to about 24, from about 17 to about 23, from about 18 to about 22, from about 19 to about 21 and all ranges and sub-ranges therebetween. In one or more embodiments, the ratio of $Cu^{1+}$ ions to the total amount Cu in the glass is about 0.5 or greater, 0.55 or greater, 0.6 or greater, 0.65 or greater, 0.7 or greater, 0.75 or greater, 0.8 or greater, 0.85 or greater, 0.9 or greater or even 1 or greater, and all ranges and sub-ranges therebetween. The amount of Cu and the ratio of $Cu^{1+}$ ions to total Cu may be determined by inductively coupled plasma (ICP) techniques known in the art.

In some embodiments, the glass may exhibit a greater amount of $Cu^{1+}$ and/or CuO than $Cu^{2+}$. For example, based on the total amount of $Cu^{1+}$, $Cu^{2+}$ and CuO in the glasses, the percentage of $Cu^{1+}$ and $Cu^0$, combined, may be in the range from about 50% to about 99.9%, from about 50% to about 99%, from about 50% to about 95%, from about 50% to about 90%, from about 55% to about 99.9%, from about 60% to about 99.9%, from about 65% to about 99.9%, from about 70% to about 99.9%, from about 75% to about 99.9%, from about 80% to about 99.9%, from about 85% to about 99.9%, from about 90% to about 99.9%, from about 95% to about 99.9%, and all ranges and sub-ranges therebetween. The relative amounts of $Cu^{1+}$, $Cu^{2+}$ and $Cu^0$ may be determined using x-ray photoluminescence spectroscopy (XPS) techniques known in the art. The tables below report these amounts as measured by XPS. Specifically, the tables report the amount of $Cu^{2+}$ and the combination of $Cu^{1+}$ and Cu0. Without being bound by theory, it is believed that most of the embodiments shown in Table 1 show copper as being present in the form of $Cu^{1+}$, under the conditions the XPS was performed.

The antimicrobial glass comprises at least a first phase and second phase. In one or more embodiments, the antimicrobial glass may include two or more phases wherein the phases differ based on the ability of the atomic bonds in the given phase to withstand interaction with a leachate. Specifically, the glass of one or more embodiments may include a first phase that may be described as a degradable phase and a second phase that may be described as a durable phase. The phrases "first phase" and "degradable phase" may be used interchangeably. The phrases "second phase" and "durable phase" may be used interchangeably. As used herein, the term "durable" refers to the tendency of the atomic bonds of the durable phase to remain intact during and after interaction with a leachate. As used herein, the term "degradable" refers to the tendency of the atomic bonds of the degradable phase to break during and after interaction with one or more leachates. In one or more embodiments, the durable phase includes $SiO_2$ and the degradable phase includes at least one of $B_2O_3$, $P_2O_5$ and $R_2O$ (where R can include any one or more of K, Na, Li, Rb, and Cs). Without being bound by theory, it is believed that the components of the degradable phase (i.e., $B_2O_3$, $P_2O_5$ and/or $R_2O$) more readily interact with a leachate and the bonds between these components to one another and to other components in the antimicrobial glass more readily break during and after the interaction with the leachate. Leachates may include water, acids or other similar materials. In one or more embodiments, the degradable phase withstands degradation for 1 week or longer, 1 month or longer, 3 months or longer, or even 6 months or longer. In some embodiments, longevity may be characterized as maintaining antimicrobial efficacy over a specific period of time.

In one or more embodiments, the durable phase is present in an amount by weight that is greater than the amount of the degradable phase. In some instances, the degradable phase forms islands and the durable phase forms the sea surrounding the islands (i.e., the durable phase). In one or more embodiments, either one or both of the durable phase and the degradable phase may include cuprite. The cuprite in such embodiments may be dispersed in the respective phase or in both phases.

In some embodiments, phase separation occurs without any additional heat treatment of the antimicrobial glass. In some embodiments, phase separation may occur during melting and may be present when the glass composition is melted at temperatures up to and including about 1600° C. or 1650° C. When the glass is cooled, the phase separation is maintained.

Figure 2:
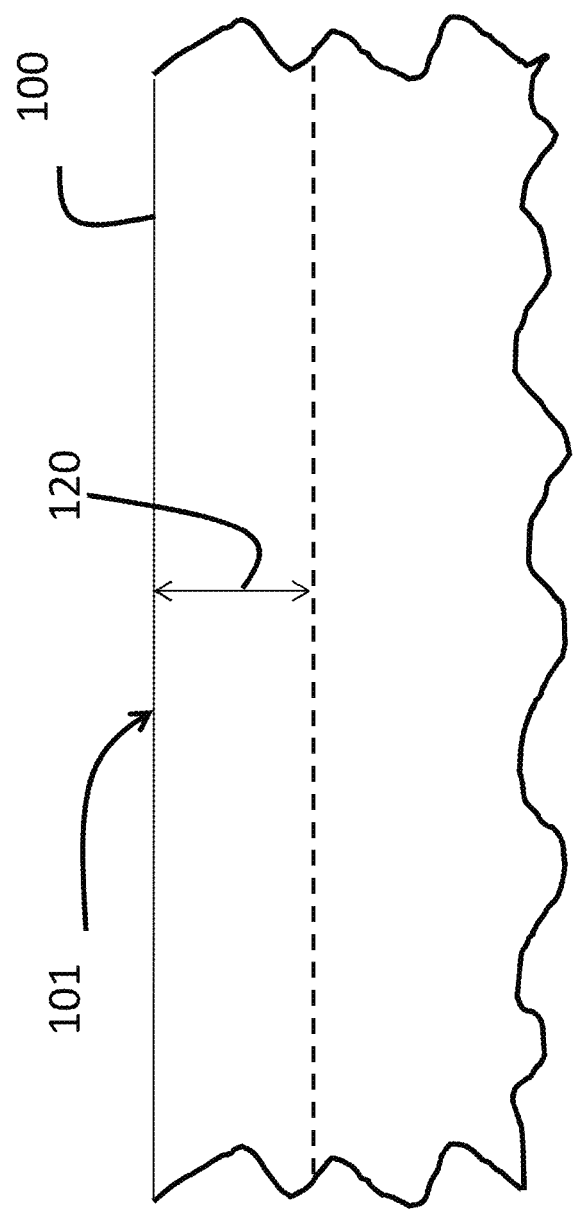
FIG. 2 is an enlarged partial view of the antimicrobial glass shown in FIG. 1.

The antimicrobial glass may be provided as a sheet or may have another shape such as particulate, fibrous, and the like. In one or more embodiments, as shown in FIGS. 1 and 2, the antimicrobial glass 100 includes a surface 101 and a surface portion 120 extending from the surface 101 into the antimicrobial glass at a depth of about 5 nanometers (nm) or less. The surface portion may include a plurality of copper ions wherein at least 75% of the plurality of copper ions includes $Cu^{1+}$-ions. For example, in some instances, at least about 80%, at least about 85%, at least about 90%, at least about 95%, at least about 98%, at least about 99% or at least about 99.9% of the plurality of copper ions in the surface portion includes $Cu^{1+}$ ions. In some embodiments, 25% or less (e.g., 20% or less, 15% or less, 12% or less, 10% or less or 8% or less) of the plurality of copper ions in the surface portion include $Cu^{2+}$ ions. For example, in some instances, 20% or less, 15% or less, 10% or less, 5% or less, 2% or less, 1% or less, 0.5% or less or 0.01% or less of the plurality of copper ions in the surface portion include $Cu^{2+}$ ions. In some embodiments, the surface concentration of $Cu^{1+}$ ions in the antimicrobial glass is controlled. In some instances, a $Cu^{1+}$ ion concentration of about 4 ppm or greater can be provided on the surface of the antimicrobial glass.

The antimicrobial glass of one or more embodiments may a 2 log reduction or greater (e.g., 2.5, 3, 3.5, 4, 4.5, 5, 5.5, 6, 6.5 and all ranges and sub-ranges therebetween) in a concentration of at least one of *Staphylococcus aureus, Enterobacter aerogenes, Pseudomonas aeruginosa*, Methicillin Resistant *Staphylococcus aureus*, and *E. coli*, under the EPA Test. In some instances, the antimicrobial glass exhibits at least a 4 log reduction, a 5 log reduction or even a 6 log reduction in the concentration of at least one of *Staphylococcus aureus, Enterobacter aerogenes, Pseudomonas aeruginosa* bacteria, Methicillin Resistant *Staphylococcus aureus*, and *E. coli* under the EPA Test.

The glasses described herein according to one or more embodiments may exhibit a 4 log reduction or greater (e.g., 5 log reduction or greater) in a concentration of at least one of *Staphylococcus aureus, Enterobacter aerogenes, Pseudomonas aeruginosa* bacteria, Methicillin Resistant *Staphylococcus aureus*, and *E. coli*, under JIS Z 2801 (2000) testing conditions. One or more embodiments of the glasses described herein also exhibit a 4 log reduction or greater (e.g., 5 log reduction or greater) in a concentration of at least one of *Staphylococcus aureus, Enterobacter aerogenes, Pseudomonas aeruginosa* Methicillin Resistant *Staphylococcus aureus*, and *E. coli*, under the Modified JIS Z 2801 Test for Bacterial. As used herein, Modified JIS Z 2801 Test for Bacteria includes evaluating the bacteria under the standard JIS Z 2801 (2000) test with modified conditions comprising heating the glass or article to a temperature of about 23 degrees Celsius to about 37 degrees Celsius at a humidity of about 38 percent to about 42 percent for about 6 hours.

In one or more embodiments described herein, the antimicrobial glasses exhibit a 2 log reduction or greater, a 3 log reduction or greater, a 4 log reduction or greater, or a 5 log reduction or greater in *Murine Norovirus* under a Modified JIS Z 2801 for Viruses test. The Modified JIS Z 2801 (2000) Test for Viruses includes the following procedure. For each material (e.g., the articles or glass of one or more embodiments, control materials, and any comparative glasses or articles) to be tested, three samples of the material (contained in individual sterile petri dishes) are each inoculated with a 20 μL aliquot of a test virus (where antimicrobial activity is measured) or a test medium including an organic soil load of 5% fetal bovine serum with or without the test virus (where cytotoxicity is measured). The inoculum is then covered with a film and the film is pressed down so the test virus and/or or test medium spreads over the film, but does not spread past the edge of the film. The exposure time begins when each sample was inoculated. The inoculated samples are transferred to a control chamber set to room temperature (about 20° C.) in a relative humidity of 42% for 2 hours. Exposure time with respect to control samples are discussed below. Following the 2-hour exposure time, the film is lifted off using sterile forceps and a 2.00 mL aliquot of the text virus and/or test medium is pipetted individually onto each sample of material and the underside of the film (or the side of the film exposed to the sample) used to cover each sample. The surface of each sample is individually scrapped with a sterile plastic cell scraper to collect the test virus or test medium. The test virus and/or test medium is collected (at $10^{-2}$ dilution), mixed using a vortex type mixer and serial 10-fold dilutions are prepared. The dilutions are then assayed for antimicrobial activity and/or cytotoxicity.

To prepare a control sample for testing antimicrobial activity (which are also referred to as "zero-time virus controls") for the Modified JIS Z 2801 Test for Viruses, three control samples (contained in individual sterile petri dishes) are each inoculated with a 20 μL aliquot of the test virus. Immediately following inoculation, a 2.00 mL aliquot of test virus is pipetted onto each control sample. The surface of each sample was individually scrapped with a sterile plastic cell scraper to collect test virus. The test virus is collected (at $10^{-2}$ dilution), mixed using a vortex type mixer, and serial 10-fold dilutions were prepared. The dilutions are assayed for antimicrobial activity.

To prepare controls samples for cytotoxicity (which are also referred to as "2 hour control virus") for the Modified JIS Z 2801 Test for Viruses, one control sample (contained in an individual sterile petri dish) is inoculated with a 20 μL aliquot of a test medium containing an organic soil load (5% fetal bovine serum), without the test virus. The inoculum is covered with a film and the film is pressed so the test medium spreads over the film but does not spread past the edge of the film. The exposure time begins when each control sample is inoculated. The control sample is transferred to a controlled chamber set to room temperature (20° C.) in a relative humidity of 42% for a duration of 2 hours exposure time. Following this exposure time, the film is lifted off using sterile forceps and a 2.00 mL aliquot of the test medium is pipetted individually onto each control sample and the underside of the film (the side exposed to the sample). The surface of each sample is individually scrapped with a sterile plastic cell scraper to collect the test medium. The test medium is collected (at $10^{-2}$ dilution), mixed using a vortex type mixer, and serial 10-fold dilutions were prepared. The dilutions were assayed for cytotoxicity.

The antimicrobial glass of one or more embodiments may exhibit the log reduction described herein for long periods of time. In other words, the antimicrobial glass may exhibit extended or prolonged antimicrobial efficacy. For example, in some embodiments, the antimicrobial glass may exhibit the log reductions described herein under the EPA Test, the JIS Z 2801 (2000) testing conditions, the Modified JIS Z 2801 Test for Bacteria and/or the Modified JIS Z 2801 Test for Viruses for up to 1 month, up to 3 months, up to 6 months or up to 12 months after the antimicrobial glass is formed or after the antimicrobial glass is combined with a carrier (e.g., polymers, monomers, binders, solvents and the like). These time periods may start at or after the antimicrobial glass is formed or combined with a carrier.

One or more embodiments, the antimicrobial glass may exhibit a preservative function, when combined with carriers described herein. In such embodiments, the antimicrobial glass may kill or eliminate, or reduce the growth of various foulants in the carrier. Foulants include fungi, bacteria, viruses and combinations thereof.

In one or more embodiments, the glasses and/or articles described herein leach the copper ions when exposed or in contact with a leachate. In one or more embodiments, the glass leaches only copper ions when exposed to leachates including water.

In one or more embodiments, the antimicrobial glass and/or articles described herein may have a tunable antimicrobial activity release. The antimicrobial activity of the glass and/or articles may be caused by contact between the antimicrobial glass and a leachate, such as water, where the leachate causes $Cu^{1+}$ ions to be released from the antimicrobial glass. This action may be described as water solubility and the water solubility can be tuned to control the release of the Cu+1 ions.

In some embodiments, where the $Cu^{1+}$ ions are disposed in the glass network and/or form atomic bonds with the atoms in the glass network, water or humidity breaks those bonds and the $Cu^{1+}$ ions available for release and may be exposed on the glass or glass ceramic surface.

In one or more embodiments, the antimicrobial glass may be formed using formed in low cost melting tanks that are typically used for melting glass compositions such as soda lime silicate. The antimicrobial glass may be formed into a sheet using forming processes known in the art. For instance, example forming methods include float glass processes and down-draw processes such as fusion draw and slot draw.

The antimicrobial glass may be incorporated into a variety of articles, either alone or in combination with other materials, such as electronic devices (e.g., mobile phones, smart phones, tablets, video players, information terminal devices, laptop computer, etc.), architectural structures (e.g., countertops or walls), appliances (e.g., cooktops, refrigerator and dishwasher doors, etc.), information displays (e.g., whiteboards), and automotive components (e.g., dashboard panels, windshields, window components, etc.). When used in such articles, the antimicrobial glass can form at least part of the housing and/or display.

After formation, the antimicrobial glass may be formed into sheets and may be shaped, polished or otherwise processed for a desired end use. In some instances, the antimicrobial glass may be ground to a powder or particulate form. In other embodiments, the particulate antimicrobial glass may be combined with other materials or carriers into articles for various end uses. The combination of the antimicrobial glass and such other materials or carriers may be suitable for injection molding, extrusion or coatings or may be drawn into fibers. Such other materials or carriers may include polymers, monomers, binders, solvents, or a combination thereof as described herein. The polymer used in the embodiments described herein can include a thermoplastic polymer, a polyolefin, a cured polymer, an ultraviolet- or UV-cured polymer, a polymer emulsion, a solvent-based polymer, and combinations thereof. Examples of suitable polymers include, without limitation: thermoplastics including polystyrene (PS), high impact PS, polycarbonate (PC), nylon (sometimes referred to as polyamide (PA)), poly(acrylonitrile-butadiene-styrene) (ABS), PC-ABS blends, polybutyleneterephthlate (PBT) and PBT co-polymers, polyethyleneterephthalate (PET) and PET co-polymers, polyolefins (PO) including polyethylenes (PE), polypropylenes (PP), cyclicpolyolefins (cyclic-PO), modified polyphenylene oxide (mPPO), polyvinylchloride (PVC), acrylic polymers including polymethyl methacrylate (PMMA), thermoplastic elastomers (TPE), thermoplastic urethanes (TPU), polyetherimide (PEl) and blends of these polymers with each other. Suitable injection moldable thermosetting polymers include epoxy, acrylic, styrenic, phenolic, melamine, urethanes, polyesters and silicone resins. In other embodiments, the polymers may be dissolved in a solvent or dispersed as a separate phase in a solvent and form a polymer emulsion, such as a latex (which is a water emulsion of a synthetic or natural rubber, or plastic obtained by polymerization and used especially in coatings (as paint) and adhesives. Polymers may include fluorinated silanes or other low friction or anti-frictive materials. The polymers can contain impact modifiers, flame retardants, UV inhibitors, antistatic agents, mold release agents, fillers including glass, metal or carbon fibers or particles (including spheres), talc, clay or mica and colorants. Specific examples of monomers include catalyst curable monomers, thermally-curable monomers, radiation-curable monomers and combinations thereof.

In one example, acrylic latex paint may be combined with 20 wt % antimicrobial glass in particulate form and having a diameter of about 5 micrometers (μm). In some embodiments, the resulting combination of paint and antimicrobial glass included about 4 wt % CuO. In one or more embodiments, when combined with a carrier such as a polymer, monomer, binder or solvent, the amount of antimicrobial glass may be in the range from about 50 wt % to about 85 wt %. In some embodiments, the antimicrobial glass may be present in an amount in the range from about 55 wt % to about 85 wt %, from about 60 wt % to about 85 wt %, from about 65 wt % to about 85 wt %, from about 50 wt % to about 80 wt %, from about 50 wt % to about 75 wt %, from about 50 wt % to about 70 wt % and all ranges and sub-ranges therebetween, based on the total weight of the antimicrobial glass and carrier. In such embodiments, the total amount of CuO present in the may be about 20 wt %. In other embodiments, the amount of $Cu_2O$ present in the antimicrobial glass and carrier combination may be in the range from about 10 wt % to about 20 wt % or more specifically, about 15%. The ratio of antimicrobial glass to carrier, by vol %, may be in the range from about 90:10 to about 10:90, or more specifically about 50:50.

In one or more embodiments, the antimicrobial glass may be provided in particulate form and may have a diameter in the range from about 0.1 micrometers (μm) (μm) to about 10 micrometers (μm) (μm), from about 0.1 micrometers (μm) (μm) to about 9 micrometers (μm) (μm), from about 0.1 micrometers (μm) (μm) to about 8 micrometers (μm) (μm), from about 0.1 micrometers (μm) (μm) to about 7 micrometers (μm) (μm), from about 0.1 micrometers (μm) (μm) to about 6 micrometers (μm) (μm), from about 0.5 micrometers (μm) (μm) to about 10 micrometers (μm) (μm), from about 0.75 micrometers (μm) (μm) to about 10 micrometers (μm) (μm), from about 1 micrometers (μm) (μm) to about 10 micrometers (μm) (μm), from about 2 micrometers (μm) (μm) to about 10 micrometers (μm) (μm), from about 3 micrometers (μm) (μm) to about 10 micrometers (μm) (μm) from about 3 micrometers (μm) (μm) to about 6 micrometers (μm) (μm), from about 3.5 micrometers (μm) (μm) to about 5.5 micrometers (μm) (μm), from about 4 micrometers (μm) (μm), to about 5 micrometers (μm) (μm), and all ranges and sub-ranges therebetween. The particulate antimicrobial glass may be substantially spherical or may have an irregular shape. The particles may be provided in a solvent and thereafter dispersed in a carrier as otherwise described herein.

Without being bound by theory it is believed that the combination of the antimicrobial glass described herein and a carrier, such as latex paint, provides substantially greater antimicrobial efficacy as compared to the same latex paint that includes only $Cu_2O$ (cuprite), even when the same amount of copper is utilized. The presence of $Cu^{1+}$ crystals in the antimicrobial glasses described herein, even when present as cuprite, tends to remain in the $Cu^{1+}$ state. Without being bound by theory, it is believed that when $Cu_2O$ is provided alone, separate from the glasses described herein, the Cu ions are less stable and may change to $Cu^{2+}$ from $Cu^{1+}$.

The antimicrobial performance of the articles described herein may be impacted by the presence of a thin layer of polymer on the surface of the article. This thin layer may exhibit hydrophobic properties and may block the active copper species ($Cu^{1+}$) from exposure to air or from leaching to the surface. In one or more embodiments, the articles may use polymers that have balanced hydrophobic-hydrophilic properties that facilitate leaching of the active copper species. Examples of such polymers include hygroscopic/water soluble polymers and surfactants, amphiphilic polymers and/or a combination of amphiphilic polymers and hygroscopic materials. In one or more embodiments, the exposure to air and/or leaching of the active copper species to the surface may be facilitated by providing articles with an exposed treated surface. In one or more embodiments, the exposed treated surface is a surface that has been mechanically or chemically treated to expose at least some of the glass contained in the article to the air or to provide some of the glass at the surface of the article. Specific methods for providing an exposed treated surface include sanding, polishing, plasma treating (e.g., air, $N_2$, $O_2$, $H_2$, $N_2$ and/or Argon based plasma) and other methods that will remove a thin layer of the polymer material. In one or more alternative embodiments, the exposed treated surface includes functional groups, particularly hydroxyl and carbonyl groups, which are introduced into or to the exposed treated surface, to make such surface more hydrophilic. By providing an exposed treated surface, the active copper species is exposed to air or more readily leaches the surface of the article.

To improve processability, mechanical properties and interactions between the polymer and the glass described herein (including any fillers and/or additives that may be used), processing agents/aids may be included in the articles described herein. Exemplary processing agents/aids can include solid or liquid materials. The processing agents/aids may provide various extrusion benefits, and may include silicone based oil, wax and free flowing fluoropolymer. In other embodiments, the processing agents/aids may include compatibilizers/coupling agents, e.g., organosilicon compounds such as organo-silanes/siloxanes that are typically used in processing of polymer composites for improving mechanical and thermal properties. Such compatibilizers/coupling agents can be used to surface modify the glass and can include (3-acryloxy-propyl)trimethoxysilane; N-(2-aminoethyl)-3-aminopropyltrimethoxysilane; 3-aminopropyltri-ethoxysilane; 3-aminopropyltrimethoxysilane; (3-glycidoxypropyl)trimethoxysilane; 3-mercaptopropyltrimethoxysilane; 3-methacryloxypropyltrimethoxysilane; and vinyltrimethoxysilane.

In some embodiments, the articles described herein may include fillers including pigments, that are typically metal based inorganics can also be added for color and other purposes, e.g., aluminum pigments, copper pigments, cobalt pigments, manganese pigments, iron pigments, titanium pigments, tin pigments, clay earth pigments (naturally formed iron oxides), carbon pigments, antimony pigments, barium pigments, and zinc pigments.

After combining the antimicrobial glass described herein with a carrier, as described herein, the combination may be formed into a desired article. Examples of such articles include housings for electronic devices (e.g., mobile phones, smart phones, tablets, video players, information terminal devices, laptop computer, etc.), architectural structures (e.g., countertops or walls), appliances (e.g., cooktops, refrigerator and dishwasher doors, etc.), information displays (e.g., whiteboards), and automotive components (e.g., dashboard panels, windshields, window components, etc.).

In one or more embodiments, the articles may exhibit desired porosity and may be made into different shapes, including complex shapes and in different forms including plastics, rubbers and fiber/fabrics, which can have the same or different applications. Porous articles can also be used as antimicrobial filters. For example, the articles may be extruded into a honeycomb structure, which not only includes channels but also porous channel walls.

In other embodiments, the articles may include a high glass loading. Such articles may be formed from a melting process or the wet process. In such embodiments, in addition to using the articles themselves as an antimicrobial material, the polymer can be burnt out or removed to provide a pure copper glass antimicrobial article that is porous, with a simple or complex shape.

Cu(I) is an excellent catalyst for organic reactions, particularly for mild organic reactions, such as polymerization of acrylic monomers and oleochemical applications (e.g., hydrogenolysis of fatty esters to fatty alcohols including both methyl ester and wax ester processes, alkylation of alcohols with amines and amination of fatty alcohols), just to name a few. The articles described herein may be used for such applications.

Figure 13:
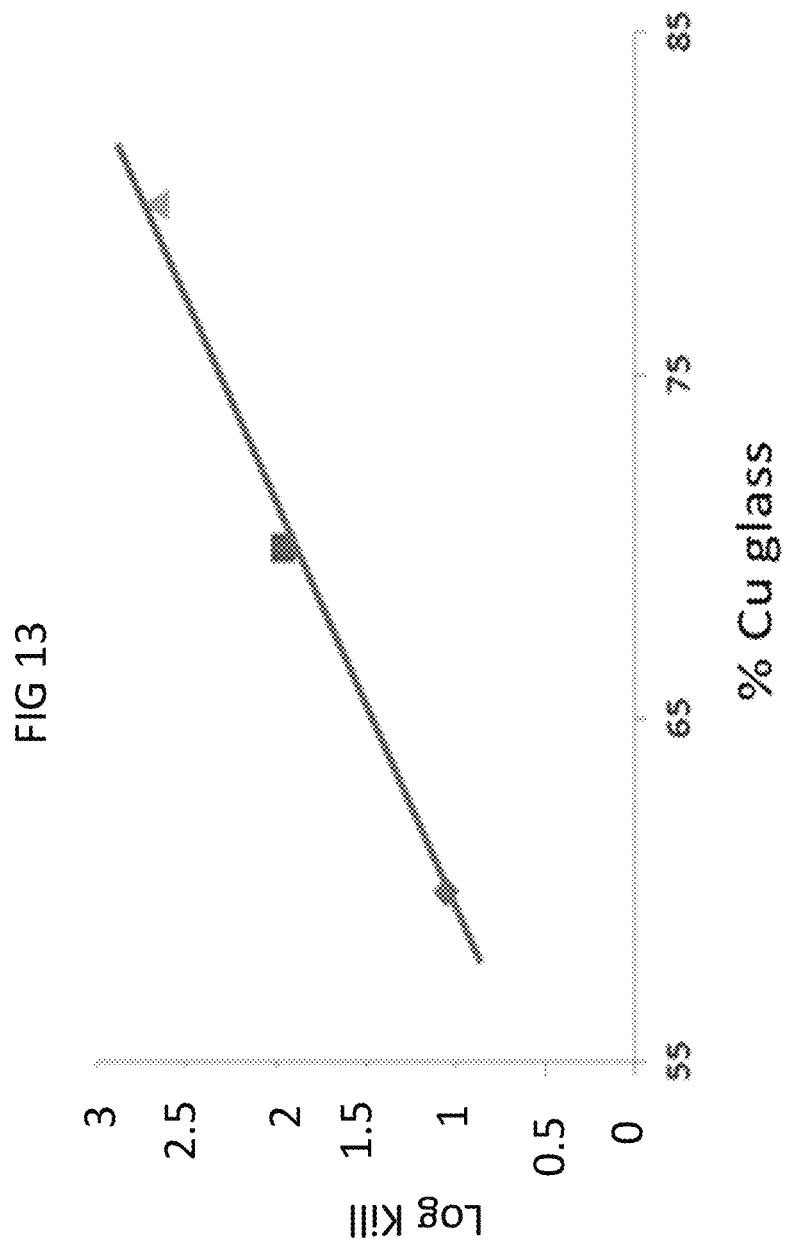
FIG. 13 is a graph illustrating the antimicrobial activity of glasses having different amounts of copper.

Examples of the various uses and application of the articles described herein are shown in FIG. 13.

The articles described herein, including the antimicrobial glass and a polymer, may exhibit a 2 log reduction or greater in a concentration of at least one of *Staphylococcus aureus, Enterobacter aerogenes, Pseudomonas aeruginosa* bacteria, Methicillin Resistant *Staphylococcus aureus*, and *E. coli*, under the EPA Test. In some instances, the article exhibits at least a 4 log reduction, a 5 log reduction or even a 6 log reduction in the concentration of at least one of *Staphylococcus aureus, Enterobacter aerogenes, Pseudomonas aeruginosa* bacteria, Methicillin Resistant *Staphylococcus aureus*, and *E. coli* under the EPA Test.

The articles described herein according to one or more embodiments may exhibit a 2 log reduction or greater (e.g., 3 log reduction or greater, 4 log reduction or greater, or 5 log reduction or greater) in a concentration of at least one of *Staphylococcus aureus, Enterobacter aerogenes, Pseudomonas aeruginosa* bacteria, Methicillin Resistant *Staphylococcus aureus*, and *E. coli*, under the JIS Z 2801 (2000) testing conditions and/or the Modified JIS Z 2801 Test for Bacteria. One or more embodiments of the articles described herein also exhibit a 4 log reduction or greater (e.g., 5 log reduction or greater) in a concentration of *Murine Norovirus* (strain MNV-1), under the Modified JIS Z 2801 Test for Viruses.

The articles of one or more embodiments may exhibit the log reduction described herein for long periods of time. In other words, the article may exhibit extended or prolonged antimicrobial efficacy. For example, in some embodiments, the article may exhibit the log reductions in bacteria and/or viruses described herein for up to 1 month, up to 3 months, up to 6 months or up to 12 months after the antimicrobial glass is formed or after the antimicrobial glass is combined with a carrier. These time periods may start at or after the antimicrobial glass is formed or combined with a carrier.

In one or more embodiments, the article may include a coating that may be applied on a surface, forming a coated surface. The coated surface may exhibit a stable color that does not undergo substantial changes after exposure to specific environments. For example, the coated surface may exhibit a delta ($\Delta$) E of less than about 2 or even less than about 1, as measured by ASTM D2247, after being exposed to a temperature of 38° C. at 100% relative humidity for 7 days. As used herein, the phrase "delta (A) E" refers to the total color distance as measured by the distance between two color coordinates, provided under the CIELAB color space ($\Delta E^*_{ab} = \sqrt{(L_2^* - L_1^*)^2 + (a_2^* - a_1^*)^2 + (b_2^* - b_1^*)^2}$).

The coated surface may also exhibit chemical resistance to various chemicals, as measured by ASTM D1308, after exposure to chemicals in the center of a test piece for 1 hour.

The articles described herein may include pigments to impart color. Accordingly, the coatings made from such articles may exhibit a wide variety of colors, depending on the carrier color, mixture of carriers and amount of particle loading. Moreover, the articles and/or coatings described herein showed no adverse effect to paint adhesion as measured by ASTM D4541. In some instances, the adhesion of the article or coating to an underlying substrate was greater than the cohesive strength of the substrate. In other words, in testing, the adhesion between the coating and the substrate was so strong that the underlying substrate failed before the coating was separated from the surface of the substrate. For example, where the substrate includes wood, the adhesion between the coating and the substrate may be about 300 psi or greater, 400 psi or greater, 500 psi or greater, 600 psi or greater and all ranges-sub-ranges therebetween, as measured by ASTM D4541. In some instances, the article, when applied to a substrate as a coating, exhibits an anti-sag index value of about 3 or greater, about 5 or greater, 7 or greater, 8 or greater, 9 or greater, 10 or greater, 11 or greater, 12 or greater, 13 or greater, 14 or greater or even 15 or greater, as measured by ASTM D4400.

The article and/or coating may exhibit sufficient durability for use in household and commercial applications. Specifically, the article, when applied to a substrate as a coating, exhibits a scrub resistance as measured by ASTM D4213 of about 4 or greater, 5 or greater, 6 or greater, 7 or greater and all ranges and sub-ranges therebetween.

In one or more embodiments, the article and/or coating may be resistant to moisture. For example, after exposure of the article and/or coating to an environment of up to about 95% relative humidity for 24 hours, the article and/or coating exhibited no change in antimicrobial activity.

One or more embodiments of the article may include an antimicrobial glass and a carrier with a loading level of the antimicrobial glass such that the article exhibits resistance or preservation against the presence or growth of foulants. Foulants include fungi, bacteria, viruses and combinations thereof. In some instances, the presence or growth of foulants in articles, such as paints, varnishes and the like, can cause color changes to the article, can degrade the integrity of the article and negatively affect various properties of the article. By including a minimum loading of antimicrobial glass, (e.g., about 5 wt % or less, about 4 wt % or less, about 3 wt % or less, about 2 wt % or less, or about 1 wt % or less) to the carrier, the foulants can be eliminated or reduced. In some instances, the carrier formulation need not include certain components, when fouling is eliminated or reduced. Thus, the carrier formulations used in one or more embodiments of the articles described herein may have more flexibility and variations than previously possible, when in known articles that do not include the antimicrobial glass.

Another aspect of this disclosure pertains to a method of making an antimicrobial article. In one or more embodiments, the method includes melting a glass composition (such as the compositions disclosed herein) to form a glass, forming the glass into particles, fibers or a combination thereof, dispersing the particles and/or fibers into a carrier (e.g., polymer) to provide a filled polymer and forming the filled polymer into an antimicrobial article.

In one or more embodiments, method includes loading a selected amount of glass into the polymer, depending on the application of the article. Various methods and processes can be used to such as, for example, an in situ process through mixing monomers with the glass (which may be ground into particles or other form) and then polymerized (into a thermosetting or a thermoplastic polymer matrix) or by mixing polymer with the glass through a process of solution or melt compounding (e.g. using a Brabender compounder or an extruder, single screw or twin screw, reactive or non-reactive), etc.

In one or more embodiments, forming the filled polymer into the antimicrobial article may include extruding or molding the filled polymer. In one or more embodiments, the antimicrobial article may be further processed to expose at least a portion of the glass to an exterior surface. The exterior surface may be a surface with which the user of the antimicrobial article interacts (e.g., the exterior surface of a mobile phone, the display of the mobile phone etc.). In one or more embodiments, the method may include removing a surface portion of the antimicrobial article to expose the glass dispersed in the filled polymer. Exemplary methods of removing a surface portion of the antimicrobial article may include etching (by plasma, acid or mechanical means such as sanding or polishing).

EXAMPLES

Various embodiments will be further clarified by the following examples.

Examples 1-62

Non-limiting examples of compositions described herein are listed in Table 1. The compositions in Table 1 were batched, melted and formed into glasses. Table 2 lists selected properties of the compositions of Table 1 and/or glasses formed therefrom, including the conditions for melting, annealing, appearance of the melt, density, anneal point (as measured by Beam Bending Viscometer (BBV)), strain point (as measured by BBV), softening point (as measured by parallel plate viscometer (PPV)), Vickers hardness, Vickers crack initiation, fracture toughness by chevron notch, coefficient of thermal expansion and the and other properties. Table 2 also includes the weight percent of Cu oxides, as determined by ICP techniques, and the ratio of $Cu^{1+}:Cu^{2+}$ for selected glasses.

Table 3 includes information related to the crystalline phases of crystal phase assemblages and/or crystal sizes of selected glasses as determined using X-ray diffraction (XRD) techniques known to those in the art, using such commercially available equipment as the model as a PW1830 (Cu Kα radiation) diffractometer manufactured by Philips, Netherlands. Spectra were typically acquired for from 5 to 80 degrees. Table 3 also includes elemental profile information of selected glasses determined XPS techniques.

The glasses where then tested under the EPA test using *Staphylococcus aureus* under two conditions, as shown in Table 4. Table 4 also includes the total amount of Cu and $Cu^{1+}$ found in selected examples, as determined by ICP techniques.

TABLE 1

Table 1

| Example | Ex. 1 | Ex. 2 | Ex. 3 | Ex. 4 | Ex. 5 |
|---|---|---|---|---|---|
| Batched Composition (mol %) | | | | | |
| $SiO_2$ | 65 | 65 | 60 | 60 | 60 |
| $Al_2O_3$ | 17.5 | 17.5 | 20 | 15 | 15 |
| CuO | 17.5 | 17.5 | 20 | 20 | 20 |
| $Na_2O$ | | | | 5 | |
| $K_2O$ | | | | | 5 |
| $B_2O_3$ | | | | | |
| $P_2O_5$ | | | | | |
| ZnO | | | | | |
| Batched Composition (wt %) | | | | | |
| $SiO_2$ | 55.2 | 55.2 | 49.8 | 51.2 | 50.1 |
| $Al_2O_3$ | 25.2 | 25.2 | 28.2 | 21.7 | 21.3 |
| CuO | 19.7 | 19.7 | 22.0 | 22.6 | 22.1 |
| $Na_2O$ | | | | 4.4 | |
| $K_2O$ | | | | | 6.5 |
| $B_2O_3$ | | | | | |
| $P_2O_5$ | | | | | |
| ZnO | | | | | |

| Example | Ex. 6 | Ex. 7 | Ex. 8 | Ex. 9 | Ex. 10 |
|---|---|---|---|---|---|
| Batched Composition (mol %) | | | | | |
| $SiO_2$ | 60 | 60 | 60 | 60 | 60 |
| $Al_2O_3$ | 10 | 10 | 5 | 5 | |
| CuO | 20 | 20 | 20 | 20 | 20 |
| $Na_2O$ | 10 | | 10 | 5 | |
| $K_2O$ | | 10 | 5 | 10 | 10 |
| $B_2O_3$ | | | | | 10 |
| $P_2O_5$ | | | | | |
| ZnO | | | | | |
| Batched Composition (wt %) | | | | | |
| $SiO_2$ | 52.7 | 50.4 | 53.0 | 51.8 | 52.8 |
| $Al_2O_3$ | 14.9 | 14.2 | 7.5 | 7.3 | 0.0 |
| CuO | 23.3 | 22.2 | 23.4 | 22.9 | 23.3 |
| $Na_2O$ | 9.1 | | 9.1 | 4.5 | |
| $K_2O$ | | 13.2 | 6.9 | 13.5 | 13.8 |
| $B_2O_3$ | | | | | 10.2 |
| $P_2O_5$ | | | | | |
| ZnO | | | | | |

| Example | Ex. 11 | Ex. 12 | Ex. 13 | Ex. 14 | Ex. 15 |
|---|---|---|---|---|---|
| Batched Composition (mol %) | | | | | |
| $SiO_2$ | 60 | 60 | 60 | 50 | 50 |
| $Al_2O_3$ | | 5 | | | |
| CuO | 20 | 20 | 20 | 20 | 20 |
| $Na_2O$ | | | | | |
| $K_2O$ | 10 | 10 | 10 | 10 | 10 |
| $B_2O_3$ | | | 5 | 10 | |
| $P_2O_5$ | 10 | 5 | 5 | 10 | 20 |
| ZnO | | | | | |
| Batched Composition (wt %) | | | | | |
| $SiO_2$ | 47.7 | 49.0 | 50.1 | 39.3 | 35.9 |
| $Al_2O_3$ | | 6.9 | | | |
| CuO | 21.0 | 21.6 | 22.1 | 20.8 | 19.0 |
| $Na_2O$ | | | | | |
| $K_2O$ | 12.5 | 12.8 | 13.1 | 12.3 | 11.2 |
| $B_2O_3$ | | | 4.8 | 9.1 | |

TABLE 1-continued

| | | | | | |
|---|---|---|---|---|---|
| P₂O₅ | 18.8 | 9.6 | 9.9 | 18.5 | 33.9 |
| ZnO | | 0.05 | | | |
| MgO | | 0.05 | | | |
| Fe₂O₃ | | 0.11 | | | |
| CaO | | 0.01 | | | |

| Example | Ex. 16 | Ex. 17 | Ex. 18 | Ex. 19 | Ex. 20 |
|---|---|---|---|---|---|
| Batched Composition (mol %) | | | | | |
| SiO₂ | 50 | 50 | 50 | 50 | 50 |
| Al₂O₃ | 25 | 20 | 25 | 25 | 20 |
| CuO | 25 | 30 | 25 | 25 | 20 |
| Na₂O | | 5 | | | 10 |
| K₂O | | | | 5 | |
| B₂O₃ | | | | | |
| P₂O₅ | | | | | |
| ZnO | | | | | |
| Batched Composition (wt %) | | | | | |
| SiO₂ | 39.8 | 40.4 | 38.3 | 37.5 | 41.4 |
| Al₂O₃ | 33.8 | 27.4 | 32.5 | 31.8 | 28.1 |
| CuO | 26.4 | 32.1 | 25.3 | 24.8 | 21.9 |
| Na₂O | | | 3.9 | | 8.5 |
| K₂O | | | | 5.9 | |
| B₂O₃ | | | | | |
| P₂O₅ | | | | | |
| ZnO | | | | | |

| Example | Ex. 21 | Ex. 22 | Ex. 23 | Ex. 24 | Ex. 25 |
|---|---|---|---|---|---|
| Batched Composition (mol %) | | | | | |
| SiO₂ | 50 | 60 | 60 | 50 | 60 |
| Al₂O₃ | 20 | 5 | | | 5 |
| CuO | 20 | 20 | 20 | 20 | 20 |
| Na₂O | | | | | 10 |
| K₂O | 10 | 10 | 10 | 10 | |
| B₂O₃ | | | 5 | 10 | |
| P₂O₅ | | 5 | 5 | 10 | 5 |
| ZnO | | | | | |
| Batched Composition (wt %) | | | | | |
| SiO₂ | 39.7 | 49.0 | 50.1 | 39.3 | 51.2 |
| Al₂O₃ | 26.9 | 6.9 | | | 7.2 |
| CuO | 21.0 | 21.6 | 22.1 | 20.8 | 22.6 |
| Na₂O | | | | | 8.8 |
| K₂O | 12.4 | 12.8 | 13.1 | 12.3 | |
| B₂O₃ | | | 4.8 | 9.1 | |
| P₂O₅ | | 9.6 | 9.9 | 18.5 | 10.1 |
| ZnO | | | | | |

| Example | Ex. 26 | Ex. 27 | Ex. 28 | Ex. 29 | Ex. 30 |
|---|---|---|---|---|---|
| Batched Composition (mol %) | | | | | |
| SiO₂ | 60 | 50 | 50 | 50 | 55 |
| Al₂O₃ | | 5 | 5 | | |
| CuO | 20 | 20 | 20 | 20 | 20 |
| Na₂O | 10 | 10 | 10 | | |
| K₂O | | | | 10 | 10 |
| B₂O₃ | 5 | 10 | 10 | 10 | 10 |
| P₂O₅ | 5 | 10 | 5 | 5 | 5 |
| ZnO | | | | | |
| Batched Composition (wt %) | | | | | |
| SiO₂ | 52.5 | 41.0 | 42.1 | 40.3 | 45.6 |
| Al₂O₃ | | 7.1 | 6.8 | | |
| CuO | 23.1 | 21.7 | 22.3 | 21.3 | 22.0 |
| Na₂O | 9.0 | 8.5 | 8.7 | | |
| K₂O | | | | 12.6 | 13.0 |
| B₂O₃ | 5.1 | 9.5 | 9.8 | 9.3 | 9.6 |
| P₂O₅ | 10.3 | 19.4 | 10.0 | 9.5 | 9.8 |
| ZnO | | | | | |

| Example | Ex. 31 | Ex. 32 | Ex. 33 | Ex. 34 | Ex. 35 |
|---|---|---|---|---|---|
| Batched Composition (mol %) | | | | | |
| SiO₂ | 55 | 60 | 55 | 60 | 55 |
| Al₂O₃ | | | 5 | 5 | |
| CuO | 20 | 20 | 20 | 20 | 20 |
| Na₂O | 10 | 15 | 15 | | |
| K₂O | | | | 10 | 10 |
| B₂O₃ | 10 | | | | 10 |
| P₂O₅ | 5 | 5 | 5 | 5 | 5 |
| ZnO | | | | | |
| Batched Composition (wt %) | | | | | |
| SiO₂ | 47.7 | 52.7 | 46.9 | 49.0 | 45.6 |
| Al₂O₃ | | | 7.2 | 6.9 | |
| CuO | 23.0 | 23.3 | 22.6 | 21.6 | 22.0 |
| Na₂O | 9.0 | 13.6 | 13.2 | | |
| K₂O | | | | 12.8 | 13.0 |
| B₂O₃ | 10.1 | | | | 9.6 |
| P₂O₅ | 10.3 | 10.4 | 10.1 | 9.6 | 9.8 |
| ZnO | | | | | |

| Example | Ex. 36 | Ex. 37 | Ex. 38 | Ex. 39 | Ex. 40 |
|---|---|---|---|---|---|
| Batched Composition (mol %) | | | | | |
| SiO₂ | 50 | 45 | 40 | 55 | 55 |
| Al₂O₃ | | | | | |
| CuO | 20 | 20 | 20 | 20 | 20 |
| Na₂O | | | | | |
| K₂O | 10 | 10 | 12.5 | 10 | 10 |
| B₂O₃ | 10 | 10 | 10 | 10 | 10 |
| P₂O₅ | 5 | 5 | 5 | 5 | 5 |
| ZnO | 5 | 10 | 12.5 | | |
| Batched Composition (wt %) | | | | | |
| SiO₂ | 40.9 | 36.3 | 31.6 | 45.6 | 45.6 |
| Al₂O₃ | | | | | |
| CuO | 21.6 | 21.3 | 20.9 | 22.0 | 22.0 |
| Na₂O | | | | | |
| K₂O | 12.8 | 12.6 | 15.5 | 13.0 | 13.0 |
| B₂O₃ | 9.5 | 9.3 | 9.2 | 9.6 | 9.6 |
| P₂O₅ | 9.7 | 9.5 | 9.3 | 9.8 | 9.8 |
| ZnO | 5.5 | 10.9 | 13.4 | | |

| Example | Ex. 41 | Ex. 42 | Ex. 43 | Ex. 44 | Ex. 45 |
|---|---|---|---|---|---|
| Batched Composition (mol %) | | | | | |
| SiO₂ | 51.5 | 51.5 | 48 | 48 | 55 |
| Al₂O₃ | 0 | 0 | 0 | 0 | |
| CuO | 25 | 25 | 30 | 30 | 20 |
| Na₂O | 0 | 0 | 0 | 0 | |
| K₂O | 9.4 | 9.4 | 8.8 | 8.8 | 10 |
| B₂O₃ | 9.4 | 9.4 | 8.8 | 8.8 | 10 |
| P₂O₅ | 4.7 | 4.7 | 4.4 | 4.4 | 5 |
| ZnO | 0 | 0 | 0 | 0 | 55 |
| Batched Composition (wt %) | | | | | |
| SiO₂ | 42.4 | 42.4 | 39.3 | 39.3 | |
| Al₂O₃ | 0.0 | 0.0 | 0.0 | 0.0 | |
| CuO | 27.3 | 27.3 | 32.5 | 32.5 | |
| Na₂O | 0.0 | 0.0 | 0.0 | 0.0 | |
| K₂O | 12.1 | 12.1 | 11.3 | 11.3 | |
| B₂O₃ | 9.0 | 9.0 | 8.4 | 8.4 | |
| P₂O₅ | 9.2 | 9.2 | 8.5 | 8.5 | |
| ZnO | 0.0 | 0.0 | 0.0 | 0.0 | |

TABLE 1-continued

Table 1

| Example | Ex. 46 | Ex. 47 | Ex. 48 | Ex. 49 | Ex. 50 |
|---|---|---|---|---|---|
| Batched Composition (mol %) | | | | | |
| $SiO_2$ | 50 | 50 | 50 | 50 | 55 |
| $Al_2O_3$ | 0 | 0 | 0 | 0 | 0 |
| CuO | 20 | 20 | 20 | 20 | 20 |
| $Na_2O$ | 0 | 0 | 0 | 0 | 0 |
| $K_2O$ | 10 | 10 | 10 | 10 | 10 |
| $B_2O_3$ | 10 | 10 | 10 | 10 | 10 |
| $P_2O_5$ | 5 | 5 | 5 | 5 | 5 |
| ZnO | 0 | 0 | 0 | 0 | 0 |
| $TiO_2$ | 5 | 0 | 0 | 0 | 0 |
| $Fe_2O_3$ | 0 | 5 | 0 | 0 | 0 |
| $Cr_2O_3$ | 0 | 0 | 5 | 0 | 0 |
| $Co_3O_4$ | 0 | 0 | 0 | 5 | 0 |
| NiO | 0 | 0 | 0 | 0 | 0 |

| Example | Ex. 51 | Ex. 52 | Ex. 53 | Ex. 54 | Ex. 55 |
|---|---|---|---|---|---|
| Batched Composition (mol %) | | | | | |
| $SiO_2$ | 40 | 45 | 50 | 55 | 50 |
| $Al_2O_3$ | 15 | 15 | 15 | 15 | 15 |
| CuO | 20 | 20 | 20 | 20 | 20 |
| $Na_2O$ | | | | | |
| $K_2O$ | 10 | 10 | 10 | 5 | 5 |
| $B_2O_3$ | 10 | 5 | 0 | 0 | 5 |
| $P_2O_5$ | 5 | 5 | 5 | 5 | 5 |
| ZnO | 0 | 0 | 0 | 0 | 0 |
| $TiO_2$ | 0 | 0 | 0 | 0 | 0 |
| $Fe_2O_3$ | 0 | 0 | 0 | 0 | 0 |
| $Cr_2O_3$ | 0 | 0 | 0 | 0 | 0 |
| $Co_3O_4$ | 0 | 0 | 0 | 0 | 0 |
| NiO | 0 | 0 | 0 | 0 | 0 |

TABLE 1-continued

Table 1

| Example | Ex. 56 | Ex. 57 | Ex. 58 | Ex. 59 | Ex. 60 |
|---|---|---|---|---|---|
| Batched Composition (mol %) | | | | | |
| $SiO_2$ | 45 | 55 | 50 | 45 | 45 |
| $Al_2O_3$ | | | | | |
| CuO | 35 | 30 | 35 | 40 | 25 |
| $Na_2O$ | | | | | |
| $K_2O$ | 7.5 | 10 | 10 | 10 | 10 |
| $B_2O_3$ | 7.5 | | | | |
| $P_2O_5$ | 5 | 5 | 5 | 5 | 5 |
| ZnO | | | | | |
| $TiO_2$ | | | | | |
| $Fe_2O_3$ | | | | | |
| $Cr_2O_3$ | | | | | |
| $Co_3O_4$ | | | | | 15 |
| NiO | | | | | |

| Example | Ex. 61 | Ex. 62 |
|---|---|---|
| Batched Composition (mol %) | | |
| $SiO_2$ | 45 | 45 |
| $Al_2O_3$ | 0 | 0 |
| CuO | 25 | 30 |
| $Na_2O$ | 0 | 0 |
| $K_2O$ | 10 | 10 |
| $B_2O_3$ | 0 | 0 |
| $P_2O_5$ | 5 | 5 |
| ZnO | 0 | 0 |
| $TiO_2$ | 0 | 10 |
| $Fe_2O_3$ | 0 | 0 |
| $Cr_2O_3$ | 0 | 0 |
| $Co_3O_4$ | 0 | 0 |
| NiO | 15 | 0 |

TABLE 2

Table 2

| Example | Ex. 1 | Ex. 2 | Ex. 3 | Ex. 4 | Ex. 5 |
|---|---|---|---|---|---|
| Melt Temp (° C.) | 1500 | 1650 | 1650 | 1650 | 1650 |
| Melt Time (hrs) | 6 | overnight | overnight | overnight | overnight |
| Crucible Type | Alumina | Quartz | Quartz | Quartz | Quartz |
| Anneal Temp (° C.) | 700 | 700 | 700 | 700 | 700 |
| Melt Appearance | Very Poor, full of large bubbles | High Quality, Surface Oxidation, Gray surface, black interior | High Quality, Surface Oxidation, Gray surface, black interior | Grey Surface, black interior | Grey Surface, black interior |
| Density by buoyancy (g/cm³) | | 2.705 | 2.781 | 2.758 | 2.741 |
| Effective molecular wt (g/mol) | 70.821 | 70.821 | 72.354 | | |
| Molar Volume (cm³/mol) | | 26.2 | 26.0 | | |
| Anneal Point by BBV (° C.) | | 694.1 | 684.9 | 598.6 | |
| Strain Point by BBV (° C.) | | 652.5 | 642.3 | 558.9 | |
| Softening Point by PPV (° C.) | | xstallized | xstallized | | |
| Vickers Hardness (kgf/mm²) | | 595 | 586 | | |
| Vickers Crack Initiation (kgf) | | 1-2 | 1-2 | | |
| Fracture Toughness by Chevron Notch (MPa m$^{0.5}$) | | 0.875 | 0.887 | | |
| CTE (ppm/° C.) | | 1.06 | 1.15 | | |
| ICP wt % oxides (Cu) | 19.6 | 19 | 21.6 | | |
| ratio $Cu^{+1}/Cu^{2+}$ | | | | | |

| Example | Ex. 6 | Ex. 7 | Ex. 8 | Ex. 9 | Ex. 10 |
|---|---|---|---|---|---|
| Melt Temp (° C.) | 1650 | 1650 | 1650 | 1650 | 1650 |
| Melt Time (hrs) | overnight | overnight | overnight | overnight | overnight |
| Crucible Type | Quartz | Quartz | Quartz | Quartz | Quartz |
| Anneal Temp (° C.) | 700 | 700 | 700 | 700 | 600 |

TABLE 2-continued

Table 2

| | | | | |
|---|---|---|---|---|
| Melt Appearance | Black and gray lustrous surface, brown and yellow interior | Black and gray lustrous surface, brown and yellow interior | Black and grey surface, primarily black interior with some green and brown streaks | Grey lustrous surface, dark yellow interior |
| Density by buoyancy (g/cm$^3$) | 2.706 | 2.666 | 2.596 | 2.716 |
| Effective molecular wt (g/mol) | | | | |
| Molar Volume (cm$^3$/mol) | | | | |
| Anneal Point by BBV (° C.) | 737.2 | | | 575.7 |
| Strain Point by BBV (° C.) | 684.4 | | | 535.2 |
| Softening Point by PPV (° C.) | | | | |
| Vickers Hardness (kgf/mm$^2$) | | | | |
| Vickers Crack Initiation (kgf) | | | | |
| Fracture Toughness by Chevron Notch (MPa m$^{0.5}$) | | | | |
| CTE (ppm/° C.) | | | | |
| ICP wt % oxides (Cu) | | | | |
| ratio Cu$^{+1}$/Cu$^{2+}$ | | | | |

| Example | Ex. 11 | Ex. 12 | Ex. 13 | Ex. 14 | Ex. 15 |
|---|---|---|---|---|---|
| Melt Temp (° C.) | 1650 | 1650 | 1650 | 1650 | 1650 |
| Melt Time (hrs) | overnight | overnight | overnight | overnight | overnight |
| Crucible Type | Quartz | Quartz | Quartz | Quartz | Quartz |
| Anneal Temp (° C.) | 600 | 700 | 600 | 600 | 600 |
| Melt Appearance | Ceramic, brittle, gray, brown, and green | Shiny metallic surface, dark yellow interior | Shiny metallic surface, dark yellow interior | Dark yellow surface w/some ceramic, dark yellow interior w/ some ceramic | Ceramic, grey surface, light brown interior |
| Density by buoyancy (g/cm$^3$) | | 2.669 | 2.673 | 2.608 | |
| Effective molecular wt (g/mol) | | | | | |
| Molar Volume (cm$^3$/mol) | | | | | |
| Anneal Point by BBV (° C.) | | | | | |
| Strain Point by BBV (° C.) | | 701 | 569 | 572.5 | |
| Softening Point by PPV (° C.) | | 759.8 | 602.8 | 510.7 | |
| Vickers Hardness (kgf/mm$^2$) | | | | | |
| Vickers Crack Initiation (kgf) | | | | | |
| Fracture Toughness by Chevron Notch (MPa m$^{0.5}$) | | | | | |
| CTE (ppm/° C.) | | | | | |
| ICP wt % oxides (Cu) | | | | | |
| ratio Cu$^{+1}$/Cu$^{2+}$ | | | | | |

| Example | Ex. 16 | Ex. 17 | Ex. 18 | Ex. 19 | Ex. 20 |
|---|---|---|---|---|---|
| Melt Temp (° C.) | 1650 | 1650 | 1650 | 1650 | 1650 |
| Melt Time (hrs) | overnight | overnight | overnight | overnight | overnight |
| Crucible Type | Quartz | Quartz | Quartz | Quartz | Quartz |
| Anneal Temp (° C.) | 700 | 700 | 700 | 700 | 700 |
| Melt Appearance | Grey Surface, black interior, copper precipitated | Grey Surface, black interior | Grey Surface, black interior | Grey Surface, black interior | Grey Surface, black interior |
| Density by buoyancy (g/cm$^3$) | 2.91 | 2.901 | 2.887 | 2.876 | 2.797 |
| Effective molecular wt (g/mol) | | | | | |
| Molar Volume (cm$^3$/mol) | | | | | |
| Anneal Point by BBV (° C.) | | | | | |
| Strain Point by BBV (° C.) | | | | | |
| Softening Point by PPV (° C.) | | | | | |
| Vickers Hardness (kgf/mm$^2$) | | | | | |
| Vickers Crack Initiation (kgf) | | | | | |
| Fracture Toughness by Chevron Notch (MPa m$^{0.5}$) | | | | | |
| CTE (ppm/° C.) | | | | | |
| ICP wt % oxides (Cu) | | | | | |
| ratio Cu$^{+1}$/Cu$^{2+}$ | | | | | |

| Example | Ex. 16 | Ex. 17 | Ex. 18 | Ex. 19 | Ex. 20 |
|---|---|---|---|---|---|
| Melt Temp (° C.) | 1650 | 1650 | 1650 | 1650 | 1650 |
| Melt Time (hrs) | overnight | overnight | overnight | overnight | overnight |
| Crucible Type | Quartz | Quartz | Quartz | Quartz | Quartz |
| Anneal Temp (° C.) | 700 | 700 | 700 | 700 | 700 |
| Melt Appearance | Grey Surface, black interior, copper precipitated | Grey Surface, black interior | Grey Surface, black interior | Grey Surface, black interior | Grey Surface, black interior |

TABLE 2-continued

Table 2

| | | | | | |
|---|---|---|---|---|---|
| Density by buoyancy (g/cm³) | 2.91 | 2.901 | 2.887 | 2.876 | 2.797 |
| Effective molecular wt (g/mol) | | | | | |
| Molar Volume (cm³/mol) | | | | | |
| Anneal Point by BBV (° C.) | | | | | |
| Strain Point by BBV (° C.) | | | | | |
| Softening Point by PPV (° C.) | | | | | |
| Vickers Hardness (kgf/mm²) | | | | | |
| Vickers Crack Initiation (kgf) | | | | | |
| Fracture Toughness by Chevron Notch (MPa m^0.5) | | | | | |
| CTE (ppm/° C.) | | | | | |
| ICP wt % oxides (Cu) | | | | | |
| ratio $Cu^{+1}/Cu^{2+}$ | | | | | |

| Example | Ex. 21 | Ex. 22 | Ex. 23 | Ex. 24 | Ex. 25 |
|---|---|---|---|---|---|
| Melt Temp (° C.) | 1650 | 1650 | 1650 | 1650 | 1650 |
| Melt Time (hrs) | Overnight | overnight | overnight | Overnight | overnight |
| Crucible Type | Quartz | Quartz | Quartz | Quartz | Quartz |
| Anneal Temp (° C.) | 700 | 650 | 650 | 650 | 650 |
| Melt Appearance | Grey Surface, yellow interior | Grey Surface, Yellow/orange interior | Grey Surface, Yellow/orange interior | Crystallized | Grey Surface, Yellow/orange interior (looks more crystalline than Ex. 22) |
| Density by buoyancy (g/cm³) | 2.774 | | | | |
| Effective molecular wt (g/mol) | | | | | |
| Molar Volume (cm³/mol) | | | | | |
| Anneal Point by BBV (° C.) | | | | | |
| Strain Point by BBV (° C.) | | | | | |
| Softening Point by PPV (° C.) | | | | | |
| Vickers Hardness (kgf/mm²) | | | | | |
| Vickers Crack Initiation (kgf) | | | | | |
| Fracture Toughness by Chevron Notch (MPa m^0.5) | | | | | |
| CTE (ppm/° C.) | | | | | |
| ICP wt % oxides (Cu) | | | | | |
| ratio $Cu^{+1}/Cu^{2+}$ | | | | | |

| Example | Ex. 26 | Ex. 27 | Ex. 28 | Ex. 29 | Ex. 30 |
|---|---|---|---|---|---|
| Melt Temp (° C.) | 1650 | 1650 | 1650 | 1650 | 1650 |
| Melt Time (hrs) | overnight | overnight | overnight | overnight | overnight |
| Crucible Type | Quartz | Quartz | Quartz | Quartz | Quartz |
| Anneal Temp (° C.) | 650 | 650 | 650 | 650 | 650 |
| Melt Appearance | Grey Surface, Yellow/orange interior (looks more crystalline than Ex. 23) | crystallized | Shiny exterior, yellow/orange interior | Shiny exterior, yellow/orange interior | Shiny exterior, yellow/orange interior |
| Density by buoyancy (g/cm³) | | | | | 2.626 |
| Effective molecular wt (g/mol) | | | | | |
| Molar Volume (cm³/mol) | | | | | |
| Anneal Point by BBV (° C.) | | | | | |
| Strain Point by BBV (° C.) | | | | | 602.4 |
| Softening Point by PPV (° C.) | | | | | 544.4 |
| Vickers Hardness (kgf/mm²) | | | | | |
| Vickers Crack Initiation (kgf) | | | | | |
| Fracture Toughness by Chevron Notch (MPa m^0.5) | | | | | |
| CTE (ppm/° C.) | | | | | |
| ICP wt % oxides (Cu) | | | | | |
| ratio $Cu^{+1}/Cu^{2+}$ | | | | | |

| Example | Ex. 31 | Ex. 32 | Ex. 33 | Ex. 34 | Ex. 35 |
|---|---|---|---|---|---|
| Melt Temp (° C.) | 1650 | 1650 | 1650 | 1650 | 1650 |
| Melt Time (hrs) | overnight | overnight | overnight | overnight | overnight |
| Crucible Type | Quartz | Quartz | Quartz | Quartz | Quartz |
| Anneal Temp (° C.) | 650 | 650 | 650 | 650 | 650 |
| Melt Appearance | Shiny exterior, yellow/orange interior | Lighter yellow, more crystalline | Lighter yellow, crystallized | Orange Interior, shiny metallic surface | Orange Interior, shiny metallic surface |
| Density by buoyancy (g/cm³) | | | | | |
| Effective molecular wt (g/mol) | | | | | |
| Molar Volume (cm³/mol) | | | | | |
| Anneal Point by BBV (° C.) | | | | | |
| Strain Point by BBV (° C.) | | | | | |

TABLE 2-continued

| | | | | | |
|---|---|---|---|---|---|
| Softening Point by PPV (° C.) | | | | | |
| Vickers Hardness (kgf/mm$^2$) | | | | | |
| Vickers Crack Initiation (kgf) | | | | | |
| Fracture Toughness by Chevron Notch (MPa m$^{0.5}$) | | | | | |
| CTE (ppm/° C.) | | | | | |
| ICP wt % oxides (Cu) | | | | | |
| ratio Cu$^{+1}$/Cu$^{2+}$ | | | | | |

| Example | Ex. 36 | Ex. 37 | Ex. 38 | Ex. 39 | Ex. 40 |
|---|---|---|---|---|---|
| Melt Temp (° C.) | 1650 | 1650 | 1650 | 1650 | 1650 |
| Melt Time (hrs) | overnight | overnight | overnight | overnight | overnight |
| Crucible Type | Quartz | Quartz | Quartz | Quartz | Quartz |
| Anneal Temp (° C.) | 650 | 650 | 650 | none | 650 |
| Melt Appearance | Orange Interior, shiny metallic surface | Orange Interior, shiny metallic surface | Orange Interior, shiny metallic surface | Yellow, Orange | Orange Interior, shiny metallic surface |
| Density by buoyancy (g/cm$^3$) | | | | | |
| Effective molecular wt (g/mol) | | | | | |
| Molar Volume (cm$^3$/mol) | | | | | |
| Anneal Point by BBV (° C.) | | | | | |
| Strain Point by BBV (° C.) | | | | | |
| Softening Point by PPV (° C.) | | | | | |
| Vickers Hardness (kgf/mm$^2$) | | | | | |
| Vickers Crack Initiation (kgf) | | | | | |
| Fracture Toughness by Chevron Notch (MPa m$^{0.5}$) | | | | | |
| CTE (ppm/° C.) | | | | | |
| ICP wt % oxides (Cu) | | | | | |
| ratio Cu$^{+1}$/Cu$^{2+}$ | | | | | |

| Example | Ex. 36 | Ex. 37 | Ex. 38 | Ex. 39 | Ex. 40 |
|---|---|---|---|---|---|
| Melt Temp (° C.) | 1650 | 1650 | 1650 | 1650 | 1650 |
| Melt Time (hrs) | overnight | overnight | overnight | overnight | overnight |
| Crucible Type | Quartz | Quartz | Quartz | Quartz | Quartz |
| Anneal Temp (° C.) | 650 | 650 | 650 | none | 650 |
| Melt Appearance | Orange Interior, shiny metallic surface | Orange Interior, shiny metallic surface | Orange Interior, shiny metallic surface | Yellow, Orange | Orange Interior, shiny metallic surface |
| Density by buoyancy (g/cm$^3$) | | | | | |
| Effective molecular wt (g/mol) | | | | | |
| Molar Volume (cm$^3$/mol) | | | | | |
| Anneal Point by BBV (° C.) | | | | | |
| Strain Point by BBV (° C.) | | | | | |
| Softening Point by PPV (° C.) | | | | | |
| Vickers Hardness (kgf/mm$^2$) | | | | | |
| Vickers Crack Initiation (kgf) | | | | | |
| Fracture Toughness by Chevron Notch (MPa m$^{0.5}$) | | | | | |
| CTE (ppm/° C.) | | | | | |
| ICP wt % oxides (Cu) | | | | | |
| ratio Cu$^{+1}$/Cu$^{2+}$ | | | | | |

| Example | Ex. 41 | Ex. 42 | Ex. 43 | Ex. 44 |
|---|---|---|---|---|
| Melt Temp (° C.) | 1650 | 1650 | 1650 | 1650 |
| Melt Time (hrs) | overnight | overnight | overnight | overnight |
| Crucible Type | Quartz | Quartz | Quartz | Quartz |
| Anneal Temp (° C.) | none | 650 | none | 650 |
| Melt Appearance | Yellow, Orange | Orange Interior, shiny metallic surface | Yellow, Orange | Orange Interior, shiny metallic surface |
| Density by buoyancy (g/cm$^3$) | | | 2.816 | |
| Effective molecular wt (g/mol) | | | | |
| Molar Volume (cm$^3$/mol) | | | | |
| Anneal Point by BBV (° C.) | | | | |
| Strain Point by BBV (° C.) | | | | |
| Softening Point by PPV (° C.) | | | | |
| Vickers Hardness (kgf/mm$^2$) | | | | |
| Vickers Crack Initiation (kgf) | | | | |
| Fracture Toughness by Chevron Notch (MPa m$^{0.5}$) | | | | |
| CTE (ppm/° C.) | | | | |
| ICP wt % oxides (Cu) | | | | |
| ratio Cu$^{+1}$/Cu$^{2+}$ | | | | |

TABLE 2-continued

| Example | Ex. 46 | Ex. 47 | Ex. 48 | Ex. 49 | Ex. 50 |
|---|---|---|---|---|---|
| Melt Temp (° C.) | | | | | |
| Melt Time (hrs) | | | | | |
| Crucible Type | | | | | |
| Anneal Temp (° C.) | | | | | |
| Melt Appearance | reddish orange | orange | greenish crystallized | light green, greener than Ex. 48 | |
| Density by buoyancy (g/cm$^3$) | | | | | |
| Effective molecular wt (g/mol) | | | | | |
| Molar Volume (cm$^3$/mol) | | | | | |
| Anneal Point by BBV (° C.) | | | | | |
| Strain Point by BBV (° C.) | | | | | |
| Softening Point by PPV (° C.) | | | | | |
| Vickers Hardness (kgf/mm$^2$) | | | | | |
| Vickers Crack Initiation (kgf) | | | | | |
| Fracture Toughness by Chevron Notch (MPa m$^{0.5}$) | | | | | |
| CTE (ppm/° C.) | | | | | |
| ICP wt % oxides (Cu) | | | | | |
| ratio Cu$^{+1}$/Cu$^{2+}$ | | | | | |

| Example | Ex. 51 | Ex. 52 | Ex. 53 | Ex. 54 | Ex. 55 |
|---|---|---|---|---|---|
| Melt Temp (° C.) | | | | | |
| Melt Time (hrs) | | | | | |
| Crucible Type | | | | | |
| Anneal Temp (° C.) | | | | | |
| Melt Appearance | Yellow and Black | Yellow and Brown | Yellow | Black with some orange on bottom | Black with some orange on edges |
| Density by buoyancy (g/cm$^3$) | | | | | |
| Effective molecular wt (g/mol) | | | | | |
| Molar Volume (cm$^3$/mol) | | | | | |
| Anneal Point byBBV (° C.) | | | | | |
| Strain Point by BBV (° C.) | | | | | |
| Softening Point by PPV (° C.) | | | | | |
| Vickers Hardness (kgf/mm$^2$) | | | | | |
| Vickers Crack Initiation (kgf) | | | | | |
| Fracture Toughness by Chevron Notch (MPa m$^{0.5}$) | | | | | |
| CTE (ppm/° C.) | | | | | |
| ICP wt % oxides (Cu) | | | | | |
| ratio Cu$^{+1}$/Cu$^{2+}$ | | | | | |

| Example | Ex. 56 |
|---|---|
| Melt Temp (° C.) | |
| Melt Time (hrs) | |
| Crucible Type | |
| Anneal Temp (° C.) | |
| Melt Appearance | Pumpkin-colored |
| Density by buoyancy (g/cm$^3$) | |
| Effective molecular wt (g/mol) | |
| Molar Volume (cm$^3$/mol) | |
| Anneal Point by BBV (° C.) | |
| Strain Point by BBV (° C.) | |
| Softening Point by PPV (° C.) | |
| Vickers Hardness (kgf/mm$^2$) | |
| Vickers Crack Initiation (kgf) | |
| Fracture Toughness by Chevron Notch (MPa m$^{0.5}$) | |
| CTE (ppm/° C.) | |
| ICP wt % oxides (Cu) | |
| ratio Cu$^{+1}$/Cu$^{2+}$ | |

*The term "crystallized" as used here refers to a non-glassy appearance.

TABLE 3

| | Example | | | | |
|---|---|---|---|---|---|
| | Ex. 1 | Ex. 2 | Ex. 3 | Ex. 4 | Ex. 5 |
| XRD powder | | | none | Tenorite (CuO) | Tenorite (CuO) |
| XRD surface | | | | Tenorite (CuO) | Tenorite (CuO) |
| XPS vacuum fracture + 2 min air | | | | | |
| % $Cu^{1+}$ and $Cu^0$ | | | | | 85.2 |
| % $Cu^{2+}$ | | | | | 14.8 |
| StDev | | | | | 1 |
| XPS vacuum fracture | | | | | |
| % $Cu^{1+}$ and $Cu^0$ | | | | | |
| % $Cu^{2+}$ | | | | | |
| StDev | | | | | |

| | Example | | | | |
|---|---|---|---|---|---|
| | Ex. 6 | Ex. 7 | Ex. 8 | Ex. 9 | Ex. 10 |
| XRD powder | Tenorite (CuO) and Cuprite ($Cu_2O$) | Tenorite (CuO) and Cuprite ($Cu_2O$) | | Cuprite ($Cu_2O$) | Cuprite ($Cu_2O$) |
| XRD surface | Tenorite (CuO) and Cuprite ($Cu_2O$) | Tenorite (CuO) and Cuprite ($Cu_2O$) | | no peaks | Tenorite (CuO) and Cuprite ($Cu_2O$) |
| XPS vacuum fracture + 2 min air | | | | | |
| % $Cu^{1+}$ and $Cu^0$ | 84.2 | | | | 74.6 |
| % $Cu^{2+}$ | 15.8 | | | | 25.4 |
| StDev | 0.1 | | | | 1.5 |
| XPS vacuum fracture | | | | | |
| % $Cu^{1+}$ and $Cu^0$ | | | | | |
| % $Cu^{2+}$ | | | | | |
| StDev | | | | | |

| | Example | | | | |
|---|---|---|---|---|---|
| | Ex. 11 | Ex. 12 | Ex. 13 | Ex. 14 | Ex. 15 |
| XRD powder | | Cuprite ($Cu_2O$), K1—$xAl^{1+}$xSi1—xO4, Al2O3*0.95P2O5, Cu1.82K0.2(Al3.9Si8.1O24), K2SiO3 | Cuprite (Cu2O) | Cuprite ($Cu_2O$) | |
| XRD surface | | Tenorite (CuO), Cuprite ($Cu_2O$), K1—$xAl^{1+}$xSi1—xO4, Al2O3*0.95P2O5 | Cuprite ($Cu_2O$) | Cuprite ($Cu_2O$) | |
| XPS vacuum fracture + 2 min air | | | | | |
| % $Cu^{1+}$ and $Cu^0$ | | 92.4 | 80.3 | 91.3 | |
| % $Cu^{2+}$ | | 7.6 | 19.7 | 8.7 | |
| StDev | | 1.2 | 2.5 | 0.4 | |
| XPS vacuum fracture | | | | | |
| % $Cu^{1+}$ and $Cu^0$ | | 87.1 | | 93.1 | |
| % $Cu^{2+}$ | | 12.9 | | 6.9 | |
| StDev | | 2.6 | | 0.6 | |

| | Example | | | | |
|---|---|---|---|---|---|
| | Ex. 16 | Ex. 17 | Ex. 18 | Ex. 19 | Ex. 20 |
| XRD powder | Tenorite (CuO) | Tenorite (CuO) | Tenorite (CuO) | none | Tenorite (CuO) |

TABLE 3-continued

|  | | | | | |
|---|---|---|---|---|---|
| XRD surface | Tenorite (CuO) | Tenorite (CuO) | Tenorite (CuO) | Tenorite (CuO) | Tenorite (CuO) |
| XPS vacuum fracture + 2 min air | | | | | |
| % $Cu^{1+}$ and $Cu^0$ | | | | | |
| % $Cu^{2+}$ | | | | | |
| StDev | | | | | |
| XPS vacuum fracture | | | | | |
| % $Cu^{1+}$ $Cu^0$ | | | | | |
| % $Cu^{2+}$ | | | | | |
| StDev | | | | | |

| | Example | | | | |
|---|---|---|---|---|---|
| | Ex. 21 | Ex. 22 | Ex. 23 | Ex. 24 | Ex. 25 |
| XRD powder | Cuprite ($Cu_2O$) | Cuprite, Tenorite, Sodium Borate ($Na_2B_{18}O_{28}$), Potassium Aluminum Silicate ($KAlSiO_4$) | Cuprite | Cristobalite, Copper | Cuprite, Sodium Silicate ($Na_2Si_2O_5$), Aluminum Phosphate ($AlPO_4$) |
| XRD surface | Tenorite (CuO) | Cuprite, Tenorite, Sodium Borate | Cuprite, Tenorite, Sodium Borate | Cuprite | Cuprite, Tenorite, Sodium Silicate ($Na_2Si_2O_5$), Aluminum Phosphate ($AlPO_4$) |
| XPS vacuum fracture + 2 min air | | | | | |
| % $Cu^{1+}$ and $Cu^0$ | 81.7 | | | | |
| % $Cu^{2+}$ | 18.3 | | | | |
| StDev | 0.2 | | | | |
| XPS vacuum fracture | | | | | |
| % $Cu^{1+}$ and $Cu^0$ | | | | | |
| % $Cu^{2+}$ | | | | | |
| StDev | | | | | |

| | Example | | | | |
|---|---|---|---|---|---|
| | Ex. 26 | Ex. 27 | Ex. 28 | Ex. 29 | Ex. 30 |
| XRD powder | Cristobalite, Cuprite, Copper Phosphate ($Cu_3(PO_4)_2$) | Copper, Cuprite, Sodium Copper Phosphate ($Na_6Cu_9(PO_4)_6$) | Cuprite | Cuprite | Cuprite |
| XRD surface | Cristobalite, Cuprite, Tenorite, Copper Phosphate | Copper, Cuprite, Tenorite, Sodium Copper Phosphate | Cuprite, Sodium Borate Hydrate | Cuprite | Cuprite, Tenorite |
| XPS vacuum fracture + 2 min air | | | | | |
| % $Cu^{1+}$ and $Cu^0$ | | | | 87.1 | 75 |
| % $Cu^{2+}$ | | | | 12.9 | 25 |
| StDev | | | | 1.2 | 0.2 |
| XPS vacuum fracture | | | | | |
| % $Cu^{1+}$ and $Cu^0$ | | | | | |

TABLE 3-continued

% $Cu^{2+}$
StDev

| | Example | | | | |
|---|---|---|---|---|---|
| | Ex. 31 | Ex. 32 | Ex. 33 | Ex. 34 | Ex. 35 |
| XRD powder | Cuprite | Cristobalite, Cuprite, Sodium Phosphate ($Na_3PO_4$), Aluminum Phosphate Hydrate ($AlPO_4 \cdot xH_2O$), Copper Phosphate ($Cu_5P_2O_{10}$) | Cuprite, Sodium Phosphate, $Na_{0.24}H_{4.9}((Al_{5.14}Si_{48.86})O_{106})(H_2O)_{26.5}$ | | |
| XRD surface | Cuprite, Tenorite, Tincalconite ($Na_2B_4O_7 \cdot 5H_2O$), Copper Phosphate Hydrate $Cu_3(PO_3)_6 \cdot 14H_2O$ | Cristobalite, Tenorite, Sodium Phosphate ($Na_3PO_4$), Aluminum Phosphate Hydrate ($AlPO_4 \cdot xH_2O$), Copper Phosphate ($Cu_5P_2O_{10}$) | Tenorite, Sodium Phosphate, Cuprite | | |
| XPS vacuum fracture + 2 min air | | | | | |
| % $Cu^{1+}$ and $Cu^0$ | 68.7 | | | | |
| % $Cu^{2+}$ | 31.3 | | | | |
| StDev | 0.6 | | | | |
| XPS vacuum fracture | | | | | |
| % $Cu^{1+}$ and $Cu^0$ | | | | | |
| % $Cu^{2+}$ | | | | | |
| StDev | | | | | |

| | Example | | | | |
|---|---|---|---|---|---|
| | Ex. 36 | Ex. 37 | Ex. 38 | Ex. 39 | Ex. 40 |
| XRD powder | Cuprite, Potassium Zinc Phosphate ($KZnPO_4$) | Cuprite, Potassium Zinc Phosphate, Potassium Zinc Silicate ($K_{1.10}Zn_{0.55}Si_{1.45}O_4$), Potassium Zinc Phosphate ($K_6Zn(P_2O_7)_2$ | Cuprite, Potassium Zinc Phosphate ($KZnPO_4$), Potassium Zinc Silicate, Potassium Zinc Phosphate | Cuprite | Cuprite |
| XRD surface | Cuprite, Potassium Zinc Phosphate ($KZnPO_4$), Copper Silicon Phosphide ($Cu_{0.56}Si_{1.44})P_2$, Tenorite | Tenorite, Copper Zinc Phosphate ($CuZn(P_2O_7)$, Potassium Phosphate ($K_4(P_2O_8)$, Aluminum Phosphate ($AlPO_4$) | Tenorite, Potassium Zinc Phosphate, Potassium Zinc Silicate, Potassium Copper Oxide ($K_3CuO_4$), Cuprite, Copper Oxide Phosphate ($Cu_4O(PO_4)_2$ | | |
| XPS vacuum fracture + 2 min air | | | | | |
| % $Cu^{1+}$ and $Cu^0$ | | | | | |
| % $Cu^{2+}$ | | | | | |
| StDev | | | | | |

TABLE 3-continued

| | Example | | | | |
|---|---|---|---|---|---|
| | Ex. 41 | Ex. 42 | Ex. 43 | Ex. 44 | Ex. 45 |
| XRD powder | Cuprite | Cuprite | Cuprite | Cuprite | |
| XRD surface | | | | | |
| XPS vacuum fracture + 2 min air | | | | | |
| % $Cu^{1+}$ Cu0 | | | | | |
| % $Cu^{2+}$ | | | | | |
| StDev | | | | | |
| XPS vacuum fracture | | | | | |
| % $Cu^{1+}$ Cu0 | | | | | |
| % $Cu^{2+}$ | | | | | |
| StDev | | | | | |

| | Example | | | | |
|---|---|---|---|---|---|
| | Ex. 46 | Ex. 47 | Ex. 48 | Ex. 49 | Ex. 50 |
| XRD powder | Cuprite, Copper Titanium Oxide, Anatase | | | Cuprite | |
| XRD surface | Cuprite, Copper Titanium Oxide, Anatase | | | | |
| XPS vacuum fracture + 2 min air | | | | | |
| % $Cu^{1+}$ Cu0 | | | | | |
| % $Cu^{2+}$ | | | | | |
| StDev | | | | | |
| XPS vacuum fracture | | | | | |
| % $Cu^{1+}$ Cu0 | | | | | |
| % $Cu^{2+}$ | | | | | |
| StDev | | | | | |

| | Example | | | | |
|---|---|---|---|---|---|
| | Ex. 51 | Ex. 52 | Ex. 53 | Ex. 54 | Ex. 55 |
| XRD powder | Cuprite | Tenorite and cuprite | cuprite | tenorite and cuprite | tenorite and cuprite |
| XRD surface | Tenorite and cuprite | Tenorite and cuprite | Tenorite and cuprite | tenorite | tenorite |
| XPS vacuum fracture + 2 min air | | | | | |
| % $Cu^{1+}$ Cu0 | | | | | |
| % $Cu^{2+}$ | | | | | |
| StDev | | | | | |

TABLE 3-continued

XPS
vacuum
fracture

% Cu$^{1+}$
Cu0
% Cu$^{2+}$
StDev

|  | Example |
|---|---|
|  | Ex. 56 |
| XRD powder | Cuprite and copper potassium oxide |
| XRD surface | cuprite and tenorite and potassium borate |

XPS vacuum
fracture + 2 min
air

% Cu$^{1+}$ Cu0
% Cu$^{2+}$
StDev

XPS vacuum
fracture

% Cu$^{1+}$ Cu0
% Cu$^{2+}$
StDev

TABLE 4

| | Example | | | | |
|---|---|---|---|---|---|
| | Ex. 1 | Ex. 2 | Ex. 3 | Ex. 4 | Ex. 5 |
| Coupon Testing As-Received EPA Test (*S. Aureus*) | | <log 1 | <log 1 | <log 1 | <log 1 |
| Coupon Testing As-Received EPA Re-Test | | | <log 1 | | |
| Coupon Testing 1 Day 85° C./85% RH EPA Test | | | | | |
| ICP Total Cu in wt % | | | | 21.6 | 21.7 |
| ICP Cu$^{+1}$/total Cu | | | 0.86 | 0.87 | 0.88 |

| | Example | | | | |
|---|---|---|---|---|---|
| | Ex. 6 | Ex. 7 | Ex. 8 | Ex. 9 | Ex. 10 |
| Coupon Testing As-Received EPA Test (*S. Aureus*) | >log 3 | log 2.84 | | <log 1 | <log 1 |
| Coupon Testing As-Received EPA Re-Test | >log 1 | | | <log 1 | <log 1 |
| Coupon Testing 1 Day 85° C./85% RH EPA Test | | | | | |
| ICP Total Cu in wt % | 19.6 | | | 15.8 | 22 |
| ICP Cu$^{+1}$/total Cu | 0.88 | 0.86 | | 0.78 | 0.8 |

| | Example | | | | |
|---|---|---|---|---|---|
| | Ex. 11 | Ex. 12 | Ex. 13 | Ex. 14 | Ex. 15 |
| Coupon Testing As-Received EPA Test (*S. Aureus*) | | | >log 4 | >log 3 | >log 6 |
| Coupon Testing As-Received EPA Re-Test | | | >log 3 | >log 4 | |
| Coupon Testing 1 Day 85° C./85% RH EPA Test | | | | | |
| ICP Total Cu in wt % | | | 20.8 | 20.8 | 20.5 |
| ICP Cu$^{+1}$/total Cu | | | 0.85 | 0.77 | 0.85 |

| | Example | | | | |
|---|---|---|---|---|---|
| | Ex. 21 | Ex. 22 | Ex. 23 | Ex. 24 | Ex. 25 |
| Coupon Testing As-Received EPA Test (*S. Aureus*) | | <log 1 | <log 1 | | >log 4 |
| Coupon Testing As-Received EPA Re-Test | | | | | |
| Coupon Testing 1 Day 85° C./85% RH EPA Test | | <log 1 | <log 1 | | <log 1 |
| ICP Total Cu in wt % | 18.1 | 21.5 | 21.9 | | 21.5 |
| ICP Cu$^{+1}$/total Cu | 0.92 | 0.8 | 0.8 | | 0.85 |

| | Example | | | | |
|---|---|---|---|---|---|
| | Ex. 26 | Ex. 27 | Ex. 28 | Ex. 29 | Ex. 30 |
| Coupon Testing As-Received EPA Test (*S. Aureus*) | | | >log 3 | >log 3 | >log 4 |
| Coupon Testing As-Received EPA Re-Test | | | | | |
| Coupon Testing 1 Day 85° C./85% RH EPA Test | | | >log 2 | >log 2 | >log 4 |
| ICP Total Cu in wt % | 21.3 | 21.4 | 22.2 | 21.6 | |
| ICP Cu$^{+1}$/total Cu | 0.75 | 0.82 | 0.89 | 0.86 | |

| | Example | | | | |
|---|---|---|---|---|---|
| | Ex. 31 | Ex. 32 | Ex. 33 | Ex. 34 | Ex. 35 |
| Coupon Testing As-Received EPA Test (*S. Aureus*) | >log 3 | | | | |
| Coupon Testing As-Received EPA Re-Test | | | | | |

TABLE 4-continued

| | Ex. 37 | Ex. 38 | Ex. 39 |
|---|---|---|---|
| Coupon Testing 1 Day 85° C./85% RH EPA Test | >log 2 | | |
| ICP Total Cu in wt % | 22.4 | 19.8 | 19.1 |
| ICP Cu$^{+1}$/total Cu | 0.86 | 0.77 | 0.85 |

| | Example | | | |
|---|---|---|---|---|
| | Ex. 41 | Ex. 42 | Ex. 43 | Ex. 44 |
| Coupon Testing As-Received EPA Test (S. Aureus) | | | >log 6 | log 5.93 |
| Coupon Testing As-Received EPA Re-Test | | | | |
| Coupon Testing 1 Day 85° C./85% RH EPA Test | | | | |
| ICP Total Cu in wt % | | | | |
| ICP Cu$^{+1}$/total Cu | | | 0.88 | |

| | Example | | | |
|---|---|---|---|---|
| | Ex. 46 | Ex. 49 | Ex. 56 | Ex. 58 |
| Coupon Testing As-Received EPA Test (S. Aureus) | 0.53 | 1.42 | 6.151 | 6.151 |
| Coupon Testing As-Received EPA Re-Test | | | | |
| Coupon Testing 1 Day 85° C./85% RH EPA Test | | | | |
| ICP Total Cu in wt % | | | | |
| ICP Cu$^{+1}$/total Cu | | | | |

Regarding Example 13, SEM images indicate that phase separation occurred and included a glassy matrix phase and a dispersed glassy second phase. The dispersed phase is considered a degradable phase and included cuprite crystals. The degradation of the dispersed phase was evident when that phase partially dissolved when the formed glass was polished in water. EDS analysis showed a glassy phase enriched in silicon (i.e., a durable phase) relative to both the glassy second phase and crystalline phase. The crystalline phase was the most copper-rich. Without being bound by theory, it is believed that the glassy second phase is enriched in boron. The phase separation of the degradable phase (including the precipitation of cuprite crystals) occurred readily without additional heat treatment beyond simple post-melt annealing.

Figure 3:
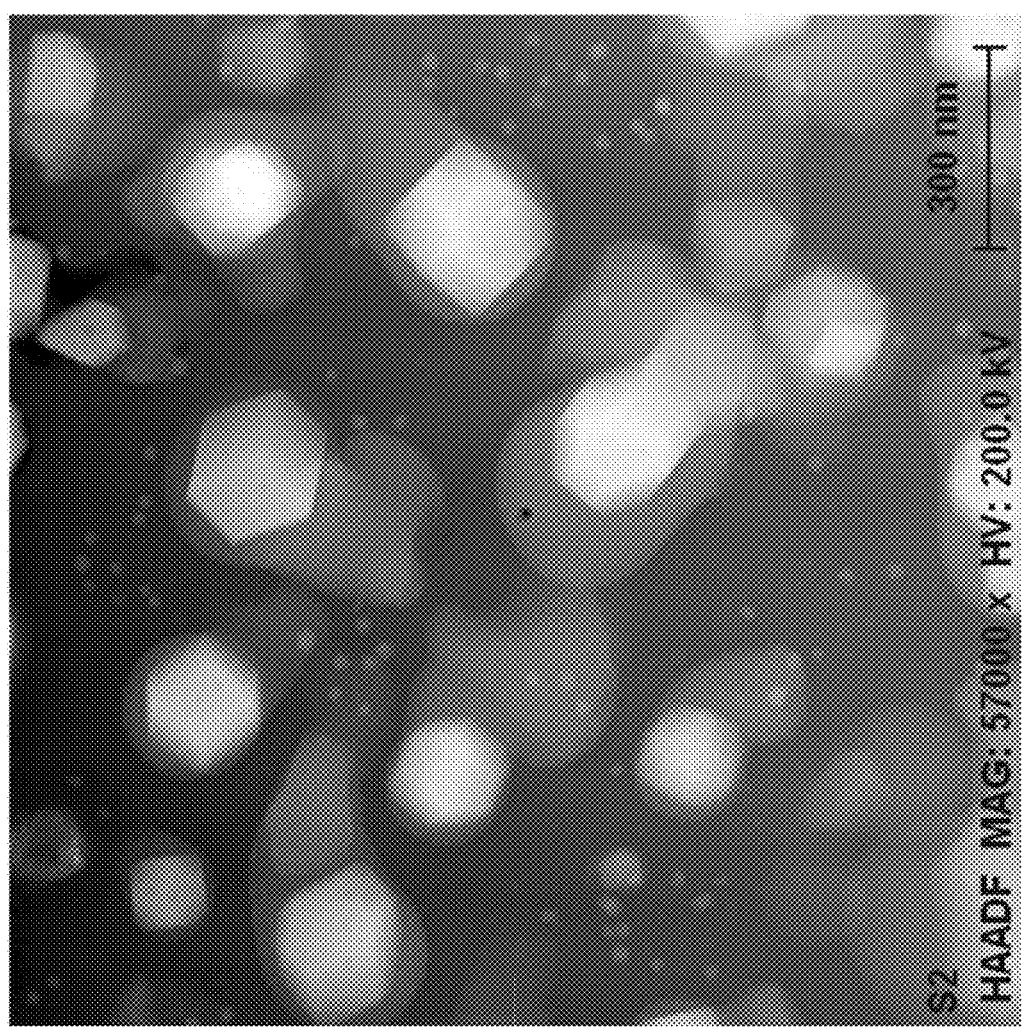
FIG. 3 is a transmission electron microscopy (TEM) image of an antimicrobial glass, according to one or more embodiments.
Figure 4:
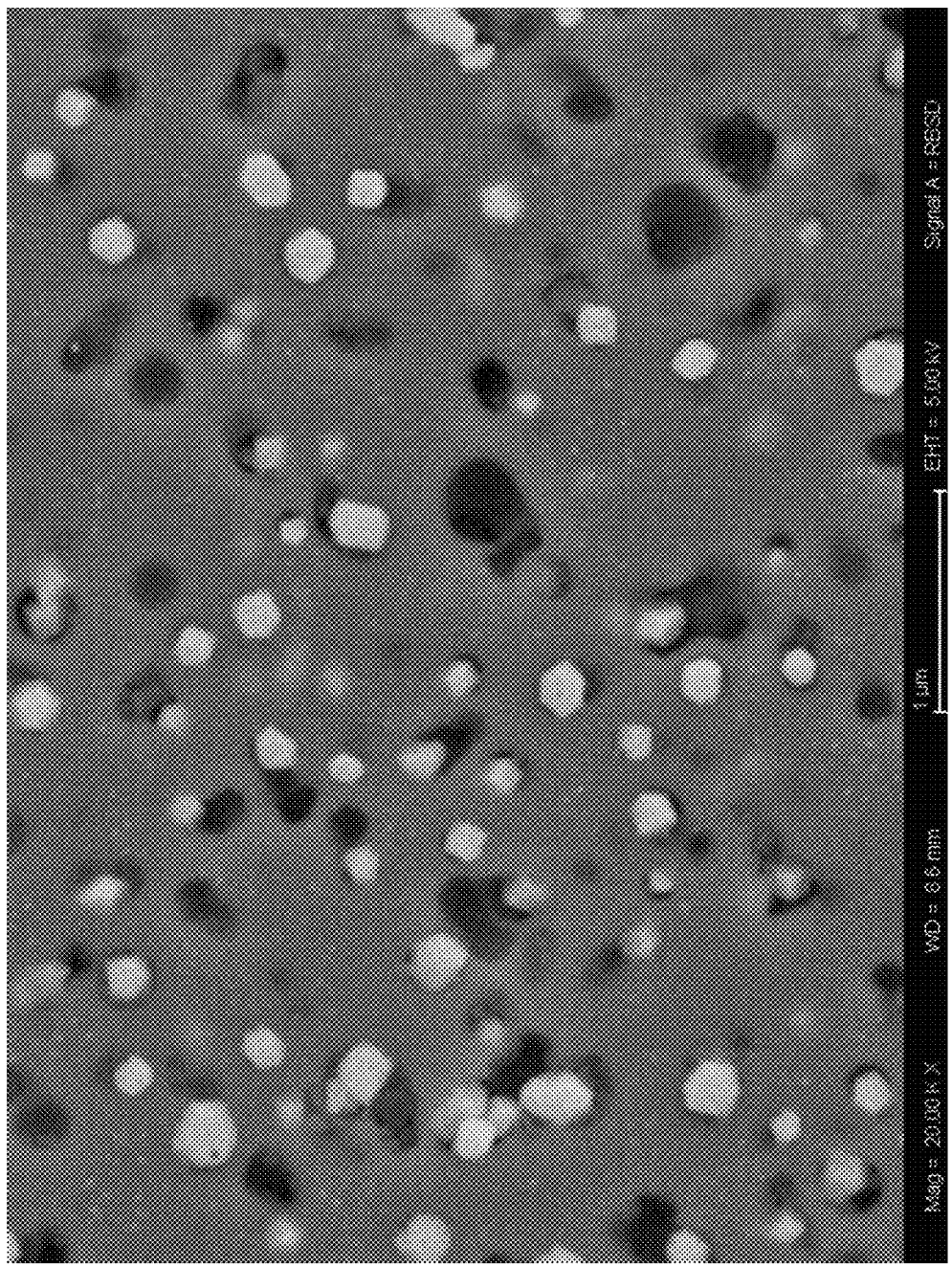
FIG. 4 is a scanning electron microscopy (SEM) image of a cross-section of the antimicrobial glass shown in FIG. 3.
Figure 5:
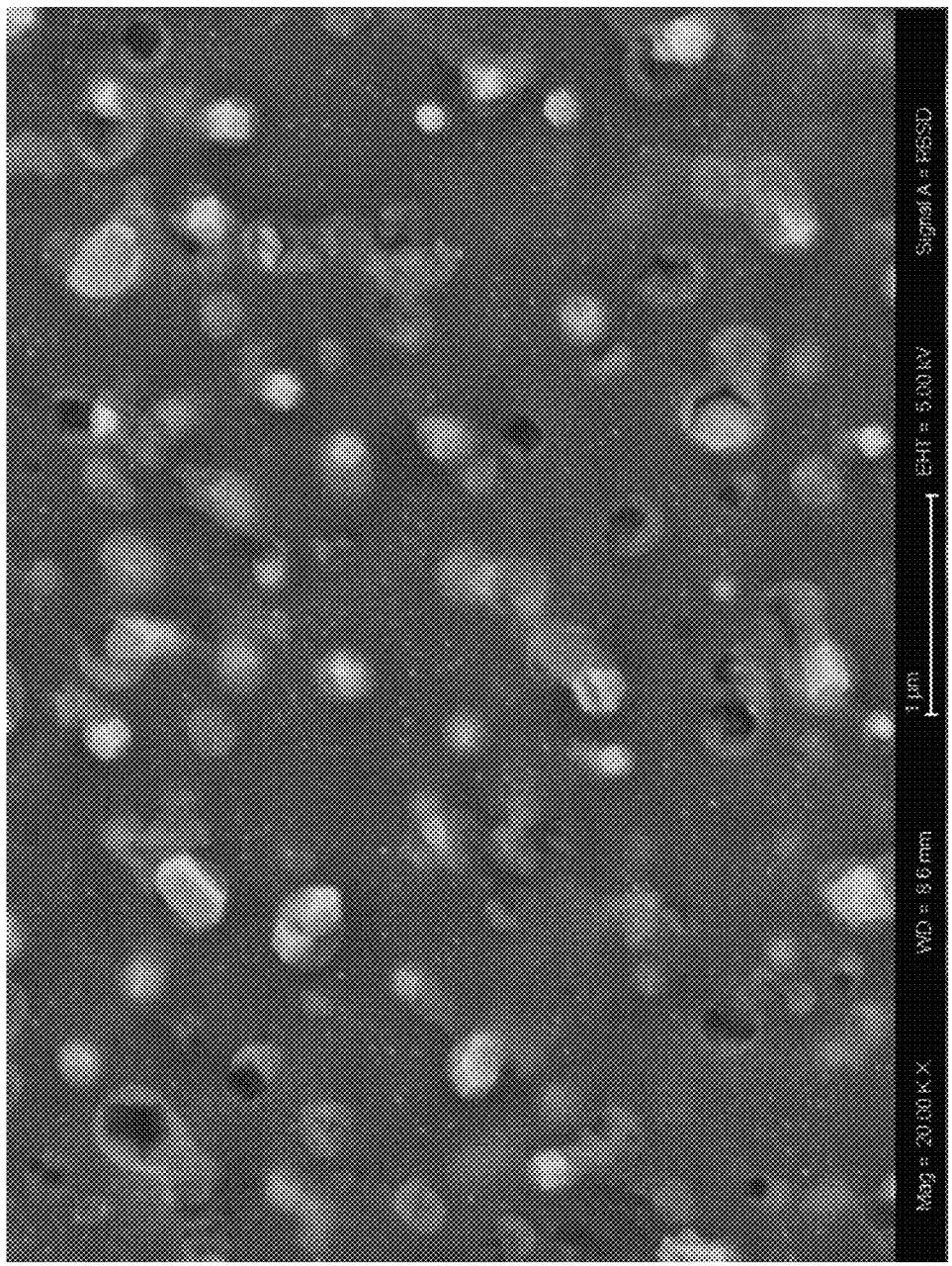
FIG. 5 is a SEM image of a fracture cross-section of the antimicrobial glass shown in FIG. 3.

FIGS. 3-5 are TEM and SEM images of a glasses made from the composition of Example 30. FIG. 3 shows a TEM image in which the darkest areas indicate a silica-rich glassy phase and the lighter areas are phase-separated glassy regions enriched with phosphorus, boron and potassium. As discussed above, these phase-separated glassy regions are degradable regions, and the silica-rich glassy phase is a durable phase. Both the degradable phase and durable phase form the glass phase of the glass. The lightest areas shown in the TEM image of FIG. 3 indicate cuprite crystals. The areas that are appear darker than the lightest areas indicate phase-separated glassy regions enriched with phosphorus, boron and potassium (i.e., the degradable phase). The silica-rich glassy phase is indicated by the darkest regions in FIG. 3. Facets of the cuprite crystals can be seen in the TEM image of FIG. 3. FIG. 4 shows a SEM image of a cross-section of the glass, after polishing with water. From FIG. 4, a preferential dissolution of a degradable phase (i.e., the phase-separated glassy regions enriched with phosphorus, boron and potassium shown in FIG. 3) in water can be seen. The Cu$^{1+}$ ions contained in the cuprite crystals that form the degradable phase are released by the dissolution of the degradable phase.

Figure 6:
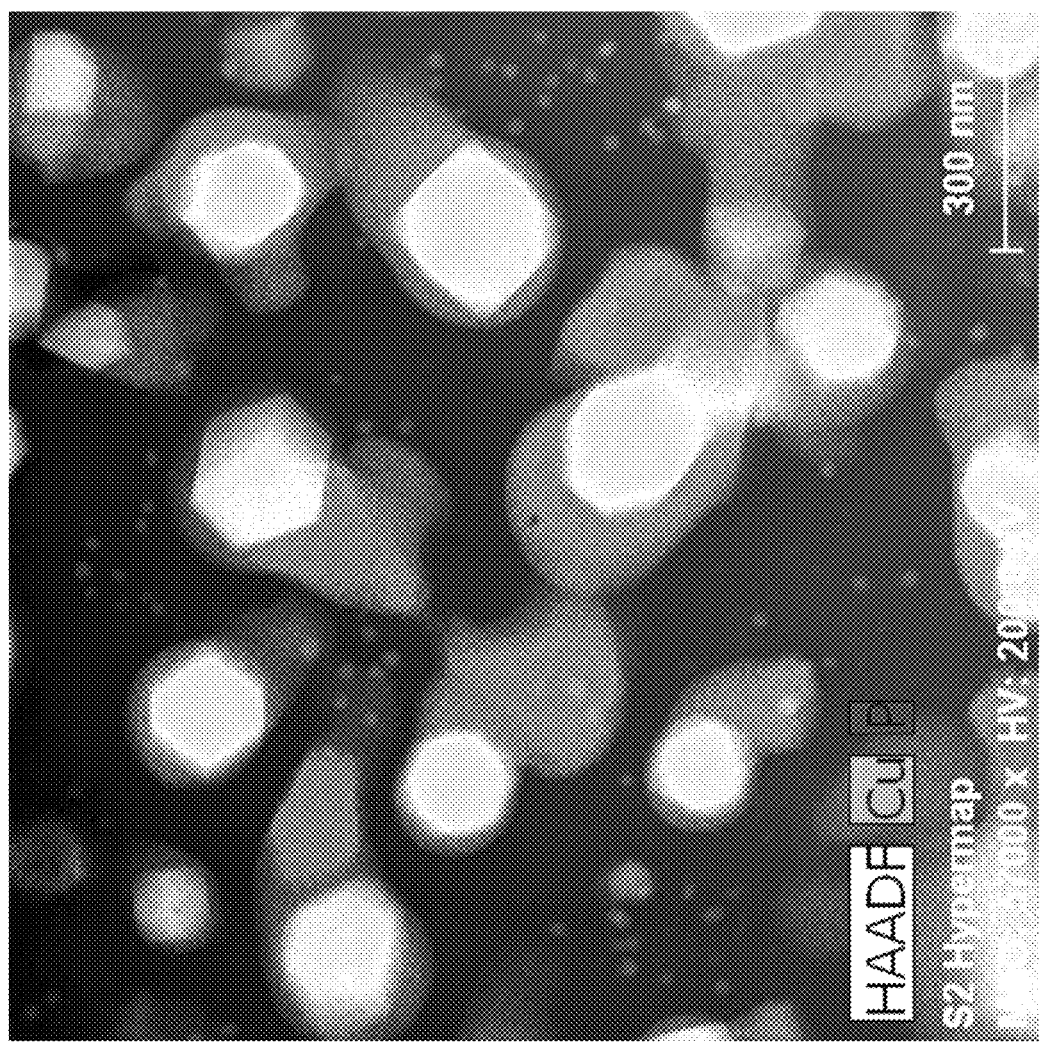
FIG. 6 is an SEM image of the antimicrobial glass according to one or more embodiments.

FIG. 6 shows an STEM image of the glasses made from the compositions described herein. FIG. 6 shows a three-phase morphology in which copper is present in a particulate form and wrapped by phosphate and distributed in a glass matrix. Because the phosphate is lightly soluble in water and hence it will be dissolved by water, exposing the Cu particles that will release active Cu species to function (killing viruses and bacteria).

Figure 8B:
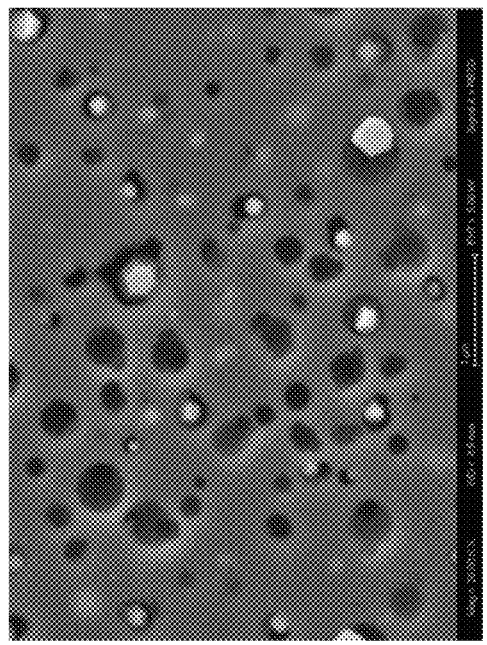
FIG. 8B shows a polished cross-section of Example 30, after an additional heat treatment at 800° C. for 1 hour.
Figure 8A:
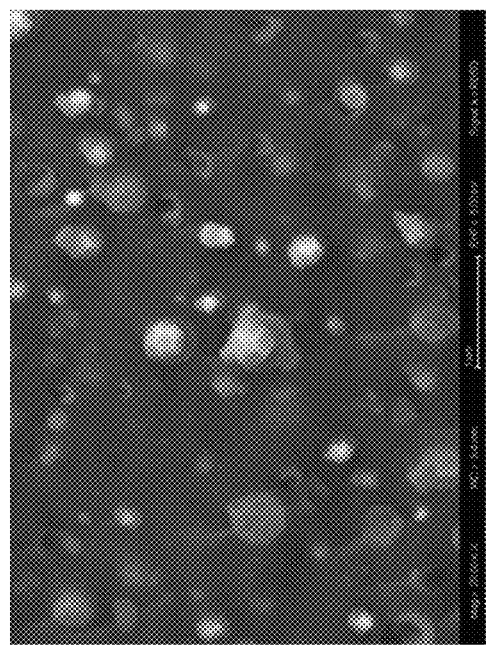
FIG. 8A shows a fracture cross-section of Example 30, after an additional heat treatment at 800° C. for 1 hour.

Phase separation of the glass upon melting is shown in FIGS. 7A-7B and 8A-8C, which are EDX hypermaps of cross-section TEM images of samples lifted from bulk and surface areas. The same magnification was used to in both TEM images. FIGS. 7A-7B show the bulk and surface areas, respectively, of Example 30 immediately after melting at 1650° C. and annealing at 650° C. versus quenching in water from the 1650° C. melt temperature. FIG. 7A, which shows the quenched sample, is phase separated and includes cuprite crystals within a degradable phase. Accordingly, the phase separation and formation of crystals was not suppressed by quenching. Accordingly, FIG. 7A shows phase separation occurs at 1600° C. or in the melt. Specifically, FIG. 7A shows a durable phase as the darkest color, the lightest parts indicate the presence of copper and parts surrounding the lightest parts and having a slightly darker color represents phosphorus. FIGS. 8A-8B show SEM images of a fracture cross-section and a polished cross-section, respectively, of Example 30 following an additional heat treatment at 800° C. for 1 hour. The additional heat treatment appears to have ripened the microstructure. The size of largest cuprite crystals increased and the number of nanoscale bright contrast phases is significantly reduced when compared to samples prepared by a standard method, as shown in FIGS. 4 and 5. In some embodiments, the concentration of copper exceeds the solubility limit in the degradable phase and the copper precipitates out of the degradable phase. Accordingly, the antimicrobial glass has antimicrobial activity in the molten state and when cooled into the finished state, without any additional heat treatment (e.g., heat treatment in hydrogen at temperatures up to about 600° C.). The antimicrobial glass includes Cu$^{1+}$ and/or CuO in sufficient amounts and present in the degradable phase, that copper ions are leached out and provide antimicrobial efficacy.

The release of the Cu$^{1+}$ ions provides the antimicrobial activity, as demonstrated in the log reduction of *Staphylococcus aureus* under the EPA Test when the glass was tested as-received and after 1 day under the conditions listed in Table 4.

The antimicrobial performance of the glasses described herein was tested by forming a coupon or substrate article having dimensions of 2.5 cm×2.5 cm.

To test the antimicrobial activity of the examples, the EPA Test was utilized. In the examples described herein, *Staphylococcus aureus* (ATCC 6538) was cultured for 5 consecutive days before the testing was performed. Bacterial culture was mixed with serum (5% final concentration) and Triton X-100 (final concentration 0.01%). Each sample/carrier was inoculated with 20 ul of the bacterial suspension and allowed to dry (typically, for about 20 minutes to 40 minutes) at room temperature and 42% relative humidity prior to being exposed to bacterial for a 2 hour exposure period. After 2 hours of exposure, bacteria are washed from the carrier using neutralizer buffer and plated onto Tryptic soy agar plates. Twenty-four hours after incubation at 37° C., bacteria colony formation was examined and counted. Geometric mean and percent reduction were calculated based on the colony number from samples relative to glass carrier or appropriate paint control.

The articles according to one or more embodiments were formed as follows. The glass was ground into a powder and mixed with a commercially available carrier described as a clear gloss protective finish, available under the trademark Polycrylic® from Minwax Company. The copper loading (wt %/wt %) was either about 5%, 10% or 15% (calculated on the basis that the glass includes about 20 wt % Cu). The mixed carrier and glass powder was then brush coated onto Pyvek® paper that was backed with a polymer film, before being coated. The coated Pyvek® paper was cut into 2.5×2.5 cm coupons for the antimicrobial performance testing.

Where a thermoplastic polymer was utilized, the glass powder was compounded with a commercially available polymer, having the trademark Peralthane®, at a temperature in the range from between 195° C.-220° C. and a rate of 50 rpm. The loading of the glass was at about 60-80%. The resulting polymer and glass composite was made into 2.5×2.5 cm coupons by a hot press process.

In some examples, an epoxy resin was utilized. In such examples, about 3.0 g of a commercially available epoxy resin, Erisys GE22, was combined with about 1 g of a curing agent, Amicure PACM and 2 g of ethanol in a 20 mL vial, and mixed well. About 10 g of the powdered glass was added and mixed well. The resulting mixture was cured at room temperature for a few days and then the vial was broken to gel the combination, which was further dried at room temperature for one day and at 65° C. for several hours. This results in dried epoxy resin/glass composite.

The examples that were combined with an epoxy resin were also tested to determine the density or porosity of the composite. This included placing the example in water for 2 minutes and then removing the example. The mass difference before and after placement in the water was measured to demonstrate the porosity of the example.

Figure 9:
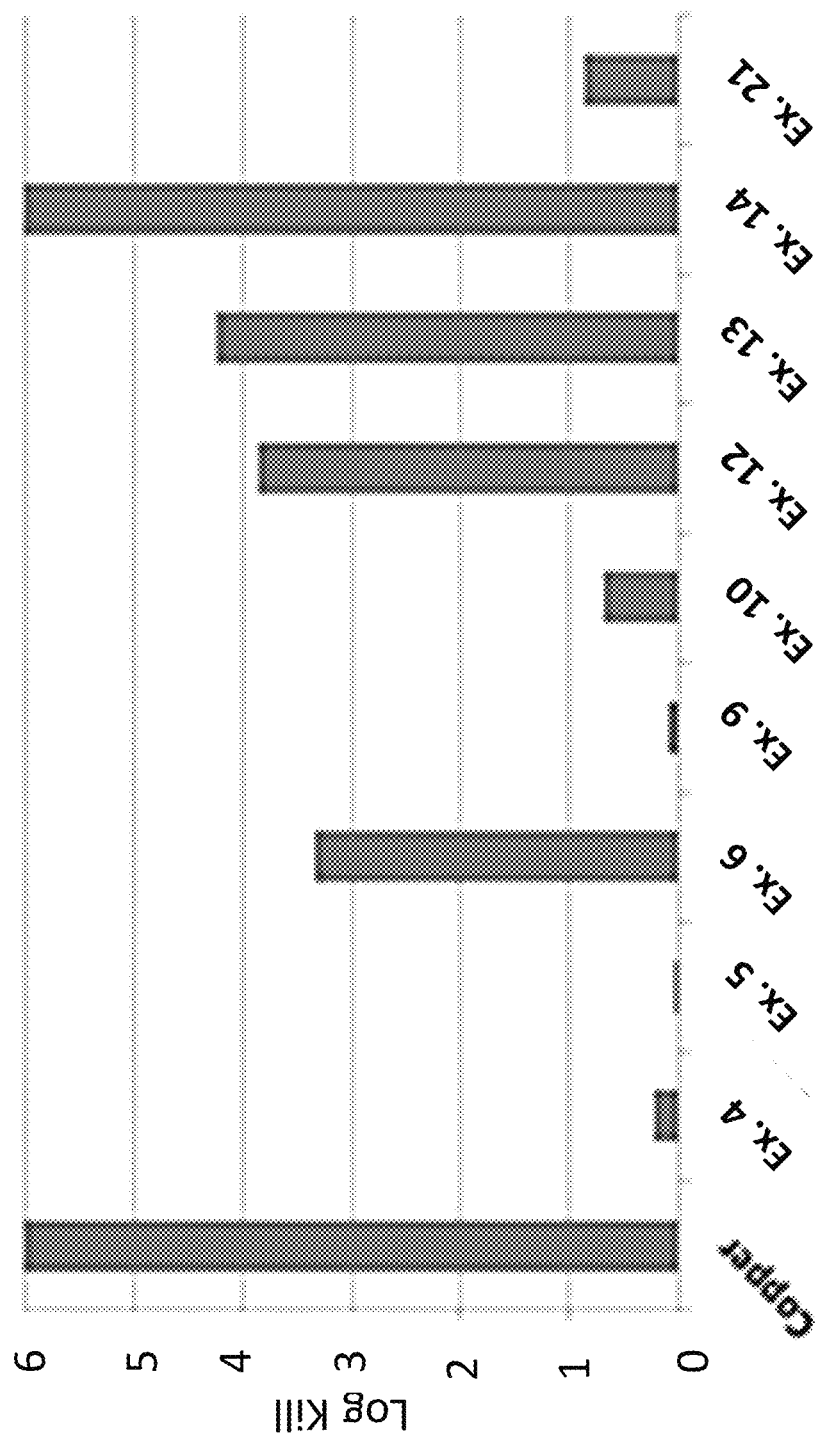
FIG. 9 illustrates the antimicrobial activity of glasses according to one or more embodiments.

Coupons made entirely of the glasses of Examples 4, 5, 6, 9, 10, 12, 13, 14 and 21 were tested under the EPA Test. In addition, a Comparative Substrate of pure copper metal was also tested under the EPA Test. FIG. 9 illustrates the antimicrobial performance of those glasses. Example 14 exhibited at least the same antimicrobial performance as the Comparative Substrate, with Examples 6, 12 and 13 exhibiting greater than 3 log reduction in *Staphylococcus aureus*.

Figure 10:
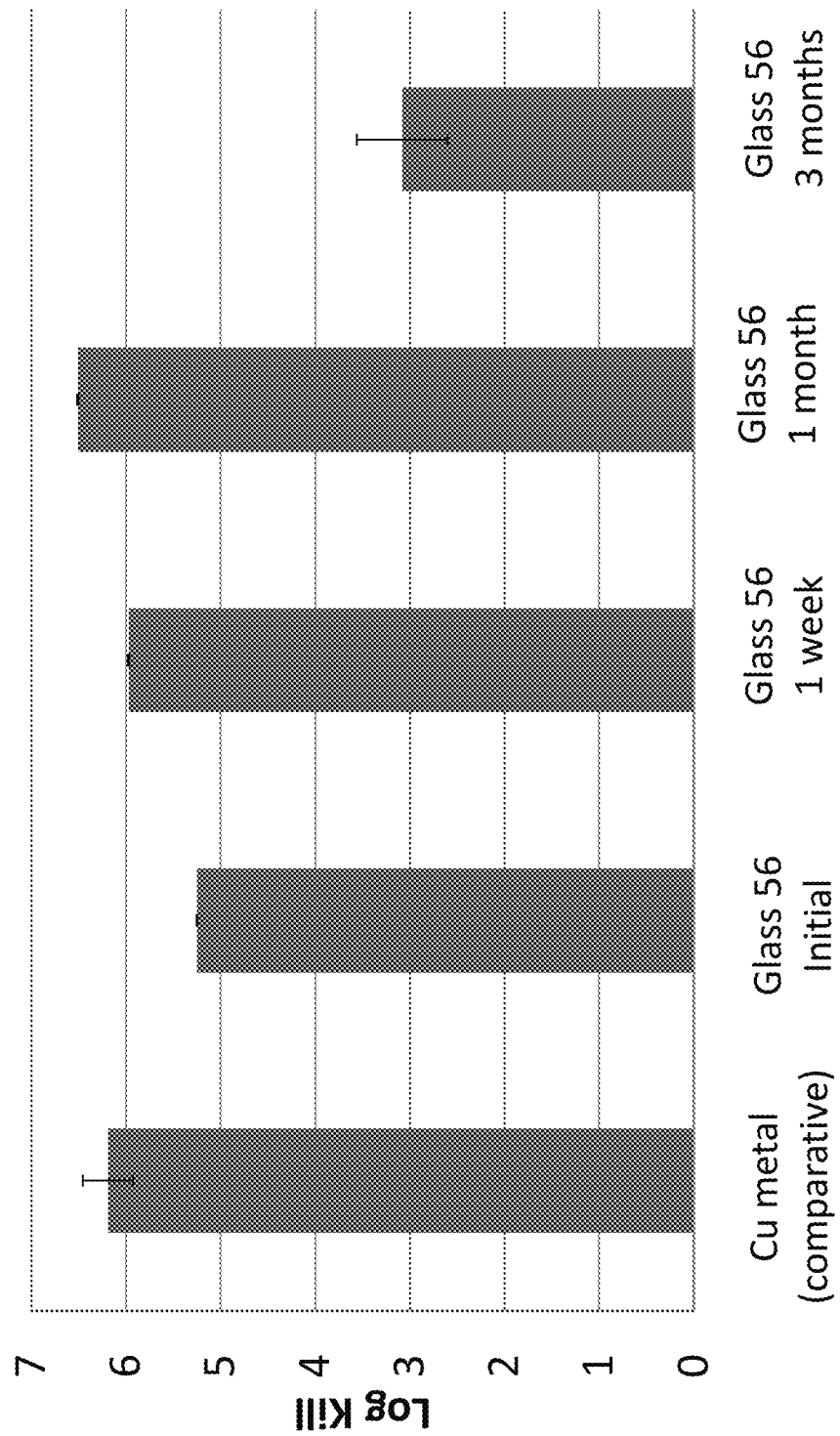
FIG. 10 is a graph showing the antimicrobial activity of an antimicrobial glass described herein, when formed into particles and combined with a polymer carrier, after various time periods.

Glass 56 was formed into particles having an average major dimension of about 1 μm or less. The particles were combined with a polymer carrier. The loading of the particles in the carrier was about 5%. The antimicrobial efficacy, as measured by the EPA test for *S. aureus* was evaluated immediately after the combination of the particles and the polymer carrier, one week after combination of the particles and the polymer carrier, one month after combination of the particles and the polymer carrier and three months after combination of the particles and the polymer carrier. FIG. 10 is a graph showing the antimicrobial efficacy after each period of time. As shown in FIG. 10, the glass exhibits at least a 2 log reduction in *S. aureus* even at three months after being formed into particles and combined with a polymer carrier. In addition, the combination of the glass particles and the polymer carrier exhibited greater than 5 log reduction at one month after combination.

Glass 56 and a Comparative Glass (A) (including 10% by weight silver ion content diffused therein) were evaluated for antimicrobial activity with respect to *Murine Norovirus* and cytotoxicity, under the Modified JIS Z 2801 Test for Viruses. Antimicrobial activity control samples and cytotoxicity control samples of Glass 56 and Comparative Glass A were also prepared, as described per the Modified JIS Z 2801 Test for Viruses. Table 5 shows the input virus control and the antimicrobial activity control results, Table 6 shows the cytotoxicity control results, Table 7 shows the results of Comparative Glass A after a 2-hour exposure time to *Murine Norovirus*, Table 8 shows the results of Glass 56 after a 2-hour exposure time to *Murine Norovirus*, Table 9 shows the cytotoxicity of Comparative Glass A and Glass 56 on RAW 264.7 cell cultures, and Table 10 shows the non-virucidal level of the test virus as measured on the cytotoxicity control samples for Comparative Glass A and Glass 56.

TABLE 5

Input Virus Control and Antimicrobial Activity Control Results.

| Dilution | Input Virus Control | Antimicrobial Activity Control | | |
|---|---|---|---|---|
| | | Replicate #1 | Replicate #2 | Replicate #3 |
| Cell control | 0 0 | 0 0 0 0 | 0 0 0 0 | 0 0 0 0 |
| $10^{-1}$ | + + | NT | NT | NT |
| $10^{-2}$ | + + | + + + + | + + + + | + + + + |
| $10^{-3}$ | + + | + + + + | + + + + | + + + + |
| $10^{-4}$ | + + | + + + + | + + + + | + + + + |
| $10^{-5}$ | + + | + + + + | + + + + | + + + + |
| $10^{-6}$ | + + | 0 + + + | + + 0 + | + + + + |
| $10^{-7}$ | 0 0 | 0 0 0 0 | 0 0 0 0 | 0 0 0 0 |
| $10^{-8}$ | 0 0 | 0 0 0 0 | 0 0 0 0 | 0 0 0 0 |
| $PFU_{50}/250$ μL | $10^{6.50}$ | $10^{6.25}$ | $10^{6.25}$ | $10^{6.50}$ |
| Mean $PFU_{50}/250$ μL | NA | $10^{6.33}$ | | |

(+) = positive for presence of test virus
(0) = No test virus recovered and/or no cytotoxicity present
(NA) = Not applicable
(NT) = Not tested

TABLE 6

Cytotoxicity Control Results.

| Dilution | Cytotoxicity Control (after 2 hour exposure time) | | |
|---|---|---|---|
| | Replicate #1 | Replicate #2 | Replicate #3 |
| Cell control | 0 0 0 0 | 0 0 0 0 | 0 0 0 0 |
| $10^{-2}$ | + + + + | + + + + | + + + + |
| $10^{-3}$ | + + + + | + + + + | + + + + |
| $10^{-4}$ | + + + + | + + + + | + + + + |
| $10^{-5}$ | + + + + | + + + + | + + + + |
| $10^{-6}$ | 0 0 0 0 | 0 0 + 0 | 0 + 0 0 |
| $10^{-7}$ | 0 0 0 0 | 0 0 0 0 | 0 0 0 0 |
| $10^{-8}$ | 0 0 0 0 | 0 0 0 0 | 0 0 0 0 |
| $PFU_{50}/250$ μL | $10^{5.50}$ | $10^{5.75}$ | $10^{5.75}$ |
| Mean $PFU_{50}/250$ μL | $10^{5.67}$ | | |

(+) = positive for presence of test virus
(0) = No test virus recovered and/or no cytotoxicity present

TABLE 7

Results of Comparative Glass A after 2 hour exposure time to Murine Norovirus.

| Dilution | Comparative Glass A - exposure to Murine Norovirus | | |
|---|---|---|---|
| | Replicate #1 | Replicate #2 | Replicate #3 |
| Cell control | 0 0 0 0 | 0 0 0 0 | 0 0 0 0 |
| $10^{-2}$ | + + + + | + + + + | + + + + |
| $10^{-3}$ | + + + + | + + + + | + + + + |
| $10^{-4}$ | + + + + | + + + + | + + + + |
| $10^{-5}$ | + + + + | + + + + | + + + + |

TABLE 7-continued

Results of Comparative Glass A after 2 hour exposure time to Murine Norovirus.

| | Comparative Glass A - exposure to Murine Norovirus | | |
|---|---|---|---|
| Dilution | Replicate #1 | Replicate #2 | Replicate #3 |
| $10^{-6}$ | 0 + + 0 | + 0 0 + | + + 0 0 |
| $10^{-7}$ | 0 0 0 0 | 0 0 0 0 | 0 0 0 0 |
| $10^{-8}$ | 0 0 0 0 | 0 0 0 0 | 0 0 0 0 |
| $PFU_{50}/250$ µL | $10^{6.00}$ | $10^{6.00}$ | $10^{6.00}$ |
| Mean $PFU_{50}/250$ µL | | $10^{6.00}$ | |
| Mean % reduction (based on cytotoxicity control) | | No reduction | |
| Mean $Log_{10}$ Reduction (based on cytotoxicity control) | | No reduction | |
| Mean % reduction (based on antimicrobial activity control) | | 53.2% | |
| Mean $Log_{10}$ Reduction (based on antimicrobial activity control) | | 0.33 $Log_{10}$ | |

(+) = positive for presence of test virus
(0) = No test virus recovered and/or no cytotoxicity present

TABLE 8

Results of Glass 56 after 2 hour exposure time to Murine Norovirus.

| | Glass 56 - exposure to Murine Norovirus | | |
|---|---|---|---|
| Dilution | Replicate #1 | Replicate #2 | Replicate #3 |
| Cell control | 0 0 0 0 | 0 0 0 0 | 0 0 0 0 |
| $10^{-2}$ | + + + + | 0 0 0 0 | 0 0 0 0 |
| $10^{-3}$ | + 0 + 0 | 0 0 0 0 | 0 0 0 0 |
| $10^{-4}$ | 0 0 0 0 | 0 0 0 0 | 0 0 0 0 |
| $10^{-5}$ | 0 0 0 0 | 0 0 0 0 | 0 0 0 0 |
| $10^{-6}$ | 0 0 0 0 | 0 0 0 0 | 0 0 0 0 |
| $10^{-7}$ | 0 0 0 0 | 0 0 0 0 | 0 0 0 0 |
| $10^{-8}$ | 0 0 0 0 | 0 0 0 0 | 0 0 0 0 |
| $PFU_{50}/250$ µL | $\leq 10^{3.00}$ | $\leq 10^{1.50}$ | $\leq 10^{1.50}$ |
| Mean $PFU_{50}/250$ µL | | $\leq 10^{2.00}$ | |
| Mean % reduction (based on cytotoxicity control) | | $\geq 99.98\%$ | |
| Mean $Log_{10}$ Reduction (based on cytotoxicity control) | | $\geq 3.67$ $Log_{10}$ | |
| Mean % reduction (based on antimicrobial activity control) | | $\geq 99.995\%$ | |
| Mean $Log_{10}$ Reduction (based on antimicrobial activity control) | | $\geq 4.33$ $Log_{10}$ | |

(+) = positive for presence of test virus
(0) = No test virus recovered and/or no cytotoxicity present

TABLE 9

Cytotoxicity of Control Comparative Glass A and Control Glass 56 on RAW 264.7 Cell Cultures.

| | Cytotoxicity Control | |
|---|---|---|
| Dilution | Comparative Glass A | Glass 56 |
| Cell control | 0 0 | 0 0 |
| $10^{-2}$ | 0 0 | 0 0 |
| $10^{-3}$ | 0 0 | 0 0 |
| $10^{-4}$ | 0 0 | 0 0 |
| $10^{-5}$ | 0 0 | 0 0 |
| $10^{-6}$ | 0 0 | 0 0 |
| $10^{-7}$ | 0 0 | 0 0 |
| $10^{-8}$ | 0 0 | 0 0 |
| $TCD_{50}/250$ µL | $\leq 10^{1.50}$ | $\leq 10^{1.50}$ |

(0) = No test virus recovered and/or no cytotoxicity present

TABLE 10

Non-virucidal Level of Test Substance (Neutralization Control).

| | Antimicrobial Activity + Cytotoxicity Control | |
|---|---|---|
| Dilution | Comparative Glass A | Glass 56 |
| Cell control | 0 0 | 0 0 |
| $10^{-2}$ | + + | + + |
| $10^{-3}$ | + + | + + |
| $10^{-4}$ | + + | + + |
| $10^{-5}$ | + + | + + |
| $10^{-6}$ | + + | + + |
| $10^{-7}$ | + + | + + |
| $10^{-8}$ | + + | + + |

(+) = Positive for the presence of test virus after low titer stock virus added (neutralization control)
(0) = No test virus recovered and/or no cytotoxicity present Comparative Glass A exhibited a 0.33 log reduction in *Murine Norovirus* (or a 53.2% mean reduction), following a 2 hour exposure time at room temperature (20° C.) in a relative humidity of 42%, as compared to the antimicrobial activity control sample. Glass 56, however, exhibited a greater than 4.33 log reduction in *Murine Norovirus* (or 99.995% mean reduction or greater), following a 2 hour exposure time at room temperature (20° C.) in a relative humidity of 42%, as compared to the antimicrobial activity control sample.

Comparative Glass A did not demonstrate a mean reduction in viral titer of *Murine Norovirus*, following a 2 hour exposure time at room temperature (20° C.) in a relative humidity of 42%, in the presence of a 5% fetal bovine serum organic soil load, as compared to the cytotoxicity control sample. Glass 56, however, exhibited a greater than 3.67 mean log reduction in *Murine Norovirus* (or at least 99.98% or greater mean reduction), following a 2 hour exposure time at room temperature (20° C.) in a relative humidity of 42%, in the presence of a 5% fetal bovine serum organic soil load, as compared to the cytotoxicity control sample.

The results shown in Table 10 indicate that each test sample was neutralized at a $PFU_{50}/250$ µL of $\leq 1.5$ $log_{10}$.

Figure 11:
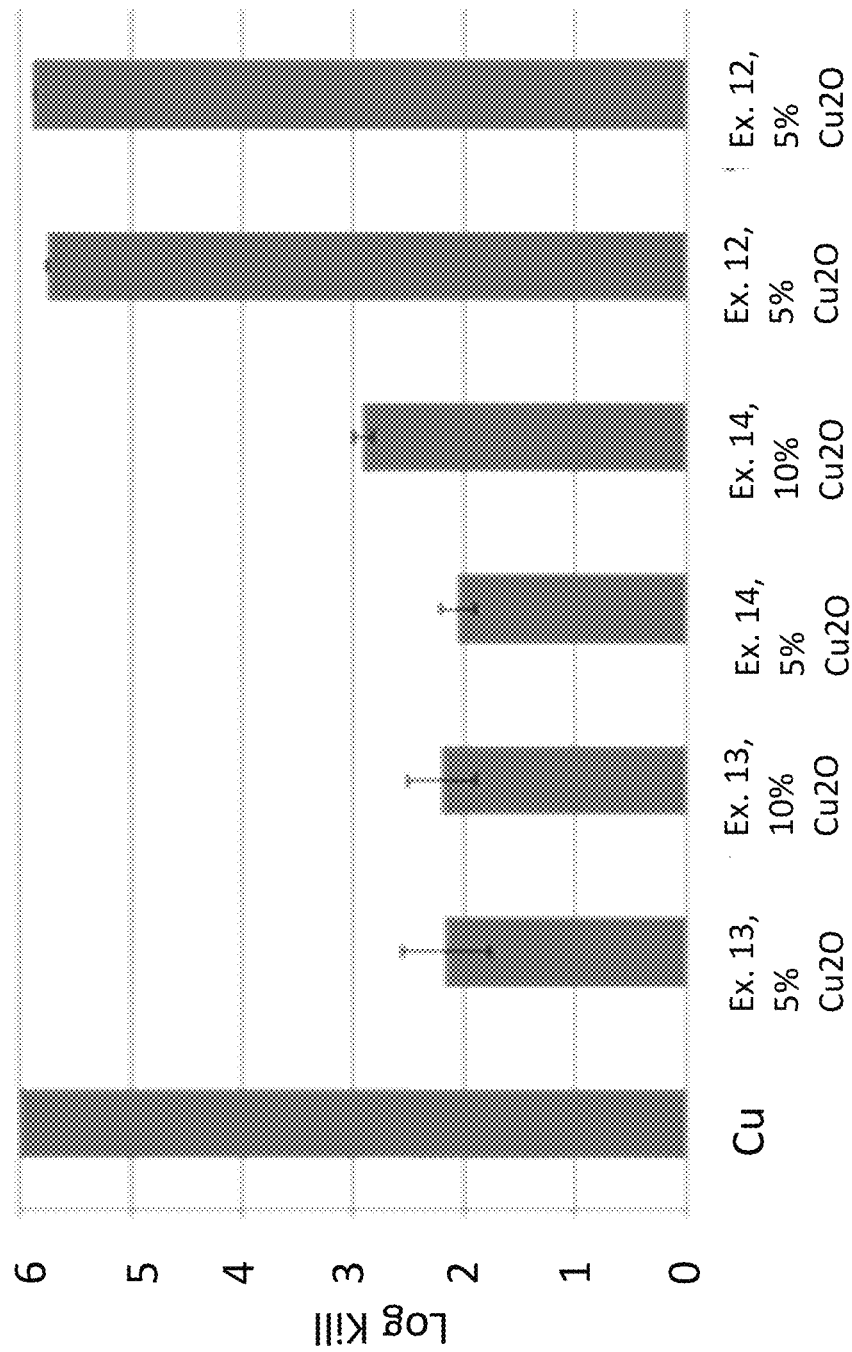
FIG. 11 is a graph illustrating the antimicrobial activity of various articles, according one or more embodiments.
Figure 12:
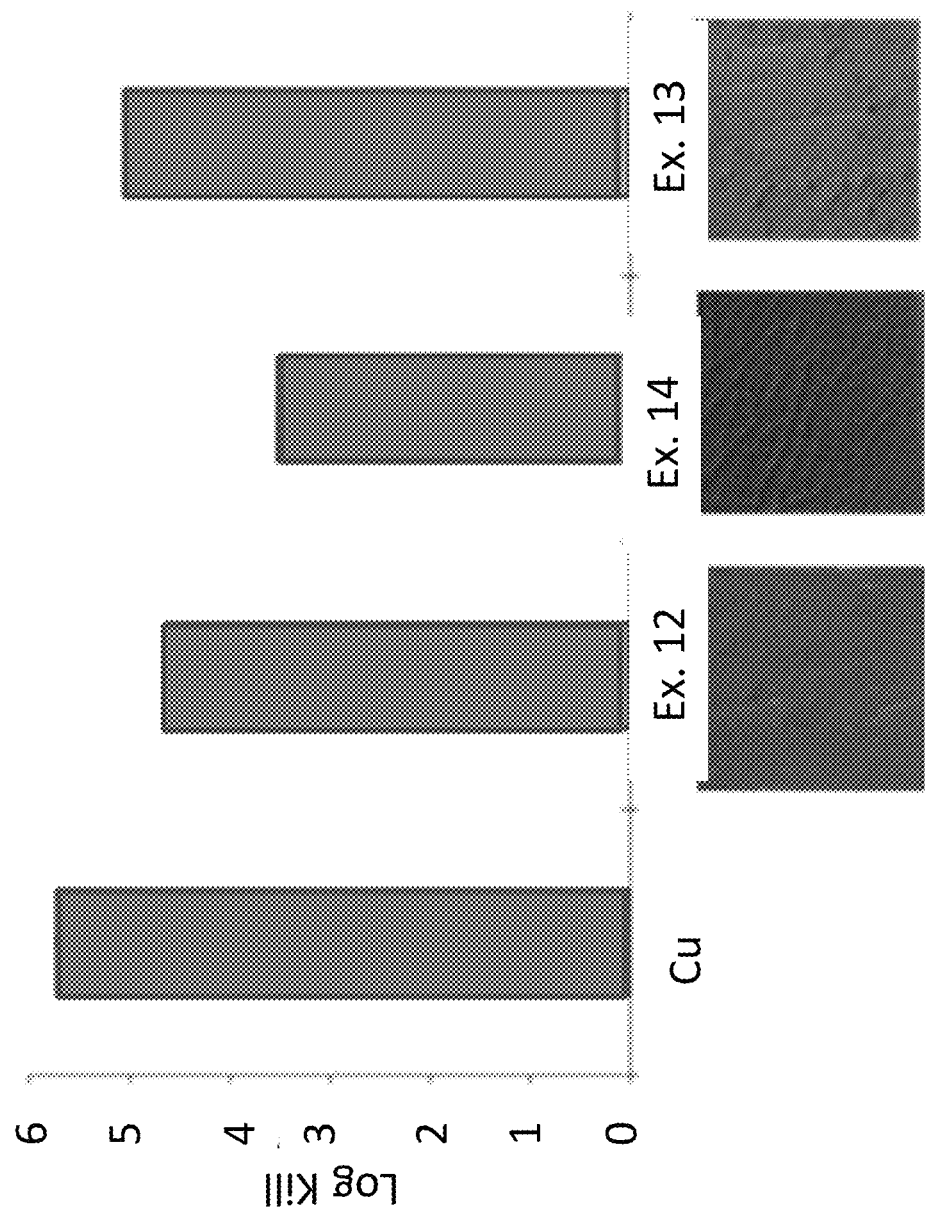
FIG. 12 is a graph illustrating the antimicrobial activity of various articles, according to one or more embodiments.

Examples 12, 13 and 14 were formed into a powder and mixed with Polycrylic® at different loadings, based on $Cu_2O$ content. The mixtures were then coated onto Pyvek® paper (that was backed with a plastic film before coated) through a brushing process and cured for 1 week. The coated paper was cut into coupons for testing under the EPA Test. FIGS. 11 and 12 illustrate the results. FIG. 11 shows the antimicrobial performance of the coupons, having different copper loadings. FIG. 12 illustrates the antimicrobial performance of the composites with 15% $Cu_2O$.

Example 12 was ground into a powder and mixed with Pearlthane® polyurethane to provide a composite having different amounts of glass (by weight percent). The powdered glass and polyurethane were mixed at 195-220° C. for several minutes. The resulting combination was made into a 2.5 cm×2.5 cm coupon using melt processing, and evaluated for antimicrobial performance using the EPA Test. The results are provided in FIG. 13.

Figure 14:
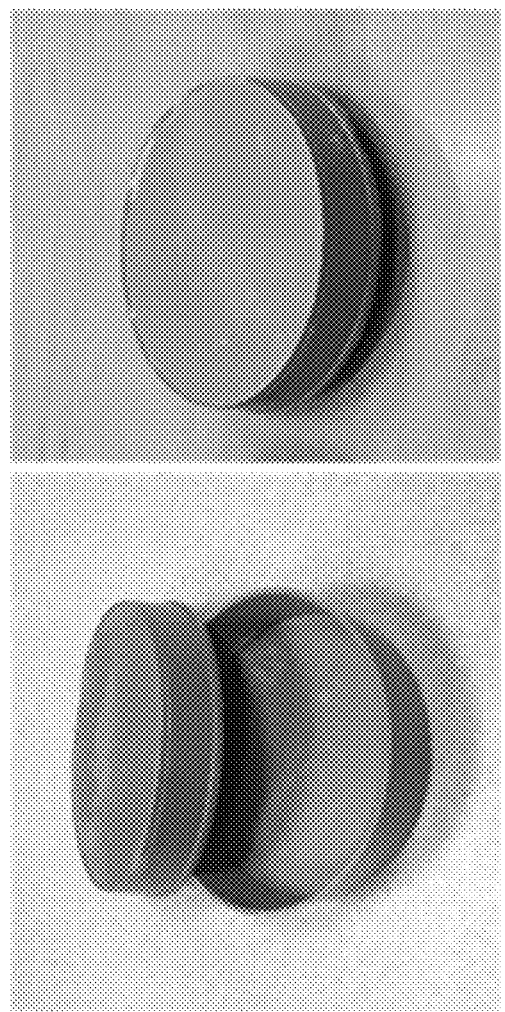
FIG. 14 shows images of injection molded articles made from Example 12 and a polymer.

Injection molded articles were formed to evaluate antimicrobial activity when the surface is typically covered by a thin layer of matrix polymer. In such articles, the matrix polymer is typically hydrophobic and may affect antimicrobial performance. As shown in FIG. 14, surface treatment can improve antimicrobial performance. To prepare the injection molded samples, Example 12 was ground into a powder and mixed with Pearlthane® polyurethane to provide an injection moldable composite having 60 wt % glass. The composite was injection molded in a petri dish as shown in FIG. 14 to provide four injection molded samples (Samples A-D) that were evaluated for antimicrobial performance using the EPA Test. Sample A was not subjected to surface treatment. Sample B was sanded to remove about 10 mg of top surface of the sample. Samples C and D were subjected to plasma treatment using 100 W of power and pressure of 2 torr for 5 minutes using two different gases, as shown in Table 11. FIG. 15 shows the log reduction of Samples A-D.

TABLE 11

Plasma Treatment condition for Samples C and D.
Table 115

| Material | Time, min | Power, W | Pressure, torr | Gas |
|---|---|---|---|---|
| Sample C | 5 | 100 | 2 | air |
| Sample D | 5 | 100 | 2 | $N_2/H_2$ (94/6% by volume) |

As discussed herein, thermoplastic polymers may be utilized to form the articles described herein through melt compounding processes. Articles using a thermoplastic polymer may also be formed by in situ polymerization and then into an article by a casting process. An epoxy resin (which is a thermosetting polymer) was used to demonstrate the concept. The epoxy resin was made from Erisys GE22 and Amicure PACM, which were mixed well in presence of alcohol. Example 12 was ground into a powder and added to the mixture according to Table 12, resulting in a paste-like material that was cast into a mold. In this example, a glass vial was used as a mold. The combination of the epoxy resin and ground glass was then cured at room temperature for a few days. The mold was then removed and the resulting article was dried at room temperature for one day and at 65° C. for a few hours.

TABLE 12

Composition for making an article with epoxy resin and ground glass from Example 12.
Table 12

| Materials | Weight, parts | Weight, parts | Weight, parts |
|---|---|---|---|
| Erisys GE22 | 1 | 1 | 3 |
| Amicure PACM | 0.3 | 0.3 | 1 |
| Ethanol | 6 | 5 | 2 |
| Example 12 | 15 | 10 | 10 |

Depending on the loading of the glass in the article, the resulting article may be porous or dense. The porosity increases with the increase of glass loading as seen in Table 13, in which the water uptake by the articles was measured after soaking the article in water for 2 minutes. Different articles were made from the same epoxy as used in Table 12 was combined with different amounts of ground glass from Example 12. The article was made using gel casting.

TABLE 13 water uptake of articles using epoxy resin and different loadings of ground glass from Example 12.
Table 13

| Example 12 glass loading (wt %/wt %) | Water uptake in 2 minutes, % |
|---|---|
| 71 | 0.5 |
| 88 | 5.9 |
| 92 | 20.7 |

It will be apparent to those skilled in the art that various modifications and variations can be made without departing from the spirit or scope of the invention.

What is claimed is:

1. An article comprising a glass, wherein the glass comprises a cuprite phase comprising a plurality of $Cu^{1+}$ ions; a first phase comprising at least one of $B_2O_3$, $P_2O_5$ and $R_2O$, wherein R is selected from the group consisting of K, Na, Li, Rb, Cs and combinations thereof; and a second phase, wherein the glass comprises a surface portion having a depth of less than about 5 nanometers (nm), the surface portion comprising a plurality of copper ions wherein at least 75% of the plurality of copper ions are $Cu^{1+}$.

2. The article of claim 1, further comprising a polymer, wherein the polymer comprises a thermoplastic polymer, a polyolefin, an injection moldable thermosetting polymer or combinations thereof.

3. The article of claim 2, further comprising a glass to polymer ratio in the range from about 10:90 to about 90:10, based on weight percent.

4. The article of claim 1, further exhibiting any one or more of
a 2 log reduction or greater in a concentration of any one or more of *Staphylococcus aureus, Enterobacter aerogenes, Pseudomonas aeruginosa* bacteria, Methicillin Resistant *Staphylococcus aureus*, and *E. coli*, under the EPA Test Method for Efficacy of Copper Alloy as a Sanitizer testing conditions,
a 4 log reduction or greater in a concentration of any one or more of *Staphylococcus aureus, Enterobacter aerogenes, Pseudomonas aeruginosa* bacteria, Methicillin Resistant *Staphylococcus aureus*, and *E. coli*, under the JIS Z 2801 (2000) testing conditions or a Modified JIS Z 2801 Test for Bacteria, and
a 4 log reduction or greater in a concentration of *Murine Norovirus*, under a Modified JIS Z 2801 Test for Viruses.

5. The article of claim 1, wherein the cuprite phase is dispersed in at least one of the first phase and the second phase.

6. The article of claim 1, wherein the second phase comprises $SiO_2$.

7. The article of claim 1, wherein the first phase comprises Cu¹.

8. The article of claim 1, wherein the cuprite phase comprises at least about 10 weight percent of the glass.

9. The article of claim 1, wherein the glass comprises a surface, a glass network and a glass matrix, and wherein the plurality of $Cu^{1+}$ ions is disposed on the surface and in at least one of the glass network and the glass matrix.

* * * * *

UNITED STATES PATENT AND TRADEMARK OFFICE
CERTIFICATE OF CORRECTION

PATENT NO. : 9,622,483 B2
APPLICATION NO. : 14/623077
DATED : April 18, 2017
INVENTOR(S) : Dana Craig Bookbinder et al.

Page 1 of 1

It is certified that error appears in the above-identified patent and that said Letters Patent is hereby corrected as shown below:

In the Claims

In Column 52, Line 54, in Claim 7, delete "Cu'." and insert -- $Cu^{1+}$. --.

Signed and Sealed this
Twenty-fourth Day of December, 2024

Derrick Brent
*Acting Director of the United States Patent and Trademark Office*